(12) United States Patent
Huang et al.

(10) Patent No.: US 11,513,132 B2
(45) Date of Patent: Nov. 29, 2022

(54) SOLID PHASE EXTRACTION, DERIVATIZATION WITH CROWN ETHERS, AND MASS SPECTROMETRY, METHODS, REAGENTS AND KITS

(71) Applicant: Tecan SP, Inc., Baldwin Park, CA (US)

(72) Inventors: Qi Huang, Camarillo, CA (US); Philip Dimson, San Pedro, CA (US); Emmanuel Luis Maloles Chanco, Rancho Cucamonga, CA (US)

(73) Assignee: TECAN SP, INC., Baldwin Park, CA (US)

( * ) Notice: Subject to any disclaimer, the term of this patent is extended or adjusted under 35 U.S.C. 154(b) by 848 days.

(21) Appl. No.: 16/431,208

(22) Filed: Jun. 4, 2019

(65) Prior Publication Data

US 2019/0293667 A1    Sep. 26, 2019

Related U.S. Application Data

(63) Continuation of application No. 15/083,246, filed on Mar. 28, 2016, now abandoned.

(60) Provisional application No. 62/139,692, filed on Mar. 28, 2015.

(51) Int. Cl.
| | | |
|---|---|---|
| G01N 33/94 | (2006.01) | |
| G01N 33/82 | (2006.01) | |
| C07K 1/00 | (2006.01) | |
| C07K 1/36 | (2006.01) | |
| G01N 33/68 | (2006.01) | |
| G01N 33/74 | (2006.01) | |

(52) U.S. Cl.
CPC ............ *G01N 33/948* (2013.01); *C07K 1/00* (2013.01); *C07K 1/36* (2013.01); *G01N 33/6848* (2013.01); *G01N 33/743* (2013.01); *G01N 33/82* (2013.01); *G01N 2560/00* (2013.01)

(58) Field of Classification Search
CPC ............ G01N 33/948; G01N 33/6848; G01N 33/743; G01N 33/82; G01N 2560/00; C07K 1/00; C07K 1/36
See application file for complete search history.

(56) References Cited

U.S. PATENT DOCUMENTS

| | | | | | |
|---|---|---|---|---|---|
| 5,635,404 | A | * | 6/1997 | Wilson | .................... H01J 49/04 436/131 |
| 6,716,634 | B1 | * | 4/2004 | Myerson | ............. H01J 49/0431 436/86 |

(Continued)

FOREIGN PATENT DOCUMENTS

| | | | | |
|---|---|---|---|---|
| CA | 2706953 | A1 * | 6/2009 | ............. G01N 27/62 |
| CA | 3000272 | A1 * | 6/2009 | ............. G01N 27/62 |

OTHER PUBLICATIONS

Supplementary European Search Report, 16773954.9, dated Jan. 8, 2018.

(Continued)

*Primary Examiner* — David A Vanore
(74) *Attorney, Agent, or Firm* — Notaro, Michalos & Zaccaria P.C.

(57) ABSTRACT

The present disclosure is directed to methods reagents and kits for solid phase extraction, derivatization with crown ether containing derivatizing agents, and mass spectrometry of the derivatized analytes.

35 Claims, 6 Drawing Sheets

(56) References Cited

U.S. PATENT DOCUMENTS

| | | | | |
|---|---|---|---|---|
| 7,169,329 B2* | 1/2007 | Wong | ............... | B82Y 40/00 |
| | | | | 252/502 |
| 2009/0091844 A1* | 4/2009 | Jannard | ............... | G02B 26/004 |
| | | | | 359/689 |
| 2009/0137056 A1 | 5/2009 | Holmquist et al. | | |
| 2015/0087073 A1* | 3/2015 | Chambers | ............... | G01N 30/88 |
| | | | | 436/86 |
| 2016/0282371 A1* | 9/2016 | Huang | ............... | C07K 1/00 |
| 2019/0293667 A1* | 9/2019 | Huang | ............... | C07K 1/00 |

OTHER PUBLICATIONS

Wilson et al. "Electrospray ionization mass spectrometry of vitamin D derivatives", Bioorganic & Medicinal Chemistry Letters, vol. 3, No. 9, Sep. 1, 1993, pp. 1805-1808.

Wilson et al. "Applications of electrospray ionization mass spectrometry to neutral organic molecules including fullerenes", Journal of the American Society for Mass Spectrometry, Elsevier Science Inc. vol. 4, No. 7 Jul. 1, 1993, pp. 1044-0305.

* cited by examiner

SOLID PHASE EXTRACTION, DERIVATIZATION WITH CROWN ETHERS, AND MASS SPECTROMETRY, METHODS, REAGENTS AND KITS

PRIORITY

This patent application is a continuation of and claims priority to U.S. patent application Ser. No. 15/083,246 and claims the right of priority pursuant to 35 U.S.C. § 119(e) and is entitled to the benefit of the filing date of U.S. Provisional Patent Application Ser. No. 62/139,692, filed on Mar. 28, 2015, the content of which is hereby expressly incorporated by reference in its entirety.

INTRODUCTION

There is a need to obtain fast, streamlined, and automated methods for detection of particular analytes. In the medical context, such methods would facilitate the detection of analytes, such as drugs, hormones, signaling agents, and amino acids. In the agricultural and public health context, the detection of residual levels of antibiotics, pesticides or other contaminants is integral to the safety of the food we eat and water we drink. Furthermore, recent changes in the standards for food labeling, such as "hormone free" or "organic" have created a need for streamlined testing in the agricultural realm.

In many cases clinical quantification of particular analytes was carried out via radio immunoassays (RIA). In recent years, due to the technology advancement in Mass Spectroscopy, there is a gradual shift in testing platform from RIA to liquid chromatography mass spectrometry (LCMS). Often times, the LCMS based assays provide a fast, sensitive, and analyte specific readout, which an RIA assay may lack. However, certain analytes may be difficult to detect for a multitude of reasons. For instance, some analytes are difficult to detect as they are prone to be oxidized and degraded. Further, the current art in quantification of certain analytes often involves complex and cumbersome extraction procedures with unstable extraction recovery. For instance, unstable extraction recovery gives rise to results which are often unreliable, and with high lower limits of quantification (LLOQ); for example an LLOQ in >10 ng/mL range. Also, the existing extraction process is unable to provide a reliable sample for derivatization.

Drugs include both illegal and legal drugs and metabolites or derivatives thereof. The detection of these compounds for forensic or prescription compliance are very important. Again, these drugs may not be stable in bodily fluids and therefore, detection may be difficult. In any event, there is a great need for a fully automated and simplified detection/quantification procedure which minimizes the room for human involvement or error.

SUMMARY

This invention document provides materials and methods that can be used to measure the levels of mono-acylatable, mono-amine-containing, or mono-phenol-containing analytes. For instance, analytes of interest include neurotransmitters, hormones, estrogen hormones (estrone, estradiol, estriol), cannabinoids such as Δ-9-tetrahydrocannabinol (THC) and HU210, serotonin, amino acids, BPA and many other primary amine containing, or phenol containing molecules in a biological sample.

This invention document also provides materials and methods that can be used to measure cis-diene containing analytes, such as vitamin-D, its analogs and metabolites (e.g., 25-OH $D_3$, 25-OH $D_2$, 24,25-$(OH)_2$ $D_3$, 1,25-$(OH)_2$ $D_3$, 1,25-$(OH)_2$ $D_2$).

This invention document also provides materials and methods that can be used to derivatize and measure ketone, or aldehyde containing analytes, such as testosterone, progesterone, corticosterone, and many of the steroid hormones.

The desired analyte can be selectively and sensitively detected and measured by mass spectrometry, including tandem mass spectrometry technologies. The entire quantification process includes a sample preparation process that employs a solid phase extraction to capture the analyte, followed by a chemical derivatization of the analyte, then quantification via LC-MS/MS technologies, as described herein.

It was discovered during this work that the combination of solid phase extraction with a chemical derivatization with a crown ether containing reagent and LC-MS/MS provides analyte specific, sensitive, accurate, stable and robust measurements of levels of analytes at pg/ml, fg/ml, or lower in blood plasma/serum sample and in the fg/ml range for detection of analytes from oral fluid. Quantification methods for were also developed with similar sensitivity and accuracy.

Sensitive and accurate measurements of these analytes at levels relevant to the clinical setting is useful, particularly at femto-gram or low pico-gram per milliliter range, at small sample size (100 uL or less of blood plasma/serum sample), with a simple process which can be easily configured to be automated, with an analyte specific results, without any analyte crossovers that are often seen under other analytical techniques such as radioimmunoassay (RIA).

BRIEF DESCRIPTION OF THE DRAWINGS

FIG. 2A provides the linear regression of THC and FIG. 2B provides the linear regression of HU210.

FIG. 3A provides the linear regression and FIG. 3B provides the chromatograms.

FIG. 4A provides the chromatogram and FIG. 4B provides a graph of the levels in each sample.

DETAILED DESCRIPTION

Figure 1:
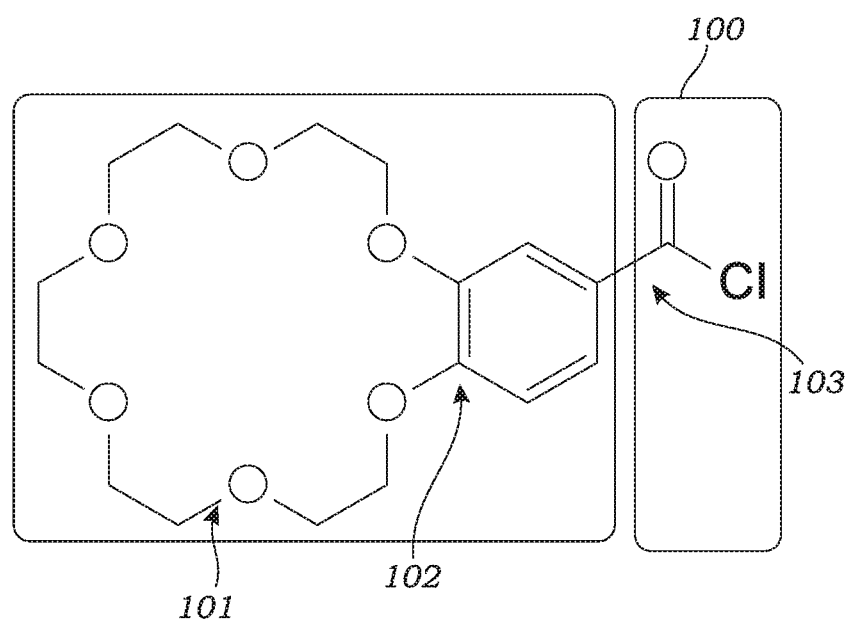
FIG. 1, demonstrates a specific embodiment of a derivatizing agent (100), having a crown-ether component (i.e., a sensitivity booster) (101), bound to a linker (i.e., the connector) (102), which will in turn bind the analyte (the derivatization functional group) (103).

The present methods are directed to methods of extraction, derivatization, and detection and/or quantification of analytes from a sample. The present methods employ a sample clean-up process via solid phase extraction (SPE), chemical derivatization process using crown ethers in conjunction with detection or quantification of analytes of interest to obtain analyte specific, robust, fast, sensitive, and accurate results. The derivatization of the analyte of interest shifts the analyte out of the region where it might potentially overlap with other biological agents found in the sample, enhances sensitivity of the analyte by trapping easily detected cations, and makes lipophilic analytes more hydrophilic and thus able to be analyzed. Thus, during detection, other biological molecules or contaminants which would ordinarily interfere with the accurate quantification of the analyte of interest are detected at a significantly different range of the spectrum (or eluted completely), allowing the accurate quantification of the analyte of interest. Furthermore, detection of the derivatized analyte is sensitized by detection of the trapped cations. Finally, hard-to-resolve lipophilic structures may be analyzed by this technique due to the unique hydrophobic/hydrophilic structure of the crown ethers. Such analyte detection is useful, e.g., in a clinical, a veterinarian, a forensic, and/or an environmental setting.

The present methods may include derivatization of the analytes of interest, and determination of the amount of one or more of the analytes by at least one of chromatography and/or mass spectrometry. In one embodiment, the present methods may also include a solid phase extraction (SPE) of the analyte from a biological sample. In one aspect, it is recommended that cation exchange based SPE may be used for capture amine containing analytes. For non-amine containing analytes, a reverse phase based SPE may be employed with a protein crash with or without a phospholipid removal process, where such sorbent may be C4-C18 alkyl bounded silica, phenyl bounded silica, biphenyl bonded silica, or other polymer sorbent. In other embodiments the final elution buffer with high pH ($8 \leq pH \leq 14$) may be used to elute amine containing analyte(s) from the cation exchange solid phase and optionally in situ derivatization of the analyte(s) of interest, cleanly preparing the derivative of the analyte for detection and/or quantification.

In additional embodiments, the non-amine containing analytes may be elute off from the SPE sorbent via a non-alcoholic, water miscible, organic solvent, such as acetonitrile, DMF, acetone, 1,4-dioxane, THF, NMP, DMSO, and etc., followed by direct derivatization of the analyte under a pH buffered condition. In a preferred embodiment, the present methods for detection of an amine containing analyte include cation exchange SPE, in situ derivatization with a crown ether and then quantification via LC-MS of the analyte of interest; permitting inline transitioning from biological sample to initial analyte extraction to detection and/or quantification. Similarly, for the preferred embodiment for detection of a non-amine containing analyte, present methods include reverse phase based SPE, organic elution followed by direct derivatization with a crown ether, then completed by LC-MS/MS quantification. Or in another embodiment, an anion exchange based SPE may be used for detection of an analyte with a carboxylic function group, with a high pH elution buffer mixed with suitable organic solvents such as acetonitrile, DMF, acetone, 1,4-dioxane, THF, NMP, DMSO, and etc., followed by direct derivatization of the analyte.

Also presented are kits for a detection and/or quantification assay. Such kits may include SPE columns (cartridges) and a crown ether derivatization reagent. Optionally, such kits may also include a SPE conditioning solvent, loading buffer, washing buffer, and an eluent buffer, separately or together, and an HPLC column.

The present methods may detect the presence of a wide array of analytes. An analyte is any compound or composition of interest to be found in the sample of interest. More specifically, an analyte of interest is a compound having primary and or secondary amine groups, or that is monoacylatable, a mono-amine compound, and or, a phenolic moiety. It is preferred that there is a single acylation or amine. An analyte of interest can have a hydrazine, hydrazide, or hydroxylamine group. An analyte as disclosed herein may be a drug (illegal and FDA approved) and a derivative or a metabolite thereof, a pesticide and a derivative or metabolite thereof, an environmental contaminate and a derivative or metabolite thereof, or a biologic compound such as, e.g., a hormone, a cytokine, a signaling agent, an amino acid, cholesterol or one of its derivatives, a fatty acid or a glycolipid, and a derivative or metabolite thereof.

In one embodiment, an analyte is vitamin D, its analogs and metabolites (for example, some members described herein without limitation include: 25-OH vitamin $D_3$, 25-OH $D_2$, 24,25-$(OH)_2$ vitamin $D_3$, 1,25-$(OH)_2$ vitamin $D_3$, and 1,25-$(OH)_2$ vitamin $D_2$, Cholecalciferol, 25-Hydroxycholecalciferol, 1α,25-Dihydroxycholecalciferol, Ergocalciferol, 1α,25-Dihydroxyergocalciferol, 22,23-Dihydroergocalciferol, 1α,24R,25-Trihydroxycholecalciferol, (6Z)-tacalciol, Tachysterol$_3$, Isovitamin $D_3$, Dihydrotachysterol$_3$, calcitrol, calcipotriol, etc.).

In one embodiment, an analyte is a monoamine neurotransmitter, or one of its derivatives or metabolites.

In another embodiment, an analyte is an estrogen including Estrone (E1), Estradiol (E2), Estriol (E3), and Estetrol (E4).

In another embodiment, an analyte is a phytoestrogen, including daidzein, formononetin, genistein, biochanin A, coumestrol, 4'-methoxycoumestrol, repensol, trifoliol, or 17-beta-estradiol.

In another embodiment, an analyte is a cannabinoid or one of its derivatives or metabolites.

Examples of cannabinoids or one of its derivatives or metabolites include a Cannabigerol-type (CBG) cannabinoid such as, e.g., Cannabigerol, Cannabigerol monomethyl ether, Cannabinerolic acid A, Cannabigerovarin, Cannabigerolic acid A, Cannabigerolic acid A monomethyl ether, and Cannabigerovarinic acid A; a Cannabichromene-type (CBC) cannabinoid, such as, e.g., (±)-Cannabichromene, (±)-Cannabichromenic acid A, (±)-Cannabivarichromene, (±)-Cannabichromevarin, or (±)-Cannabichromevarinic acid A; a Cannabidiol-type (CBD) cannabinoid such as, e.g., (−)-Cannabidiol, Cannabidiol momomethyl ether, Cannabidiol-C4, (−)-Cannabidivarin, Cannabidiorcol, Cannabidiolic acid, Cannabidivarinic acid; a Cannabinodiol-type (CBND) cannabinoid such as, e.g., Cannabinodiol or Cannabinodivarin; a Tetrahydrocannabinol-type (THC) cannabinoid such as, e.g., Δ9-Tetrahydrocannabinol, Δ9-Tetrahydrocannabinol-C4, Δ9-Tetrahydrocannabivarin, Δ9-Tetrahydrocannabiorcol, Δ9-Tetrahydro-cannabinolic acid A, Δ9-Tetrahydro-cannabinolic acid B, Δ9-Tetrahydrocannabinolic acid-C4 A, Δ9-Tetrahydro-cannabinolic acid-C4 B, Δ9-Tetrahydro-cannabivarinic acid A, Δ9-Tetrahydrocannabiorcolic acid A, Δ9-Tetrahydro-cannabiorcolic acid B, (−)-Δ8-trans-(6aR,10aR)-Δ8-Tetrahydrocannabinol, (−)-Δ8-trans-(6aR,10aR)-Tetrahydrocannabinolic acid A, (−)-(6aS,10aR)-Δ9-Tetrahydrocannabinol; a Cannabinol-type (CBN) cannabinoid such as, e.g., Cannabinol, Cannabinol-C4, Cannabivarin, Cannabinol-C2, Cannabiorcol, Cannabinolic acid A, Cannabinol methyl ether; a Cannabitriol-type (CBT) cannabinoid such as, e.g., (−)-(9R,10R)-trans-Cannabitriol, (+)-(9S,10S)-Cannabitriol, (±)-(9R,10 S/9S,10R)-Cannabitriol, (−)-(9R,10R)-trans-10-O-Ethyl-cannabitriol, (±)-(9R,10R/9S,10S)-Cannabitriol-C3, 8,9-Dihydroxy-Δ6a(10a)-tetrahydrocannabinol, Cannabidiolic acid A cannabitriol ester, (−)-(6aR,9S,10S,10aR)-9,10-Dihydroxy-hexahydrocannabinol, (−)-6a,7,10a-Trihydroxy-Δ9-tetrahydrocannabinol, 10-Oxo-Δ6a(10a)-tetrahydrocannabinol; a Cannabielsoin-type (CBE) cannabinoid such as, e.g., (5aS,6S,9R,9aR)-Cannabielsoin, (5aS,6S,9R,9aR)-C3-Cannabielsoin, (5aS,6S,9R,9aR)-Cannabielsoic acid A, (5aS,6S,9R,9aR)-Cannabielsoic acid B, (5aS,6S,9R,9aR)-C3-Cannabielsoic acid B, Cannabiglendol-C3, Dehydrocannabifuran, or Cannabifuran; an Isocannabinoid such as, e.g., (−)-Δ7-trans-(1R,3R,6R)-Isotetrahydrocannabinol, (±)-Δ7-1,2-cis-(1R,3R,6S/1 S,3S,6R)-Isotetrahydrocannabivarin, or (−)-Δ7-trans-(1R,3R,6R)-Isotetrahydrocannabivarin; a Cannabicyclol-type (CBL) cannabinoid such as, e.g., (±)-(1 aS,3aR,8bR,8cR)-Cannabicyclol, (±)-(1aS,3aR,8bR,8cR)-Cannabicyclolic acid A, or (±)-(1aS,3aR,8bR,8cR)-Cannabicyclovarin; a Cannabicitran-type (CBT) cannabinoid such as, e.g., Cannabicitran; and a Cannabichromanone-type (CBCN) cannabinoid such as, e.g., Cannabichromanone, Cannabichromanone-C3, or Cannabicoumaronone. Furthermore, the analyte may be a synthetic cannabinoid such as HU210, cannabicyclohexanol, JWH-073, JWH-018, AM-2201, CP-47,497 (as well as its derivatives and metabolites), JWH-015, JWH-081, JWH-133, JWH-200, JWH-250, JWH-398, JTE-907, CP 55,244, CP 55,940, HU210, HU-211, WIN 55,212-2, AM-694, AM-1248, AM-2201, AM-2233, EAM-2201, MAM-2201, MN-25, NNE1, 2NE1, UR-144, 5F-UR-144, XLR11, AKB48, AKB-NI, BAY 38-7271, BB-22, CB-25, CB-52, AB-001, AB-034, PB-22, 5F-PB-22, RCS-4, STS-135, URB-597, and URB-754.

In another embodiment, an analyte is a thyroid hormone or one of its derivatives or metabolites. Examples of thyroid hormones or one of its derivatives or metabolites include 3,3',5-triiodothyronine ($T_3$), 3,5,5'-triiodothyronine ($rT_3$), and thyroxine ($T_4$).

In another embodiment, an analyte is an opiate, opioid or one of its derivatives or metabolites. Examples, of opiates or opioids or one of its derivatives or metabolites include the naturally-occurring benzylisoquinoline alkaloids (morphine, and oripavine), the semi-synthetic derivatives (hydromorphone, and oxymorphone), and the synthetic opioids (e.g., buprenorphine, etorphine, pentazocine).

In another embodiment, an analyte is arylcyclohexylamine or one of its derivatives or metabolites. Examples of an arylcyclohexylamine include Tiletamine, 3-Methoxetamine (MXE), Methoxyketamine, N-ethylnorletamine (Ethketamine)

In another embodiment, an analyte is an Amphetamine. Examples of Amphetamines are Amphetamine (itself), methamphetamine, ephedrine, cathinone, 3,4-methylenedioxy-N-methylamphetamine (MDMA, "Ecstasy"), and 2,5-Dimethoxy-4-mnethylamrphetanmine (DOM, or "STP").

In another embodiment, an analyte is an amino acid, an artificial amino acid, or a small peptide. Examples of the amino acid include but are not limited to: glycine, alanine, phenylalanine, tyrosine, GABA, tryptophan, cysteine, serine, valine, leucine, isoleucine, lysine, methionine, histidine, arginine, aspartic acid, asparagine, glutamic acid, glutamine, proline, and threonine.

Sample Preparation

Aspects of the present specification disclose, in part, a test sample. A test sample refers to any sample that may contain an analyte of interest. A test sample may be a biological sample, that is, a sample obtained from any biological source, such as an animal, a plant, a fungus, a microorganism, a cell culture, an organ culture, etc. In aspects of this embodiment, a biological sample includes a blood sample including a whole blood sample, a dry blood sample, a plasma sample, or a serum sample, a saliva sample, a lachrymal sample, a semen sample, a urine sample, cerebrospinal fluid sample, a bile sample, an embryonic fluid sample, a tissue sample, or any other sample that can be obtained, extracted or isolated from a biological source. Such biological samples may be obtained, for example in a medical or clinical setting, from a patient; that is, a living person, male or female, presenting oneself in a clinical setting for diagnosis, prognosis, or treatment of a disease or condition. The sample is preferably obtained from a patient, for example, a plasma specimen. The plasma specimen may be taken with or without the use of anticoagulants.

Such biological samples may be obtained, for example in a veterinarian setting, from an animal; that is, a pet animal, or a farm animal or livestock, a fish, or any other creatures that live in fresh water, ocean or sea, male or female, presenting oneself in a veterinarian setting for diagnosis, prognosis, prevention, or treatment of a disease or condition. The sample is preferably obtained from an animal, for example, a plasma specimen. The plasma specimen may be taken with or without the use of anticoagulants.

A test sample may be obtained from a plant or any vegetation source, in agricultural or environmental setting, from a leave, or a flower, or a stem, or a fruit, or a seed, or sprout, or a bark, or a root, etc.

A test sample may be obtained from a dead human body, or a dead animal, or a dead plant, or remains of a once living body, as in a forensic setting, or in an agricultural setting, or in an environmental setting, or in an archeological setting. A testing sample may be a blood sample, or a dry blood sample, or any other body fluid sample (e.g., saliva or other oral fluid), or any other dry body fluid sample, or a body tissue sample taken from anywhere of the body or remains of a dead human, animal, or plant.

A test sample may be an environmental sample. Environmental samples are samples taken from dirt, plant matter, or fluid sources (such as ground water, oceans, or rivers etc.). Dirt (aka "soil samples") may be taken from agricultural sites or sites of environmental interest and may have the analyte extracted, including the removal of particulate matter.

Samples may be obtained by any known means. The sample may be preserved or pre-treated to ensure stability of the analyte of interest. Such preservation may be accomplished by chemical (such as hydrolysis or pH adjustment) or physical processes (such as refrigeration or freezing). When a sample is a solid or a tissue, it can be grounded, or extracted, or purified, or filtered, or centrifuged, to isolate the analyte of interest from the interfering components. Or a sample is a liquid, preferably, it is dissolved, or suspended, in a solution (or "loading buffer") having a pH range from weakly basic to neutral to weakly acidic; for example having a pH ranging from 10-3, or more preferably 9-4, or more preferably 8-5, or even more preferably 7-6, depending on the analyte of interest and the sorbent chemistry.

Any sample volume may be obtained as long as it is of sufficient volume to be useful in the methods disclosed herein. In aspects of this embodiment, a sample volume may be e.g., about 10 μL, about 25 μL, about 50 μL, about 75 μL, about 100 μL, about 125 μL, about 150 μL, about 175 μL, about 200 μL, about 225 μL, about 250 μL, about 275 μL, about 300 μL, about 325 μL, about 350 μL, about 375 μL, about 400 μL, about 425 μL, about 450 μL, about 475 μL, or about 500 μL. In other aspects of this embodiment, a sample volume may be e.g., at least 10 μL, at least 25 μL, at least 50 μL, at least 75 μL, at least 100 μL, at least 125 μL, at least 150 μL, at least 175 μL, at least 200 μL, at least 225 μL, at least 250 μL, at least 275 μL, at least 300 μL, at least 325 μL, at least 350 μL, at least 375 μL, at least 400 μL, at least 425 μL, at least 450 μL, at least 475 μL, or at least 500 μL. In yet other aspects of this embodiment, a sample volume may be e.g., at most 10 μL, at most 25 μL, at most 50 μL, at most 75 μL, at most 100 μL, at most 125 μL, at most 150 μL, at most 175 μL, at most 200 μL, at most 225 μL, at most 250 μL, at most 275 μL, at most 300 μL, at most 325 μL, at most 350 μL, at most 375 μL, at most 400 μL, at most 425 μL, at most 450 μL, at most 475 μL, or at most 500 μL. In still other aspects of this embodiment, a sample volume may be between e.g., about 10 μL and about at most 100 μL, about 10 μL and about at most 200 μL, about 10 μL and about at most 300 μL, about 10 μL and about at most 400 μL, about 10 μL and about at most 500 μL, about 10 μL and about at most 600 μL, about 10 μL and about at most 700 μL, about 10 μL and about at most 800 μL, about 10 μL and about at most 900 μL, about 10 μL and about at most 1000 μL, about 50 μL and about at most 100 μL, about 50 μL and about at most 200 μL, about 50 μL and about at most 300 μL, about 50 μL and about at most 400 μL, about 50 μL and about at most 500 μL, about 50 μL and about at most 600 μL, about 50 μL and about at most 700 μL, about 50 μL and about at most 800 μL, about 50 μL and about at most 900 μL, about 50 μL and about at most 1000 μL, about 100 μL and about at most 200 μL, about 100 μL and about at most 300 μL, about 100 μL and about at most 400 μL, about 100 μL and about at most 500 μL, about 100 μL and about at most 600 μL, about 100 μL and about at most 700 μL, about 100 μL and about at most 800 μL, about 100 μL and about at most 900 μL, or about 100 μL and about at most 1000 μL.

Purification

A test sample disclosed herein may be purified. As used herein, the terms "purified", "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions of the selected analyte by mass spectrometry. Relative reduction as this term is used does not require that any substance, present with the analyte of interest in the material to be purified, is entirely removed by purification. When detecting some analytes (particularly drugs) in a urine sample, hydrolysis may be necessary to remove the glucuronide bonding which prevents the solubility and extraction of the analyte. This purification technique is usually performed by enzyme or acid hydrolysis of the urine. Alternatively, removing particulate matter (e.g., by centrifugation or filtration), protein precipitation (optionally by a "protein crash" method) with or without phospholipid removal, may be useful purification techniques.

Purification may also be performed to create or make available reactive amino or phenolic groups, suitable for the derivatization reaction. These methods include hydrolysis of esters or amines, or acid hydrolysis of sugars.

Such purification by pre-processing is not limited, but serves to prepare the sample for extraction with one or more of solid phase extraction, supported liquid extraction (SLP), and liquid liquid extraction (LLP).

Solid Phase Extraction

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

SPE using an ion exchange extraction procedure is applied to extract the analytes of interest from the sample. Such analyte can be ionized under certain ranges of pH of a buffer. SPE may be performed with a range of characteristics suitable depending on the analyte. Analytes such as monoamine neurotransmitters, or catecholamines, or metanephrines, or amino acids, or thyroid hormones, or carboxylic acids, maybe extracted, or retained, or purified, via ion exchange extraction based SPE. More specifically strong to weak cation exchange may be used. SPE using a cation exchange is one example applied in the present methods of extracting analyte of interest from a blood plasma sample. Weak cation exchange cartridges with a divinylbenzene- (DVB-) based polymer sorbent are particularly exemplified for the SPE of catecholamines and metanephrines. SPE using a strong cation exchange extraction based SPE may also be used to purify analytes from the blood plasma sample with an SPE cartridge filled with a DVB-based polymer sorbent via stronger elution solvent. Moreover, silica based carboxylic acid sorbents may also be useful to extract catecholamine and metanephrines from the plasma samples.

A strong cation exchange (sulfonic acid chemistry) sorbent either based on silica or one or more polymers may also be useful to extract analytes in the SPE process. SPE with a strong cation exchange sorbent are particularly exemplified for the SPE of thyroid hormones (T3/rT3/T4). An amino acid analyte may be similarly extracted with a strong cation exchange sorbent, either polymer based, or silica based.

An anion exchange polymer may also be used to extract a carboxylic acid analyte, or an amino acid analyte, or a sulfonic acid analyte, or a phosphonic acid analyte.

Particular columns of interest for use in the present methods to extract steroids include the CEREX® PWCX, 1 mL Columns, 10 mg, 96/Pk (catalog number 6750-0101R. For thyroid hormones the CEREX® PSCX, 1 mL Columns, 10 mg, 96/Pk (catalog number 687-0101R) are suitable.

In yet another embodiment, a reverse phase SPE column or cartridge may be used to extract, or purify, or retain the analyte of choice when the analyte does not have an amino group, such as vitamin d its derivatives and metabolites, estrogen hormones, or cannabinoids, or flavonoids. The sorbent of choice during this SPE/purification may include alkyl bounded silica (C4, C8, C12, and C18), cyano bounded silica, phenyl bounded silica, or biphenyl bounded silica. Particular columns of interest include Trace-N® 1 cc columns (a hydrophobic polymer/weak anion exchange column, 10 um particle size, 300 A, from SPE Ware).

Sizes of the columns may range, but in particular, a column volume may preferably range from 50 uL to 3000 uL, with a sorbent loading between 100 ug to 50 mg. In another embodiment, the more preferred column size ranges from 100 uL to 2000 uL with a sorbent loading between 1 mg to 20 mg. In another embodiment, the more preferred column size ranges from 200 uL to 1000 uL with a sorbent loading between 2 mg to 10 mg. Shape and size of the SPE columns (cartridges) may be varied to fit a specific platform.

The particle size of the sorbent may further assist in the separation of the analyte of interest. In aspects of this embodiment, a particle size of a sorbent may have a mean diameter of, e.g., about 0.5 μm, about 1 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, or about 75 μm. In other aspects of this embodiment, a particle size of a sorbent may have a mean diameter of, e.g., at least 0.5 μm, at least 1 μm, at least 5 μm, at least 10 μm, at least 15 μm, at least 20 μm, at least 25 μm, at least 30 μm, at least 35 μm, at least 40 μm, at least 45 μm, at least 50 μm, at least 55 μm, at least 60 μm, at least 65 μm, at least 70 μm, or at least 75 μm. In yet other aspects of this embodiment, a particle size of a sorbent may have a mean diameter of, e.g., at most 0.5 μm, at most 1 μm, at most 5 μm, at most 10 μm, at most 15 μm, at most 20 μm, at most 25 μm, at most 30 μm, at most 35 μm, at most 40 μm, at most 45 μm, at most 50 μm, at most 55 μm, at most 60 μm, at most 65 μm, at most 70 μm, or at most 75 μm. In still other aspects of this embodiment, a particle size of a sorbent may have a mean diameter in the range of, e.g., about 0.5 μm to about 10 μm, about 0.5 μm to about 20 μm, about 0.5 μm to about 30 μm, about 0.5 μm to about 40 μm, about 0.5 μm to about 50 μm, about 0.5 μm to about 60 μm, about 0.5 μm to about 70 μm, about 0.5 μm to about 80 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 5 μm to about 10 μm, about 5 μm to about 20 μm, about 5 μm to about 30 μm, about 5 μm to about 40 μm, about 5 μm to about 50 μm, about 5 μm to about 60 μm, about 5 μm to about 70 μm, about 5 μm to about 80 μm, about 10 μm to about 20 μm, about 10 μm to about 30 μm, about 10 μm to about 40 μm, about 10 μm to about 50 μm, about 10 μm to about 60 μm, about 10 μm to about 70 μm, or about 10 μm to about 80 μm.

A sample may be loaded on the SPE column with a loading solvent, or a loading buffer. The loading solvent may be deionized water, or a pH buffered aqueous solution, or an organic solvent, or a mixture of organic solvents, or a mixture of an organic solvent and deionized water, or a mixture of organic solvents with deionized water, or a pH buffered aqueous solution mixed with an organic solvent or a mixture of organic solvents. The pH buffered aqueous solution may be a phosphate buffered saline (PBS), or a phosphate buffer, or a carbonate buffer, or a succinate buffer, or a tartrate buffer, or a citric buffer, or a formic buffer, or an acetic buffer, or another commonly used buffer solution in a typical biochemical lab, or a mixture of any of the two, or more of the following, a phosphate buffer, or a carbonate buffer, or an acetic buffer, or a formic buffer, or a citric buffer, or a succinate buffer, or a tartrate buffer, or, with a pH range from weakly basic to neutral to weakly acidic; for example having a pH ranging from 10-3, or more preferably 9-4, or more preferably 8-5, or even more preferably 7-6, at a concentration range from 0.1 mM to 100 mM, or more preferably 0.5 mM to 50 mM, or more preferably 1 mM to 25 mM, or more preferably 5 mM to 10 mM. An organic solvent may be selected from acetonitrile, or acetone, or 1,4-dioxane, or DMF, or tetrahydrofuran (THF), or diethyl-ether, or ethyl acetate, or methyl acetate, or ethyl formate, methyl formate, or a mixture of thereof. In one embodiment, the sample is loaded onto the column in a QUANTISIL® extraction and/or transfer buffer (Immunalysis Corporation, Pomona, Calif.).

Upon loading the sample to the SPE column, the fluid is allowed to pass through the sorbent, via gravity, or a vacuum pulling through a vacuum manifold, or a nitrogen or inert gas pressure push through a positive pressure manifold, with or without an air drying process. The sample loaded cartridge may be further washed with a solvent. The selection of the washing solvent may be deionized water, or a pH buffered aqueous solution, or organic solvent, or a mixture of organic solvents, or a mixture of organic solvents with an aqueous buffer. An organic solvent may be acetonitrile, or methanol, or ethanol, or isopropanol, or butanol, or diethyl ether, or acetone, or 1,4-dioxane, or THF, or DMF, ethyl acetate, or methyl acetate, or ethyl formate, methyl formate, or a mixture of any of the above solvents.

Upon loading and washing, the loaded cartridge may be treated with an elution fluid directly, or dried first via a stream of, dry nitrogen, or another dry inner gas, passing through the cartridge.

Derivatization

Aspects of the present specification disclose, in part, a method of derivatization of the analyte of interest using a derivatizing agent. The analyte of interest reacts with a derivatizing agent to provide a derivative of the analyte. Derivatization may be in situ. This derivative displays an improved HPLC behavior, significantly improved tandem MS/MS sensitivity, and makes lipophilic analytes more hydrophilic. For instance the present method unexpectedly provides nearly, or over 1000-fold improvement in detection limitation and/or quantification sensitivity when quantifying vitamin D, cannabinoids, estrogen and other analytes from blood serum samples, by using LC-tandem MS/MS technologies.

A derivatizing reagent or derivatization reagent disclosed herein includes a derivatizing agent and a suitable solvent. The derivatizing agent is a compound that can react with a primary amino group, and/or a phenolic hydroxy group, and/or a primary alcohol (hydroxyl) group, and/or a aryl or alkyl thiol group, a cis-diene group, a carboxylic acid group, a ketone group, or an aldehyde group, present in an analyte disclosed herein. A derivatizing agent includes a crown-ether, a connector, and a derivatizing functional group.

In one embodiment, the derivatized structure has a crown-ether component (CE), a connector or linker component (L), a derivatization (or analyte binding) functional group (FG), and an analyte. Formula 1 provides the general structure of the claimed derivatizing agent:

CE-L-FG Formula 1

The crown ether CE, may attach to or be fused to the linker L, which is connected to the derivatizing functional group FG, which may covalently attach to certain selected analytes. One particular example of the derivatizing agent is shown in FIG. 1, demonstrating a specific embodiment of a derivatizing agent (100), having a crown-ether component (i.e., a sensitivity booster) (101), bound to a linker (also known as the connector) (102), link to a functional group, which will in turn covalently link to the analyte (the derivatization functional group)(103).

Crown ethers of interest include any crown ether and variants thereof. In one aspect the crown ether is optionally fused to one or more cyclohexyl or aryl groups, optionally where one or more oxygens in the crown is substituted with a heteroatom, such as nitrogen (i.e., aza-crown ethers) or sulfur (thia-crown ethers). In one embodiment, the crown ether includes a 12, 13, 14, 15, 16, 17, 18, 19, 20, 21, 22, 23, 24, 25, 26, 27, 28, 29, or 30 membered ring. In one embodiment, the crown ether ranges from 12 crown 4 to 24 crown 8. In one aspect, the "crown" of the crown ether is 12 Crown 4, 15 Crown 5, 16 crown 4, 18 Crown 6, 21 Crown 7, or 24 Crown 8.

The crown ether may have a lariat structure as well. The lariat structure may include a C1-C12 alkyl group (linear, cyclic, and/or branched), optionally substituted or interrupted. For instance, the lariat structure may serve as the linker or connector or linker between the crown ether and the bound analyte.

The linker or connector is bound to the crown ether by a simple covalent bond. In one embodiment, the linker or connector may be a $C_1$-$C_{12}$ linear, branched or cyclic alkyl group. In one aspect, the linker or connector may be a $C_1$-$C_6$ linear, branched or cyclic alkyl. In another aspect, the linker or connector is fused to the crown ether forming a six-membered phenolic ring.

The derivatization functional group that binds the analyte may include, without limitation, an acylating group, 4-Phenyl-1,2,4-triazolin-3,5-dione (PTAD), 1,2,4-traizoline-3,5-dione (TAD), Alkoxylamines, hydrazides, alcohols, or amines. In one embodiment, the derivatization functional group may be any acylating group as in Formula 2. Acylating reagents may include acyl chlorides or other acyl halides. Derivatizing agents may also fluoresce or participate in a colorimetric reaction to assist with the detection of the bound analyte.

Formula 2

The acylation group in the derivatizing agent is useful for analytes with a primary and secondary amine, aliphatic hydroxyl, or phenolic hydroxyl group. Such as monoamines, amino acids, estrogen hormones, THC, its metabolites and analogs, such as HU210, and etc. In one embodiment, the crown ether derivatizing agent with an acylating functional group includes, without limitation, any of the structures of Group I:

Group I

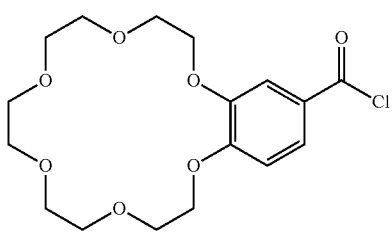

MB338

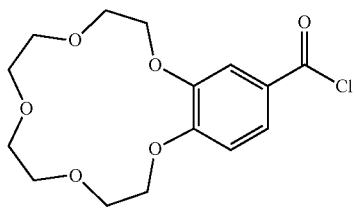

-continued

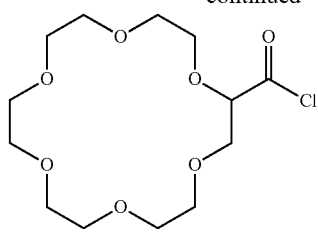

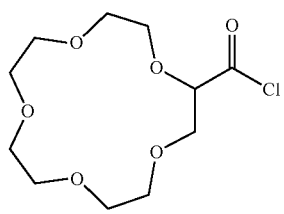

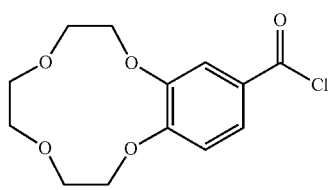

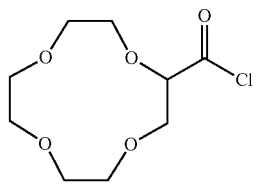

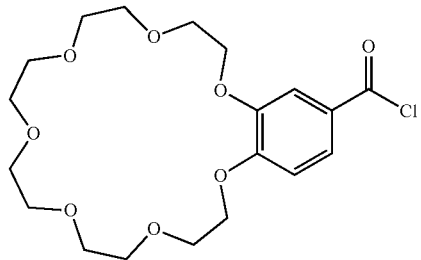

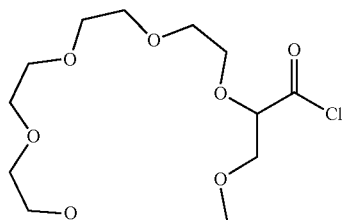

OR

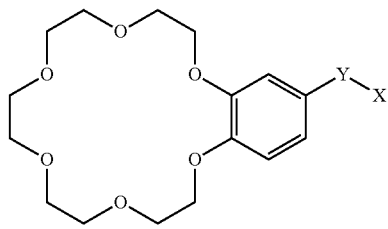

-continued

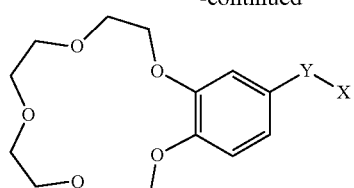
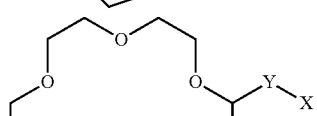
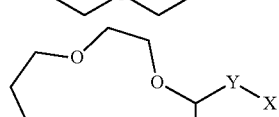
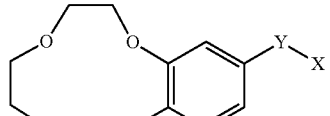
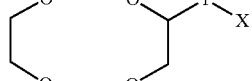
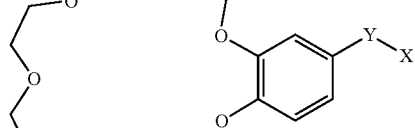
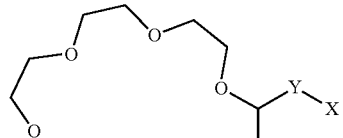
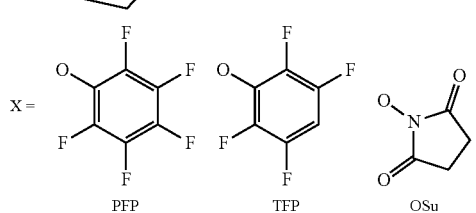

-continued

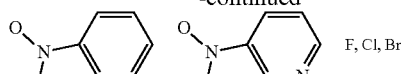
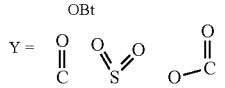

In one aspect, the crown ether derivatizing agent is MB338.

Crown either containing derivatizing agents for derivatizing a cis-diene containing analyte include, without limitation, crown ethers bound to 4-Phenyl-1,2,4-triazolin-3,5-dione (PTAD) or 1,2,4-traizoline-3,5-dione (TAD) either directly, or by a linking/connecting group or lariat. Such derivatizing agents include, without limitation, any of the structures of Group II:

Group II

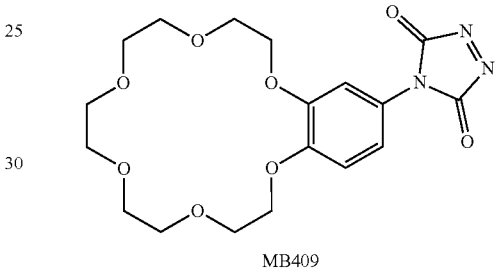

MB409

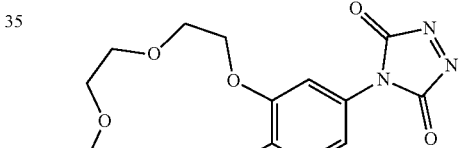

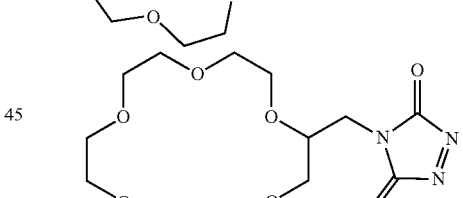

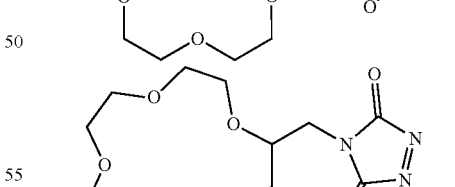

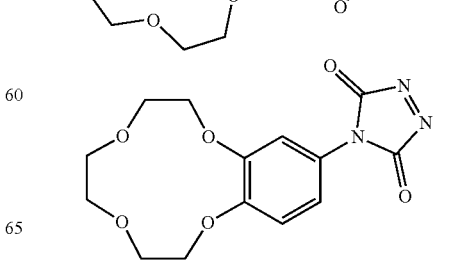

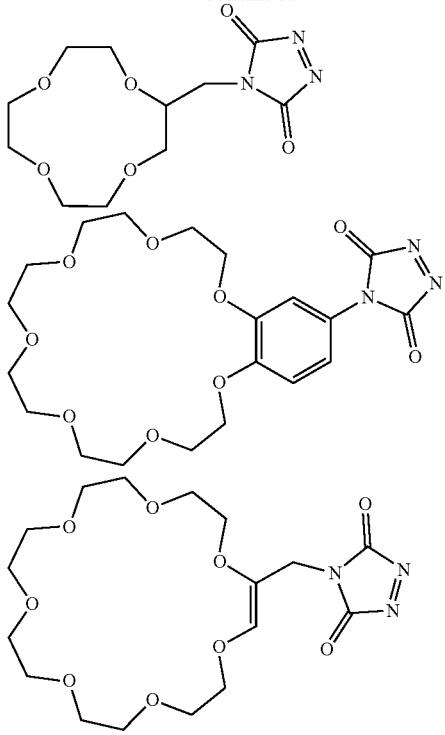
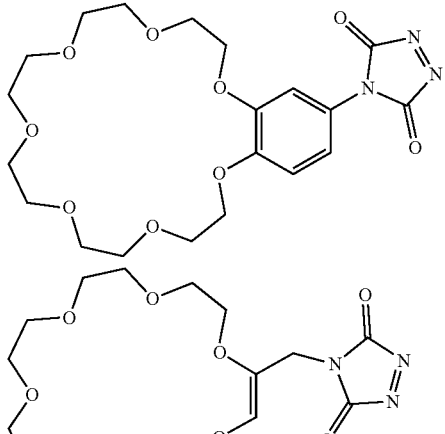
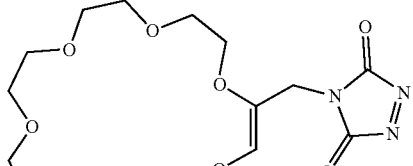

In one aspect, the derivatizing agent is MB409. In another embodiment, either the crown ether or the analyte may be further bound or connected to a 4-phenyl-1,2,4-triazoline-3,5-dione (PTAD) moiety, or a 1,2,4-triazoline-3,5-dione (TAD) moiety. For instance, when bound to vitamin D, PTAD creates two epimers by reacting with the s-cis-diene moiety of vitamin D.

Crown ether derivatising agents suitable for derivatizing aldehydes and ketones (such as testosterone and many of the ketone and aldehyde containing steroids) include without limitation, crown ethers bound to alkoxylamines and hydrazides. In one embodiment, the derivatizing agent having a crown ether bound to an alkoxylamine or hydrazide, includes, without limitation any of the structures of Group III:

Group III

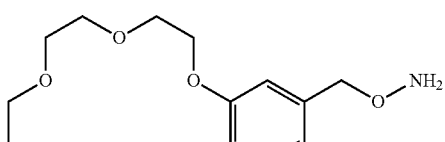
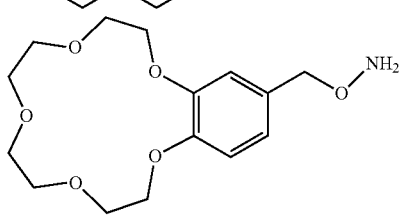
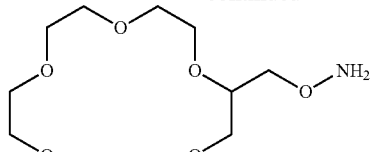
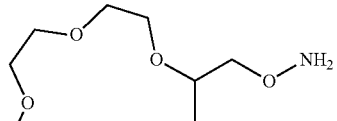
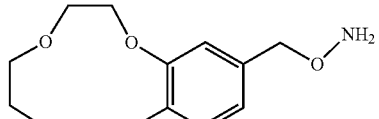
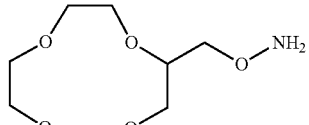
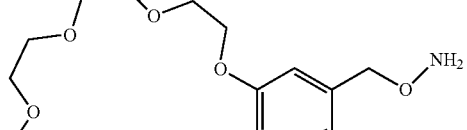
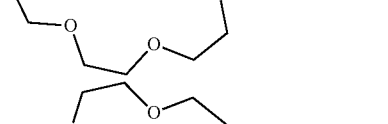
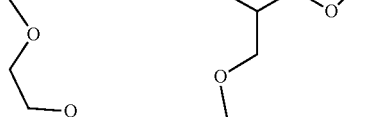
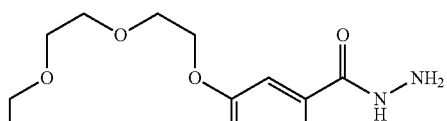
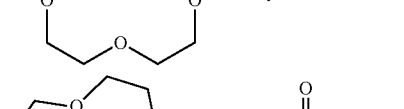
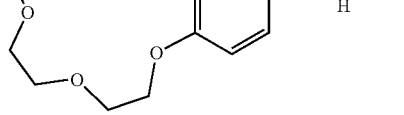

17
-continued
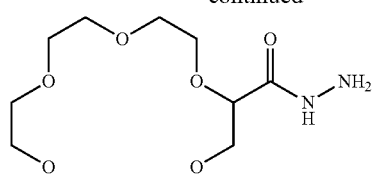
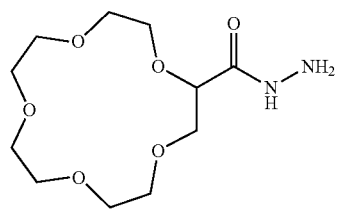
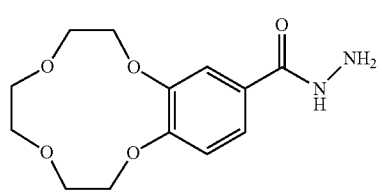
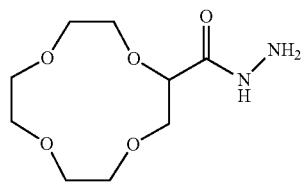
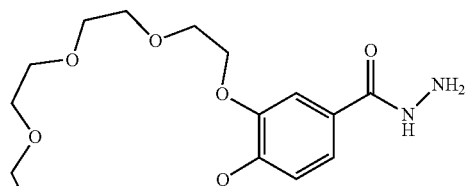
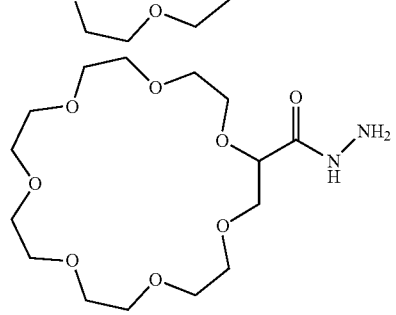
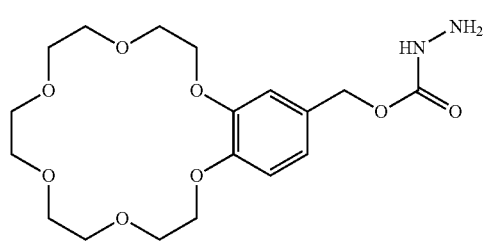
18
-continued
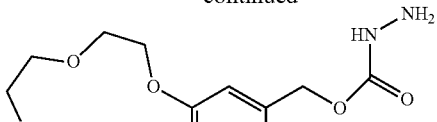
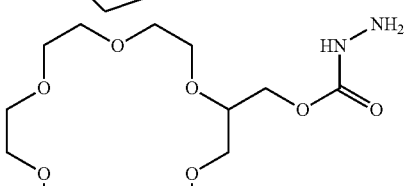
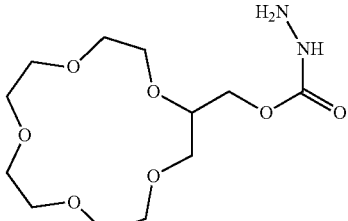
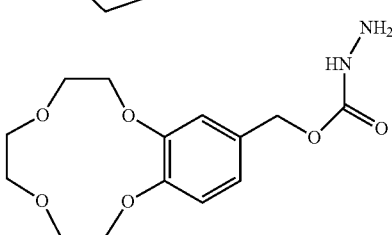
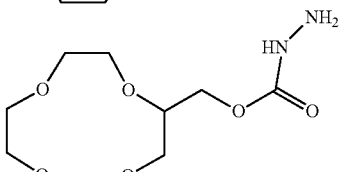
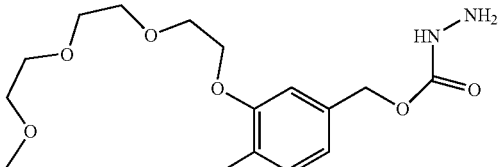
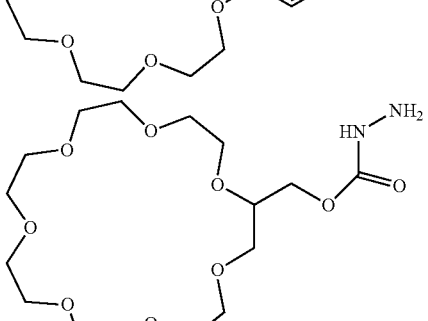
Crown ether derivatizing agents suitable for derivatizing carboxylic acids (such as aliphatic acids, biotin, monomethyl malonic acid (MMA), etc.) include without limitation, crown ethers bound to alcohols or amines. In one embodiment, the derivatising agent is a crown ether bound to an alcohol or amine, which includes, without limitation any of the structures of Group IV:
Group IV
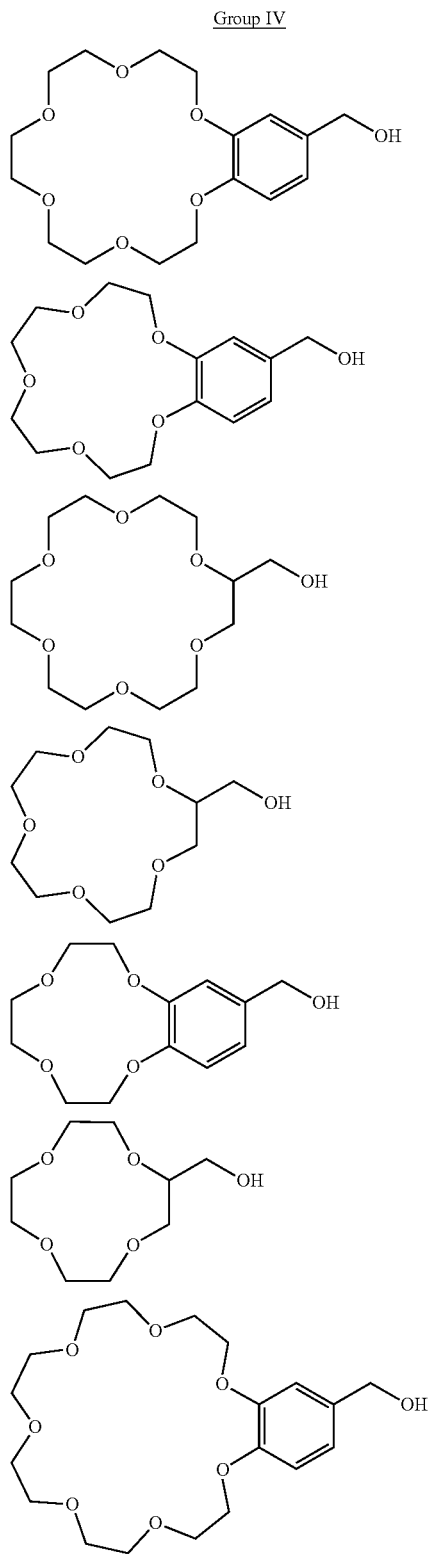
-continued
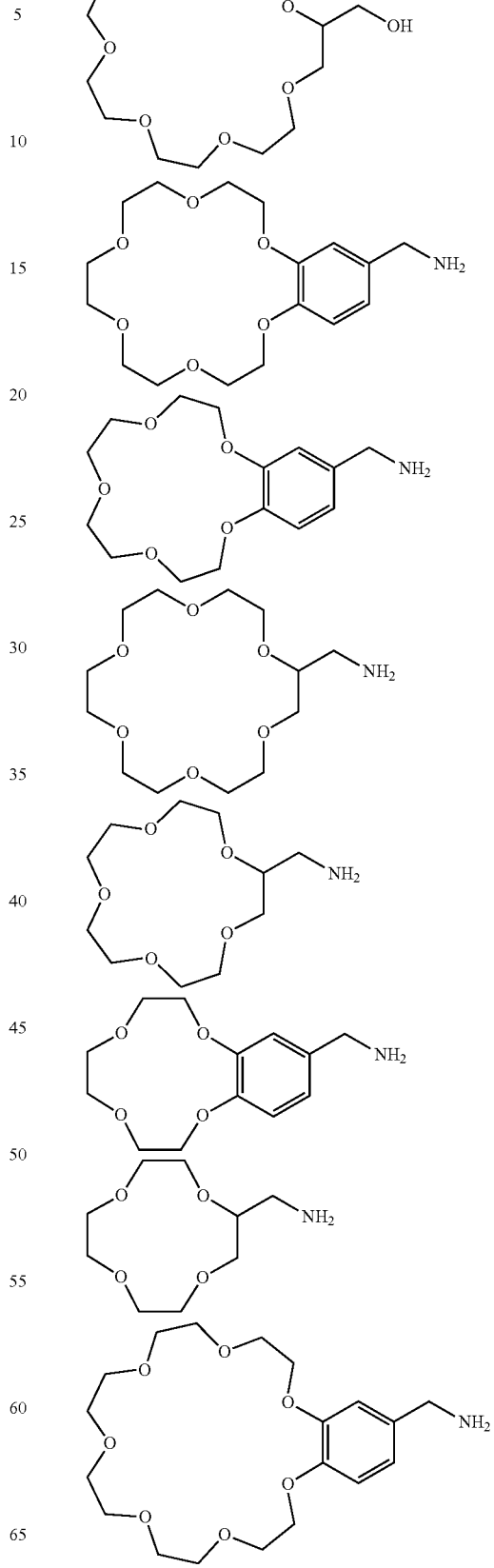

-continued

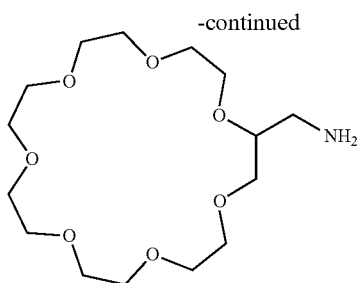

The crown ethers serve as a mass spectrometry sensitivity enhancer by trapping a cation. Cations of interest include, without limitation, NH4+, H3O+, MeNH3+, Na+, K+, or Ca2+. Different crown ethers have different affinities to different cations based on the size and shape of the crown ether.

In situ derivatization is performed either just before elution, during elution, or right after elution, or from just before the elution continued until after the elution, from the solid phase extraction column.

The elution may be performed with a high pH elution solution. As used herein, "high pH" includes elution solutions having a basic pH. In an aspect of this embodiment, an elution solution may have a pH of, e.g., about 8, about 8.5, about 9, about 9.5, about 10, about 10.5, about 11, about 11.5, about 12, about 12.5, or about 13. In other aspect of this embodiment, an elution solution may have a pH of, e.g., at least 8, at least 8.5, at least 9, at least 9.5, at least 10, at least 10.5, at least 11, at least 11.5, at least 12, at least 12.5, or at least 13. In yet other aspect of this embodiment, an elution solution may have a pH of, e.g., at most 8, at most 8.5, at most 9, at most 9.5, at most 10, at most 10.5, at most 11, at most 11.5, at most 12, at most 12.5, or at most 13. In yet other aspect of this embodiment, an elution solution may have a pH in the range of, e.g., about 8 to about 9, about 8 to about 9.5, about 8 to about 10, about 8 to about 10.5, about 8 to about 11, about 8 to about 11.5, about 8 to about 12, about 8 to about 12.5, about 8 to about 13, about 8.5 to about 9, about 8.5 to about 9.5, about 8.5 to about 10, about 8.5 to about 10.5, about 8.5 to about 11, about 8.5 to about 11.5, about 8.5 to about 12, about 8.5 to about 12.5, about 8.5 to about 13, about 9 to about 9.5, about 9 to about 10, about 9 to about 10.5, about 9 to about 11, about 9 to about 11.5, about 9 to about 12, about 9 to about 12.5, about 9 to about 13, about 9.5 to about 10, about 9.5 to about 10.5, about 9.5 to about 11, about 9.5 to about 11.5, about 9.5 to about 12, about 9.5 to about 12.5, about 9.5 to about 13, about 10 to about 10.5, about 10 to about 11, about 10 to about 11.5, about 10 to about 12, about 10 to about 12.5, about 10 to about 13, about 10.5 to about 11, about 10.5 to about 11.5, about 10.5 to about 12, about 10.5 to about 12.5, about 10.5 to about 13, about 11 to about 11.5, about 11 to about 12, about 11 to about 12.5, or about 11 to about 13.

An elution solution disclosed herein may be buffered using any buffer having an alkaline buffering capacity. In aspects of this embodiment, an elution solution disclosed herein may be buffered using one or a mixture of the organic or inorganic buffering agents, e.g., POPSO, TEA, phosphate. In other aspects of this embodiment, an elution solution disclosed herein may be buffered using, e.g., a trialkylammonium buffer comprising, e.g., trialkylammonium bicarbonate, trialkylammonium borate, trialkylammonium carbonate, or a trialkylammnium phosphate; a cesium buffer comprising, e.g., cesium bicarbonate, cesium borate, cesium carbonate, cesium hydroxide, or dibasic cesium phosphate, or tribasic cesium phosphate; a potassium buffer comprising, e.g., potassium bicarbonate, potassium borate, potassium carbonate, potassium hydroxide, or dibasic potassium phosphate, or tripotassium phosphate; a sodium buffer comprising, e.g., sodium bicarbonate, sodium borate, sodium carbonate, dibasic sodium phosphate, tribasic sodium phosphate, sodium hydroxide, or sodium tetraborate; a tetraalkylammonium buffer, comprising, e.g., tetraalkylammonium bicarbonate, tetraalkylammonium borate, tetraalkylammonium carbonate, or a tetraalkylammnium phosphate, in water, with or without the use of one of more of the following organic co-solvents such as acetonitrile, or acetone, or tetrohydrofuran (THF), or 1,4-dioxane, or dimehtylformamide (DMF), or N-methyl pyrrolidone (NMP), or dimethyl sulfoxide (DMSO), or hexamethylphosphoramide (HMPA), or diethyl ether, or isopropyl alcohol (IPA), or t-butanol, or 2-butanol, etc, in a desired ratio, such as at/below/or above, 5%, or 10%, or 15%, or 20%, or 25%, or 30%, or 35%, or 40%, or 45%, or 50%, or 55%, or 60%, or 70%, or 75%, or 80%, or 85%, or 90%, or 95%, of organic in water.

The amount of buffer used in an elution solution may be any concentration that can effectively maintain the alkaline buffering capacity of the buffer. In aspects of this embodiment, an effective concentration of buffer may be, e.g., about 1.0 mM, about 5.0 mM, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, or about 900 mM, or about 1 M. In other aspects of this embodiment, an effective concentration of buffer may be, e.g., at least 1.0 mM, at least 5.0 mM, at least 10 mM, at least 20 mM, at least 30 mM, at least 40 mM, at least 50 mM, at least 60 mM, at least 70 mM, at least 80 mM, at least 90 mM, at least 100 mM, at least 200 mM, at least 300 mM, at least 400 mM, at least 500 mM, at least 600 mM, at least 700 mM, at least 800 mM, or at least 900 mM, or at least 1 M. In yet other aspects of this embodiment, an effective concentration of buffer may be, e.g., at most 1.0 mM, at most 5.0 mM, at most 10 mM, at most 20 mM, at most 30 mM, at most 40 mM, at most 50 mM, at most 60 mM, at most 70 mM, at most 80 mM, at most 90 mM, at most 100 mM, at most 200 mM, at most 300 mM, at most 400 mM, at most 500 mM, at most 600 mM, at most 700 mM, at most 800 mM, or at most 900 mM, or at most 1 M.

In still other aspects of this embodiment, an effective concentration of elution buffer may be in the range of, e.g., about 0.1 mM to about 10 mM, about 0.1 mM to about 25 mM, about 0.1 mM to about 50 mM, about 0.1 mM to about 75 mM, about 0.1 mM to about 100 mM, about 0.1 mM to about 200 mM, about 0.1 mM to about 300 mM, about 0.1 mM to about 400 mM, about 0.1 mM to about 500 mM, about 0.1 mM to about 1000 mM, about 1 mM to about 10 mM, about 1 mM to about 25 mM, about 1 mM to about 50 mM, about 1 mM to about 75 mM, about 1 mM to about 100 mM, about 1 mM to about 200 mM, about 1 mM to about 300 mM, about 1 mM to about 400 mM, about 1 mM to about 500 mM, about 1 mM to about 1000 mM, about 5 mM to about 25 mM, about 5 mM to about 50 mM, about 5 mM to about 75 mM, about 5 mM to about 100 mM, about 5 mM to about 200 mM, about 5 mM to about 300 mM, about 5 mM to about 400 mM, about 5 mM to about 500 mM, about 5 mM to about 1000 mM, about 10 mM to about 25 mM, about 10 mM to about 50 mM, about 10 mM to about 75 mM, about 10 mM to about 100 mM, about 10 mM to about 200 mM, about 10 mM to about 300 mM, about 10 mM to about 400 mM, about 10 mM to about 500 mM, about 10 mM to about 1000 mM, about 25 mM to about 50 mM, about 25 mM to about 75 mM, about 25 mM to about 100 mM, about 25 mM to about 200 mM, about 25 mM to about 300 mM, about 25 mM to about 400 mM, about 25 mM to about 500 mM, about 25 mM to about 1000 mM, about 50 mM to about 75 mM, about 50 mM to about 100 mM, about 50 mM to about 200 mM, about 50 mM to about 300 mM, about 50 mM to about 400 mM, about 50 mM to about 500 mM, about 50 mM to about 1000 mM, about 75 mM to about 100 mM, about 75 mM to about 200 mM, about 75 mM to about 300 mM, about 75 mM to about 400 mM, about 75 mM to about 500 mM, about 75 mM to about 1000 mM, about 100 mM to about 150 mM, about 100 mM to about 200 mM, about 100 mM to about 300 mM, about 100 mM to about 400 mM, about 100 mM to about 500 mM, about 100 mM to about 1000 mM, about 200 mM to about 300 mM, about 200 mM to about 400 mM, about 200 mM to about 500 mM, about 200 mM to about 1000 mM, about 250 mM to about 300 mM, about 250 mM to about 400 mM, about 250 mM to about 500 mM, or about 250 mM to about 1000 mM. In another embodiment, an effective concentration of the elution buffer may be in the range of about 5 mM to about 250 mM.

An elution solution disclosed herein may comprise a derivatizing agent disclosed herein. The amount of derivatizing agent added to an elution solution disclosed herein is an amount in sufficient access to enable a complete derivatization of the analyte of interest for subsequent detection. The derivatizing agent may be mixed with the elution buffer prior to the elution as in an in situ derivatization process, it may also be added to the eluent right after the elution to fashion a post elution derivatization process.

In one embodiment, the simultaneous elution and derivatization of the analyte may be accomplished by applying to the analyte bound to a solid sorbent support matrix an elution buffer which includes a derivatizing agent. Upon application of the elution solution, a derivatization reaction occurs that converts the analyte to its derivative and then the derivative is eluted off the sorbent matrix at the same time as the elution of the analyte from the solid support matrix.

The derivatization reaction may be conducted under any condition suitable for the binding of the analyte. In one embodiment, a derivatization reaction is performed under temperature conditions suitable for the attachment of the derivatizing agent to the analyte. In aspects of this embodiment, a derivatization reaction may be performed at a temperature range from about or above 0° C. to about or below 100° C., more preferably from about 5° C. to about 90° C., more preferably from 10° C. to 80° C., more preferably from 15° C. to 70° C., more preferably from 18° C. to 60° C., more preferably from 18° C. to 40° C.

A derivatization reaction is performed under time conditions suitable for the attachment of the derivatizing agent to the analyte. In aspects of this embodiment, the derivatization reaction is performed at duration range from about 1 minute to about 24 hours, more preferably from about 3 minutes to about 5 hours, more preferably from about 5 minutes to about 60 minutes, more preferably from about 10 minutes to about 45 minutes. In one aspect the reaction ranges from about 15 minutes to about 30 minutes.

Of course, changing the temperature may change the reaction time. For instance, if the reaction is heated, for example, to 40° C., reaction time may be shortened.

The derivatization reaction may be quenched by addition of a buffered solution, which contains one or more of buffer agents. In one embodiment, the buffer is an ammonium buffer, such as ammonium formate, or ammonium acetate, or ammonium carbonate, ortriammonium phosphate, or ammonium sulfate, or ammonium borate, ammonium hydroxide, ammonium chloride, ammonium sulfate, ammonium bicarbonate, ammonium bisulfate, bisammonium phosphate, etc. In another embodiment, the quenching reagent may also be a buffered α-amino acid solution, such as glycine, alanine, or a buffered 3-alanine, or a buffered primary amine solution such as in a concentration range from 1 mM to 500 mM, in water, or a mixed solvent of water and an organic solvent, such as an alcohol, e.g., methanol, or ethanol, or propanol, or butanol, or glycol, or glycerol, or etc., or acetonitrile, or acetone, or ether, or THF, or 1,4-dioxanes, or DMF, or NMP, or DMSO, or HMPA. The quenching process neutralizes most of any excess derivatizing reagent that may remain in the eluent solution and also stabilizes the product by lowering the pH of the reaction mixture. In aspects of this embodiment, the pH of the eluent containing the derivatized analyte may be lowered to a range from about 4 to about 9.5.

Chromatography Analysis

After quenching, the reaction mixture containing derivatized analyte may then be directly analyzed for the presence of the analyte of interest. Such analysis may be either qualitative or quantitative in nature. In aspects of this embodiment, eluent containing derivatized analyte may be directly analyzed for the presence of the analyte of interest using, e.g., chromatography and/or mass spectroscopic detection.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), ultra-high pressure liquid chromatography (UHPLC), and turbulent flow liquid chromatography (TFLC) (sometimes known as high turbulence liquid chromatography) (HTLC) or high throughput liquid chromatography, or nano-flow liquid chromatography, or nano LC As used herein, the term "high performance liquid chromatography" or "HPLC" refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography (HTLC) or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC.

Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., Turbulent Flow Analysis Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with the analytes of interest. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded, a cyano bonded, or a pentafluorophenylpropyl (F5) surface, or phenyl/bonded, or biphenyl bonded surface. Alkyl bonded surfaces may include C-4, C-8, C-12, or C-18 bonded alkyl groups. In preferred embodiments, the column is a C-18 column. The chromatographic column includes an inlet port for receiving a sample directly or indirectly from a solid-phase extraction or HTLC column and an outlet port for discharging an effluent that includes the fractionated sample.

In certain embodiments, an analyte may be enriched in a sample by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be enriched in a sample by applying a sample to a column under mobile phase conditions where the analyte of interest elutes at a differential rate in comparison to one or more other materials. Such procedures may enrich the amount of one or more analytes of interest relative to one or more other components of the sample. In another embodiment, the reaction mixture of the analyte may be first loaded onto a guard column with a weak solvent to retain the desired analyte product on the guard column, then an LC elution solvent is to carry the substrate onto the analytical column for separation and analysis.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In one preferred embodiment, HPLC is conducted with a hydrophobic column chromatographic system. In certain preferred embodiments, a C18 analytical column (e.g., a TARGA® C18, 3 μm 50×2.1, or equivalent) is used. In certain preferred embodiments, HPLC are performed using HPLC Grade 5.0 mM ammonium formate with 0.1% formic acid at a pH of 3.0 and 0.1% formic acid in acetonitrile as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, the solid phase extraction may be used in a high throughput platform for enrichment of the derivatized analyte of interest prior to mass spectrometry. In such embodiments, samples may be extracted using a high throughput SPE cartridge, or a guard column which captures the derivatized analyte, then eluted onto an analytical HPLC column, such as a C-18 column, prior to mass spectrometry (MS) analysis. Because the steps involved in these chromatography procedures may be linked in an automated fashion, the requirement for operator involvement during the purification of the analyte can be minimized. This feature may result in savings of time and costs, and eliminate or reduce the opportunity for an operator error.

Direct Quantification

Direct quantification is "inline" or "on-line" use of the extracted and derivatized analyte for quantification. As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "sample injection" refers to introducing an aliquot of a single sample into an analytical instrument, for example a mass spectrometer. This introduction may occur directly or indirectly. An indirect sample injection may be accomplished, for example, by injecting an aliquot of a sample into a HPLC column that is connected to a mass spectrometer in an on-line fashion.

As used herein, the term "same sample injection" with respect to multiple analyte analysis by mass spectrometry means that the molecular ions for two or more different analytes are determined essentially simultaneously by measuring molecular ions for the different analytes from the same (i.e. identical) sample injection.

Mass Spectrometry

In various embodiments, the analytes of interest present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which may be heated to prevent condensation and to facilitate solvent evaporation. As the droplets get smaller the electrical surface charge density increases until such time that the natural repulsion between like charges causes ions as well as neutral molecules to be released. In one embodiment, the detection is performed after ESI.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counter flow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Anal. Chem. 2000, 72(15): 3653-3659.

As used herein, the term "desorption" refers to translocation of an analyte from a liquid surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS filter and detector (quadrupole). By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g. m/z: 5-1250 for API 5000) The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, one or more internal standards may be used to generate standard curves for calculating the quantity of the analytes of interest. Methods of generating and using such standard curves are well known in the art and one of ordinary skill is capable of selecting appropriate internal standards. For example, an isotopically labeled analyte may be used as an internal standard; in certain preferred embodiments, D6-25 OH vitamin $D_3$, D6-25-OH Vitamin $D_2$, D6-1,25(OH)$_2$ vitamin $D_3$, D6-1,25 (OH)$_2$ vitamin $D_2$ etc., may be used as internal standards. Numerous other methods for relating the amount of an ion to the amount of the original molecule will be well known to those of ordinary skill in the art.

In particularly preferred embodiments, the analytes of interest are quantified in a sample using MS/MS as follows. One or more of the analytes of interest in samples are first filtered through and eluted from a solid phase extraction column at a high pH in the presence of FMOC-Cl or a variant thereof. The resulting eluent is then subjected to liquid chromatography, preferably HPLC. The flow mobile phase from the chromatographic column enters the heated ESI probe of an MS/MS analyzer and the analytes ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios the analytes of interest. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD), or collision induced dissociation (CID). The fragment ions generated are passed into quadrupole 3 (Q3), where the fragment ions are selected while other ions are eliminated. During analysis of a single sample, Q1 and/or Q3 may be adjusted such that mass/charge ratios of one or more precursor ion/fragment ion pairs specific to one specific analyte is first selected, followed at some later time by the selection of mass/charge ratios of one or more precursor ion/fragment ion pairs specific to a second specific analyte, optionally followed at some later time by the selection of mass/charge ratios of one or more precursor ion/fragment ion pairs specific to a third specific analyte and so on. In particularly preferred embodiments, mass to charge ratios of precursor/fragment ion pairs specific to epinephrine, mass to charge ratios of precursor/fragment ion pairs specific to norepinephrine, mass to charge ratios of precursor/fragment ion pairs specific to the analyte are detected during analysis of a single sample, although the sequence of detection may occur in any order.

The methods may involve MS/MS performed in either positive or negative ion mode; preferably positive ion mode. Using standard methods well known in the art, one of ordinary skill is capable of identifying one or more fragment ions of a particular precursor ion of the analyte of interest that may be used for selection in quadrupole 3 (Q3).

In various embodiments, the analyte of interest is subjected to a mass spectrometry for detection and quantification. A mass spectrometry technique may employ atmospheric pressure chemical ionization (APCI) or electrospray ionization (ESI) to generate charged ions. The analyte of interest can present as a proton adduct or a protonated molecular ion, i.e. [M+H]$^+$ in the mobile phase. The analyte can also be shown the ammonium adduct [M+NH$_4$]$^+$ as a molecular ion when abundant ammonium ion is present in the mobile phase, or other cation adduct when corresponding cations are present in the mobile phase. Different adducts are also possible and can be recognized by the skilled artisan, and are generally shown by [M+A+H]$^+$, where A is the adduct. The adducts may or may not be solvated. During the ionization process, the molecular ions are desorbed into the gaseous phase, and then focused into the mass spectrometer for analysis and detection. See U.S. Pat. No. 6,692,971 for more information on APCI, as it is known to those of skill of the art.

MS analysis can be done with a single mass analyzer such as a single quardrupole mass spectrometer (MS), or a tandem mass analyzer such as a triple quadrupole tandem mass spectrometer (MS/MS). In a tandem mass spectrometry mode, the first mass filter or quadrupole (Q1) can be tuned to select independently, one or more of the molecular ions of the analyte of interest and internal standards of choice. The molecular ions (precursor ions) can undergo collision-induced dissociation (CID) at second quadrupole (Q2) to produce fragment or product ions. The fragment ions can be detected and analyzed at the second mass filter at Q3. This process can be referred to as product optimization. The second mass filter is then tuned to selectively monitor one or more of the most abundant product ions produced from a particular molecular ion. This technique is called multiple reaction monitoring (MRM).

MRM transitions of precursor-product ion pairs can be monitored for the hormones estrone, estradiol and 17β-estradiol-2,3,4-$^{13}C_3$ with MB338 as follows:

TABLE 1

MRM Transitions for Hormones

| Compound | Polarity | Precursor m/z | Product m/z |
|---|---|---|---|
| Estrone MB338 | Positive | 626.46 | 338.8 |
| Estrone MB338 | Positive | 626.46 | 163 |
| Estradiol MB338 | Positive | 628.56 | 339.1 |
| Estradiol MB338 | Positive | 628.56 | 162.9 |
| Estriol MB338 | Positive | 644.28 | 339 |
| Estriol MB338 | Positive | 644.28 | 162.8 |
| 17β-estradiol-2,3,4-$^{13}C_3$ MB338 | Positive | 631.399 | 339 |
| 17β-estradiol-2,3,4-$^{13}C_3$ MB338 | Positive | 631.399 | 163 |
| 17β-estradiol-2,3,4-$^{13}C_3$ MB338 | Positive | 631.399 | 107 |

Molecular ions [M+NH$_4^+$] of crown ether derivatives of 1,25-dihydroxy-vitamin D and its derivatives may be identified as MRM transitions of precursor-product ion pair. Internal standards, such as deuterated analytes, can be applied in the methods described herein. In one embodiment, D6-25 OH vitamin D$_3$, D6-25-OH Vitamin D$_2$, D6-1, 25(OH)$_2$ vitamin D$_3$, D6-1,25(OH)$_2$ vitamin D$_2$ may be used.

Molecular ions [M+NH$_4^+$] of crown-ether derivatives of THC or HU210 with MB338 are shown at below as MRM transitions of precursor-product ion pair:

TABLE 2

MRM Transitions for THC and HU210

| Compound | Polarity | Precursor m/z | Product m/z |
|---|---|---|---|
| THC MB338 | Positive | 670 | 339 |
| THC MB338 | Positive | 670 | 163 |
| THC MB338 | Positive | 670 | 107 |
| THC d3 MB338 | Positive | 673 | 339 |
| THC d3 MB338 | Positive | 673 | 163 |
| THC d3 MB338 | Positive | 673 | 107 |
| HU210 MB338 | Positive | 742 | 337 |
| HU210 MB338 | Positive | 742 | 339 |
| HU210 MB338 | Positive | 742 | 163 |

The methods disclosed herein can be evaluated by several parameters including, e.g., accuracy, precision, limit of detection (LOD), limits of quantitation (LOQ), linear range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value. The limit of detection (LOD) of a method refers to the concentration of analyte which gives rise to a signal that is significantly different from the negative control or blank and represents the lowest concentration of analyte that can be distinguished from background.

The limits of quantitation (LOQ) are the lowest and the highest concentrations of analyte in a sample that can be measured with an acceptable level of accuracy and precision. The lower limit of quantitation refers to the lowest dose that a detection method can measure consistently from the background. The upper limit of quantitation is the highest dose that a detection method can measure consistently before saturation of the signal occurs. The linear range of the method is the area between the lower and the upper limits of quantitation. The linear range is calculated by subtracting lower limit of quantitation from the upper limit of quantitation. As used herein, the term "signal to noise ratio for the lower asymptote" refers to the signal detected in the method at the lower limit of detection divided by the background signal. As used herein, the term "signal to noise ratio for the upper asymptote" refers to the signal detected in the method at the upper limit of detection divided by the background signal.

As used herein, an "amount" of an analyte in a body fluid sample refers generally to an absolute value reflecting the mass of the analyte detectable in volume of body fluid. However, an amount also contemplates a relative amount in comparison to another analyte amount. For example, an amount of analyte in a body fluid can be an amount which is greater than a control or normal level of analyte normally present.

The present methods, reagents, and kits may be used for the quantification or the detection of an analyte of interest.

Embodiments Section

Embodiment 1 is a method for determining the presence of one or more analytes in a test sample, the method comprising:
  a) extraction and purification of the analytes from the test sample with one or more of solid phase extraction, supported liquid extraction (SLP), and liquid liquid extraction (LLP);
  b) derivatization of the analytes with a crown-ether derivatizing agent;
  c) detection of the derivatized analytes using liquid chromatography and/or mass spectrometry.

In an aspect of Embodiment 1, the analyte is a compound having a primary amine or a phenolic hydroxyl group. In a further aspect, the analyte is a drug, a hormone, a signaling agent, an amino acid, or a pesticide. In a particular aspect, the analyte is a monoamine neurotransmitter including vitamin D or one of its derivatives or metabolites, a sex hormone or one of its derivatives or metabolites, a cannabinoid or one of its derivatives or metabolites, an opiate, opioid or one of its derivatives or metabolites or an arylcyclohexylamine or one of its derivatives or metabolites, an Amphetamine or one of its derivatives or metabolites. For instance, the monoamine neurotransmitter is Histamine, Tryptamine, Serotonin, or Agmatine. Similarly the sex hormone or one of its derivatives or metabolites is an estrogen. Further, the derivative of vitamin D is 25-OH D$_3$, 25-OH D$_2$, 24,25-(OH)$_2$D$_3$, 1,25-(OH)$_2$D$_3$, and 1,25-(OH)$_2$D$_2$, Cholecalciferol, 25-Hydroxycholecalciferol, 1α,25-Dihydroxycholecalciferol, Ergocalciferol, 1α,25-Dihydroxyergocalciferol, 22,23-Dihydroergocalciferol, 1α,24R,25-Trihydroxycholecalciferol, (6Z)-tacalciol, Tachysterol$_3$, Isovitamin D$_3$, Dihydrotachysterol$_3$.

In yet another aspect of Embodiment 1, the cannabinoid or one of its derivatives or metabolites is a Cannabigerol-type (CBG) cannabinoid, a Cannabichromene-type (CBC) cannabinoid, a Cannabidiol-type (CBD) cannabinoid, a Cannabinodiol-type (CBND) cannabinoid, a Tetrahydrocannabinol-type (THC) cannabinoid, a Cannabinol-type (CBN) cannabinoid, a Cannabitriol-type (CBT) cannabinoid, a Cannabielsoin-type (CBE) cannabinoid, an Isocannabinoid, a Cannabicyclol-type (CBL) cannabinoid, a Cannabicitran-type (CBT) cannabinoid, or a Cannabichromanone-type (CBCN) cannabinoid. Similarly, the opiate, the opioid or the derivative or metabolite of the opiate or opioid, is morphine, oripavine, morphinone, hydromorphone, or oxymorphone. In a particular aspect, the opiate, the opioid, or the derivative or metabolite of the opiate or opioid is a benzylisoquinoline alkaloid, a semi-synthetic benzylisoquinoline alkaloid derivative, or an opioid.

In yet another aspect, the arylcyclohexylamine or one of its derivatives or metabolites is Tiletamine, 3-Methoxetamine (MXE), Methoxyketamine, N-Ethylnorletamine (Ethketamine), Amphetamine, Ephedrine, or Methamphetamine.

In an even further aspect, the Amphetamine or one of its derivatives or metabolites is Amphetamine (itself), methamphetamine, ephedrine, cathinone, 3,4-methylenedioxy-N-methylamphetamine (MDMA, "Ecstasy"), and 2,5-Dimethoxy-4-methylamphetarnine (DOM, or "STP").

In a particular aspect of Embodiment 1, the solid phase extraction is performed with an ion exchange column or cartridge. For instance in one particular aspect, the ion exchange column is a cation exchange column. For instance, the cation exchange column may be a weak cation exchange column. In another particular aspect, the ion exchange column is an anion exchange column. In yet another aspect, the solid phase extraction is performed with a reverse phase silica column or cartridge. For instance, the reverse phase silica may be an alkyl bounded (C4, C8, C12, or C18) silica, a cyano bounded silica, a phenyl bounded silica, or a biphenyl bounded silica.

In embodiment 1, the sample may be biological sample, a soil sample, or a sample of food stuff. In one particular aspect, the biological sample is a blood sample, a saliva sample, a lachrymal sample, a urine sample, or a tissue sample. For instance, the blood sample may be a full blood sample, a plasma sample, or a serum sample.

In a second embodiment, the present invention is directed to a derivatization reagent having a derivatizing agent. In one aspect, the crown ether derivatizing agent comprises: a crown-ether, a connector, and an analyte-binding functional group. In one particular aspect the crown-ether comprises a ring, and the ring is a 12-30 membered ring. In a further aspect, the ring has 12-30 member atoms of which 8-20 atoms are Carbon. In yet a further aspect, the non-carbon member atoms are selected from oxygen, nitrogen, and sulfur. In a particular aspect, the crown ether is selected from 12 Crown 4, 15 Crown 5, 16 crown 4, 18 Crown 6, 21 Crown 7, or 24 Crown 8, optionally having one or more heteroatoms replacing oxygen.

In one particular aspect, the connector is a $C_1$-$C_{12}$ linear, branched, and/or cyclic alkyl group, and even further, the connector may be a phenolic ring fused to the crown ether.

In a particular aspect of embodiment 1, the analyte binding group is an acylating group, 4-Phenyl-1,2,4-triazolin-3,5-dione (PTAD), 1,2,4-traizoline-3,5-dione (TAD), an Alkoxylamine, a hydrazide, an alcohol, or an amine. For instance, in one particular aspect the acylating group is an acylating agent of Formula 2:

Formula 2 wherein A is the analyte and X is the connector. For instance, in a particular aspect the analyte binding group is an acylating agent that is an acyl chloride or acyl halide.

In one particular aspect the crown ether derivatizing agent is selected from the reagents of Group I (laid forth above). In one aspect, the derivatizing agent is MB338. In another aspect, the derivatizing agent is selected from the agents of Group II (laid forth above). In one aspect, the derivatizing agent MB409. In yet another aspect, the derivatizing agent is selected from the agents of Group III. In still a further aspect, the derivatizing agent is selected from the agents of Group IV.

However, any of the derivatizing agents may be incorporated into a derivatizing reagent and/or used in the methods of the first embodiment.

In particular, where the analyte of embodiment 1 has a primary and secondary amine, aliphatic hydroxyl, or phenolic hydroxyl group, an acylating agent may be used. In one aspect, the acylating agent is an acyl chloride or acyl halide. In one particular aspect the crown ether derivatizing agent is selected from the reagents of Group I (laid forth above). In one aspect, the derivatizing agent is MB338. In a further aspect, the acylating agent may be used when the anaylte is an amino acid or a metabolite or derivative thereof, an estrogen hormone or a metabolite or derivative thereof, THC or a metabolite or analog thereof or HU210 or a metabolite or derivative thereof.

Further, when the analyte has a ci-diene group, the crown ether derivatizing agent may be selected from the reagents of Group II (laid forth above). In one particular aspect the derivatizing agent is MB409. In one aspect, the analyte may be vitamin D, an analog thereof, or a metabolite thereof as more fully denoted above.

Even further, when the analyte has an aldehyde or ketone the crown ether derivatizing agent may be selected from the agents of Group III (laid forth above). In one particular aspect, the analyte is testosterone or a metabolite thereof, or a ketone or aldehyde containing steroid.

When the analyte is an aliphatic acid, biotin or monomethyl malonic acid (MMA) the crown ether derivatizing agent may be selected from the agents of Group IV (laid forth above).

In yet a further embodiment, the derivatising agent is incorporated into a derivatization reagent by the addition of one or more solvents or additives, which may then be incorporated into a kit for analysis of one or more particular analytes.

In another embodiment, the mass spectrometry comprises tandem mass spectrometry techniques, including LC-MS/MS techniques such as Atmospheric Pressure Chemical Ionization (APCI), Electrospray Ionization (ESI) technique, the use of a triple quadrupole mass spectrometer instrument in Multiple Reaction Monitoring (MRM), or Selected Reaction Monitoring (SRM), positive-ion mode, a Q1 scan tuned to select a precursor ion that corresponds to the $[M+H]^+$, or $[M+NH_4]^+$, or $[M+A+H]^+$ of the acylated derivatives of the desired analyte for product optimization, wherein A is a molecular adduct. The detection of the analyte can be qualitative or quantitative.

Aspects of the present specification can also be described as follows:

1. A method for determining the presence of one or more analytes in a test sample, the method comprising:
    a) extraction and purification of the analytes from the test sample with one or more of solid phase extraction, supported liquid extraction (SLP), and liquid liquid extraction (LLP);
    b) derivatization of the analytes with a crown-ether derivatizing agent;
    c) detection of the derivatized analytes using liquid chromatography and/or mass spectrometry.
2. The method of embodiment 1, wherein the analyte is a compound having a primary amine or a phenolic hydroxyl group.
3. The method of embodiment 1 or 2, wherein the analyte is a drug, a hormone, a signaling agent, an amino acid, or a pesticide.
4. The method of embodiments 1-3, wherein the analyte is a monoamine neurotransmitter including vitamin D or one of its derivatives or metabolites, a sex hormone or one of its derivatives or metabolites, a cannabinoid or one of its derivatives or metabolites, an opiate, opioid or one of its derivatives or metabolites or an arylcyclohexylamine or one of its derivatives or metabolites, an Amphetamine or one of its derivatives or metabolites
5. The method of embodiment 4, wherein the monoamine neurotransmitter is Histamine, Tryptamine, Serotonin, or Agmatine.
6. The method of embodiment 4, wherein the sex hormone or one of its derivatives or metabolites is an estrogen.
7. The method of embodiment 4, wherein the derivative of vitamin D is 25-OH $D_3$, 25-OH $D_2$, 24,25-$(OH)_2D_3$, 1,25-$(OH)_2$ $D_3$, and 1,25-$(OH)_2$ $D_2$, Cholecalciferol, 25-Hydroxycholecalciferol, 1α,25-Dihydroxycholecalciferol, Ergocalciferol, 1α,25-Dihydroxyergocalciferol, 22,23-Dihydroergocalciferol, 1α,24R,25-Trihydroxycholecalciferol, (6Z)-tacalciol, Tachysterol$_3$, Isovitamin $D_3$, Dihydrotachysterol$_3$.
8. The method of embodiment 4, wherein the cannabinoid or one of its derivatives or metabolites is a Cannabigerol-type (CBG) cannabinoid, a Cannabichromene-type (CBC) cannabinoid, a Cannabidiol-type (CBD) cannabinoid, a Cannabinodiol-type (CBND) cannabinoid, a Tetrahydrocannabinol-type (THC) cannabinoid, a Cannabinol-type (CBN) cannabinoid, a Cannabitriol-type (CBT) cannabinoid, a Cannabielsoin-type (CBE) cannabinoid, an Isocannabinoid, a Cannabicyclol-type (CBL) cannabinoid, a Cannabicitran-type (CBT) cannabinoid, or a Cannabichromanone-type (CBCN) cannabinoid.
9. The method of embodiment 4, wherein the opiate, the opioid or the derivative or metabolite of the opiate or opioid, is morphine, oripavine, morphinone, hydromorphone, or oxymorphone.
10. The method of embodiment 4, wherein the opiate, the opioid, or the derivative or metabolite of the opiate or opioid is a benzylisoquinoline alkaloid, a semi-synthetic benzylisoquinoline alkaloid derivative, or an opioid.
11. The method of embodiment 4, wherein the arylcyclohexylamine or one of its derivatives or metabolites is Tiletamine, 3-Methoxetamine (MXE), Methoxyketamine, N-Ethylnorletamine (Ethketamine), Amphetamine, Ephedrine, or Methamphetamine.
12. The method of embodiment 4, wherein the Amphetamine or one of its derivatives or metabolites is Amphetamine (itself), methamphetamine, ephedrine, cathinone, 3,4-methylenedioxy-N-methylamphetamine (MDMA, "Ecstasy"), and 2,5-Dimethoxy-4-methylamphetamine (DOM, or "STP").
13. The method of embodiments 1-12, wherein the solid phase extraction is performed with an ion exchange column or cartridge.
14. The method of embodiment 13, wherein the ion exchange column is a cation exchange column.
15. The method of embodiment 14, wherein the cation exchange column is a weak cation exchange column.
16. The method of embodiment 13, wherein the ion exchange column is an anion exchange column.
17. The method of embodiments 1-13, wherein the solid phase extraction is performed with a reverse phase silica column or cartridge.
18. The method of embodiment 17, wherein the reverse phase silica is an alkyl bounded (C4, C8, C12, or C18) silica, a cyano bounded silica, a phenyl bounded silica, or a biphenyl bounded silica.
19. The method of embodiments 1-18, wherein the sample is a biological sample, a soil sample, or a sample of food stuff.
20. The method of embodiment 19, wherein the biological sample is a blood sample, a saliva sample, a lachrymal sample, a urine sample, or a tissue sample.
21. The method of embodiment 20, wherein the blood sample is a full blood sample, a plasma sample, or a serum sample.
22. The method of embodiments 1-21, wherein the crown-ether derivatizing agent comprises: a crown-ether, a connector, and an analyte-binding functional group.
23. The method of embodiment 22, wherein the crown-ether comprises a ring, and the ring is a 12-30 membered ring.
24. The method of embodiment 23, wherein the ring has 12-30 member atoms of which 8-20 atoms are carbon.
25. The method of embodiment 24, wherein the non-carbon member atoms are selected from oxygen, nitrogen, and sulfur.
26. The method of embodiment 25, wherein the crown ether is selected from 12 Crown 4, 15 Crown 5, 16 crown 4, 18 Crown 6, 21 Crown 7, or 24 Crown 8, optionally having one or more heteroatoms replacing oxygen.
27. The method of embodiments 22-26, wherein the connector is a $C_1$-$C_{12}$ linear, branched, and/or cyclic alkyl group.
28. The method of embodiments 22-27, wherein the connector is a phenolic ring fused to the crown ether.
29. The method of embodiments 22-28, wherein the analyte binding group is an acylating group, 4-Phenyl-1,2,4-triazolin-3,5-dione (PTAD), 1,2,4-traizoline-3,5-dione (TAD), an Alkoxylamine, a hydrazide, an alcohol, or an amine.
30. The method of any of embodiments 1-29, wherein the acylating group is an acylating agent of Formula 2:

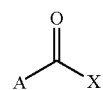

Formula 2 where A is the analyte and X is the connector.
31. The method of embodiment 30, wherein the acylating agent that is an acyl chloride or acyl halide.

32. The method of any of embodiments 1-31, where the crown ether derivatizing agent is selected from the agents of Group I:

Group I.

[Structures of crown ether derivatizing agents with acyl chloride (COCl) and Y-X functional groups]

OR

-continued

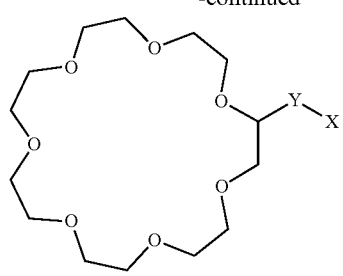

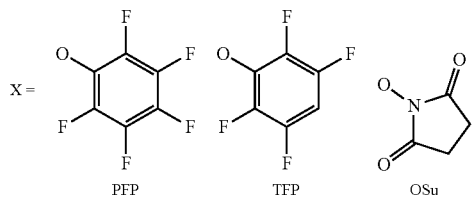

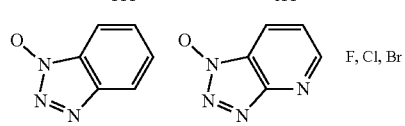

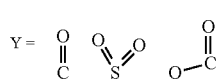

33. The method of any of embodiments 1-31, wherein the derivatizing agent is MB338.

34. The method of any of embodiments 30-33, wherein the analyte has a primary and secondary amine, aliphatic hydroxyl, or phenolic hydroxyl group.

35. The method of embodiment 34, wherein the analyte is an amino acid or a metabolite or derivative thereof, an estrogen hormone or a metabolite or derivative thereof, THC or a metabolite or analog thereof or HU210 or a metabolite or derivative thereof.

36. The method of any of embodiments 1-31, wherein the crown ether derivatizing agent is selected from the agents of Group II:

Group II

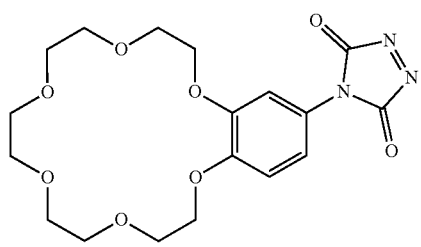

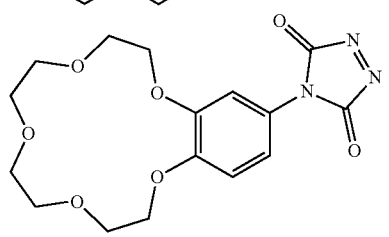

-continued

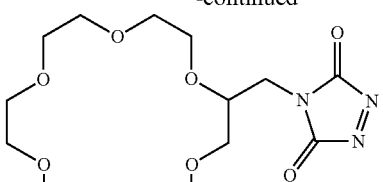

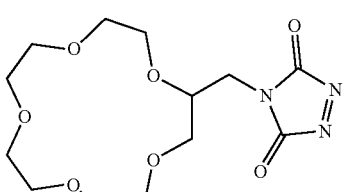

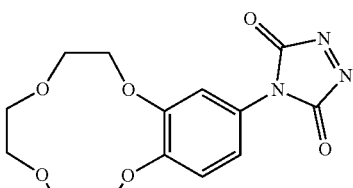

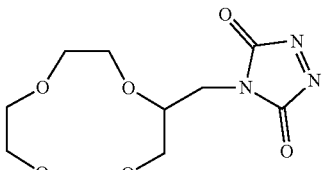

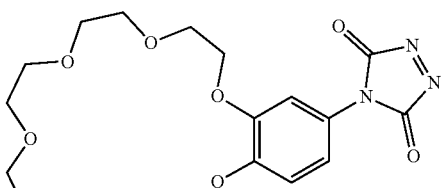

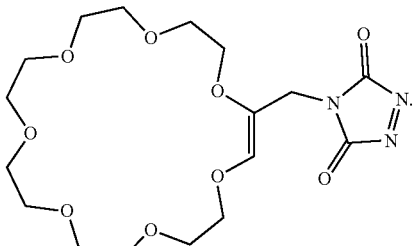

37. The method of any of embodiments 1-31, wherein the derivatizing agent is MB409.

38. The method of embodiment 36 or embodiment 37, wherein the analyte has a ci-diene group. PP-31,1

39. The method of embodiment 38, wherein the analyte is vitamin D, an analog thereof, or a metabolite thereof.

40. The method of any of embodiments 1-31, wherein the derivatizing agent is selected from the agents of Group III:

Group III.
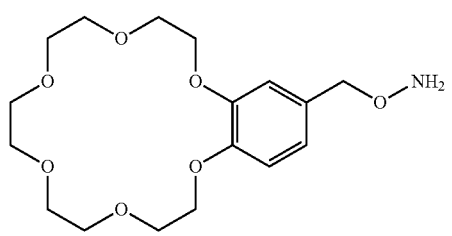
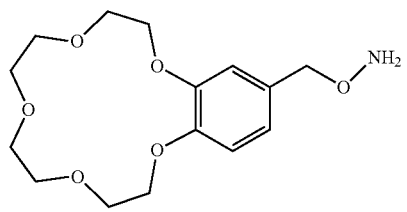
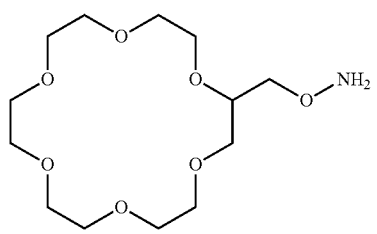
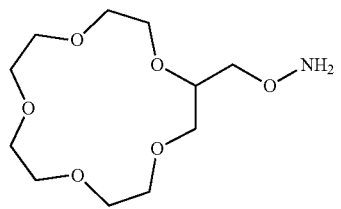
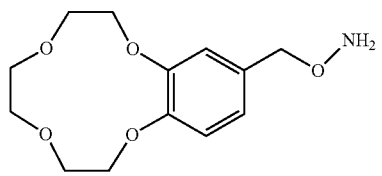
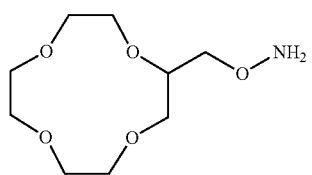
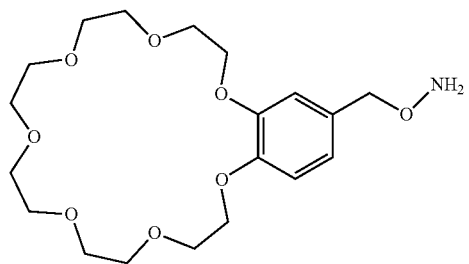
-continued
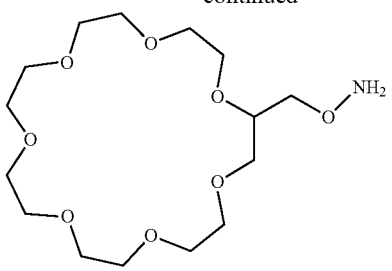
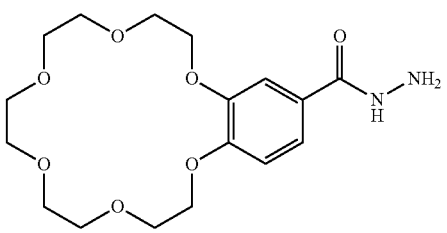
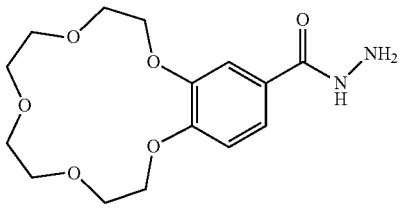
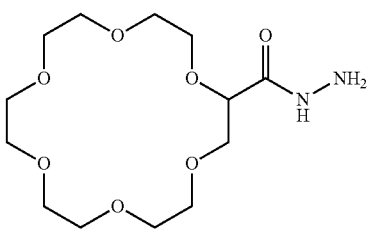
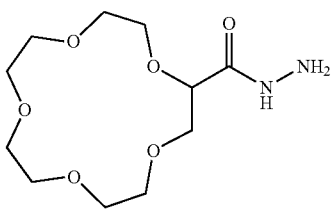
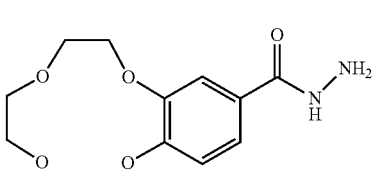
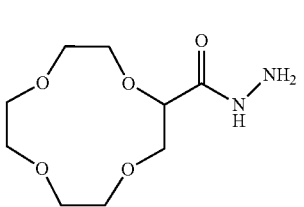

-continued
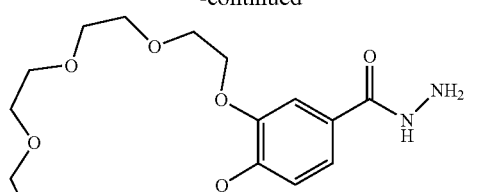
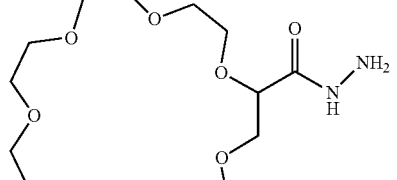
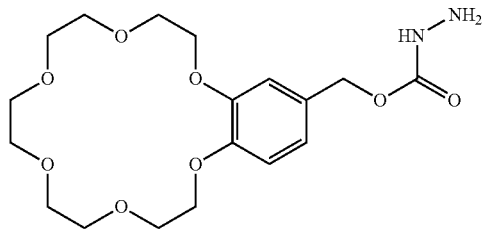
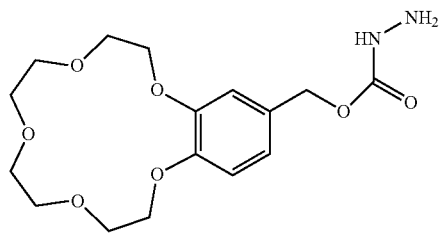
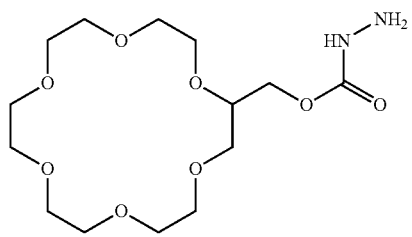
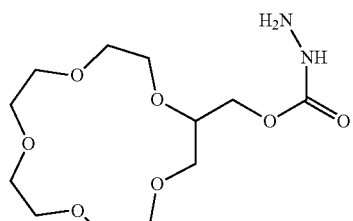
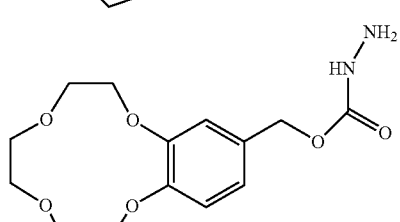
-continued
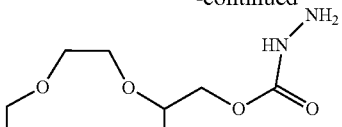
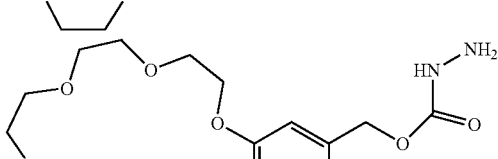
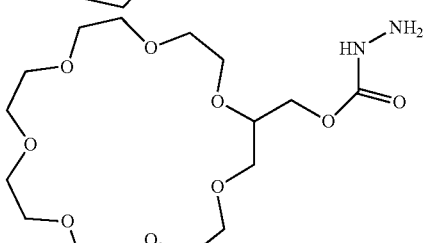
41. The method of embodiment 40, wherein the analyte has an aldehyde or ketone.
42. The method of embodiment 41, wherein the analyte is testosterone or a metabolite thereof, or a ketone or aldehyde containing steroid.
43. The method of any of embodiments 1-31, wherein the crown ether derivatizing agent is selected from the agents of group IV:
Group IV.
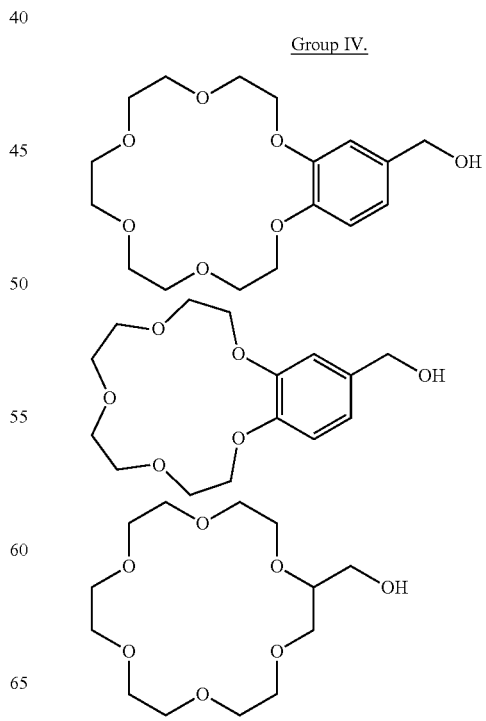

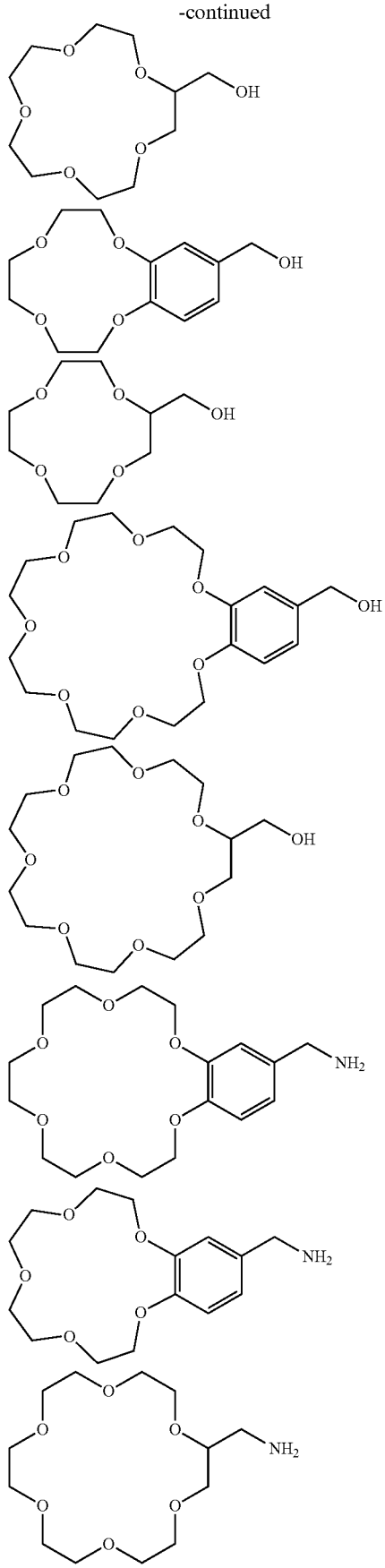
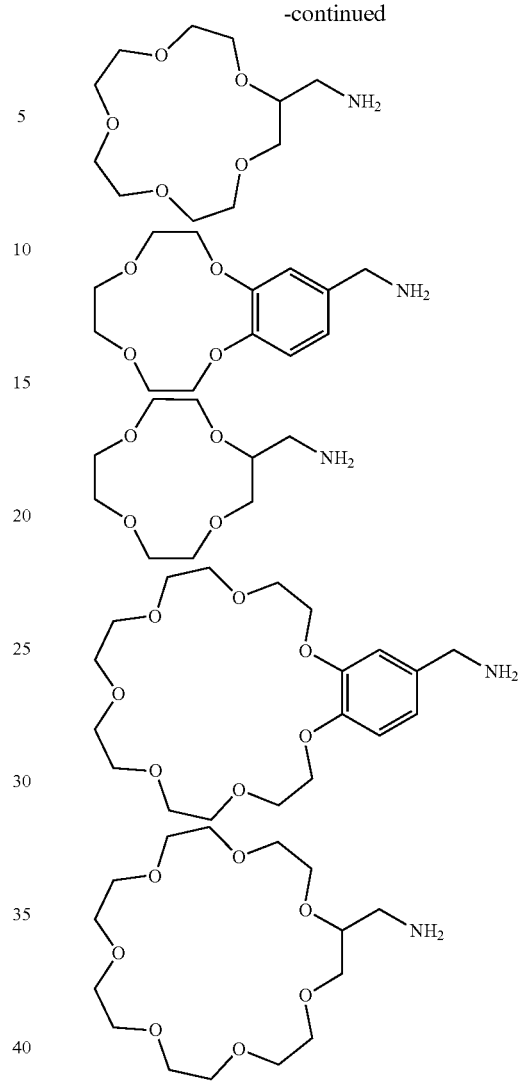

44. The method of embodiment 43, wherein the analyte is an aliphatic acid, biotin or monomethyl malonic acid (MMA).
45. The method of any of embodiments 1-4, wherein the mass spectrometry comprises tandem mass spectrometry techniques.
46. The method of any of embodiments 1-45, wherein the mass spectrometry comprises LC-MS/MS techniques.
47. The method of embodiment 46, wherein the LC-MS/MS techniques comprise Atmospheric Pressure Chemical Ionization (APCI), or Electrospray Ionization (ESI) technique.
48. The method of embodiment 46, wherein the LC-MS/MS techniques comprise the use of a triple quadrupole mass spectrometer instrument in Multiple Reaction Monitoring (MRM), or Selected Reaction Monitoring (SRM), positive-ion mode.
49. The method of embodiment 48, wherein the LC-MS/MS techniques comprise a Q1 scan tuned to select a precursor ion that corresponds to the $[M+H]^+$, or $[M+NH_4]^+$, or $[M+A+H]^+$ of the acylated derivatives of the desired analyte for product optimization, wherein A is a molecular adduct.
50. The method of any of embodiments 1-49, wherein the detection of the analyte is qualitative or quantitative.

51. A derivatization reagent for mass spectrometry having a derivatizing agent comprising: a crown-ether, a connector, and an analyte-binding functional group.
52. The derivatization reagent of embodiment 51, wherein the crown-ether comprises a ring, and the ring is a 12-30 membered ring.
53. The derivatization reagent of embodiment 52, wherein the ring has 12-30 member atoms of which 8-20 atoms are carbon.
54. The derivatization reagent of embodiment 53, wherein the non-carbon member atoms are selected from oxygen, nitrogen, and sulfur.
55. The derivatization reagent of any of embodiments 51-54, wherein the crown ether is selected from 12 Crown 4, 15 Crown 5, 16 crown 4, 18 Crown 6, 21 Crown 7, or 24 Crown 8, optionally having one or more heteroatoms replacing oxygen.
56. The derivatization reagent of any of embodiments 51-55, wherein the connector is a $C_1$-$C_{12}$ linear, branched, and/or cyclic alkyl group.
57. The derivatization reagent of any of embodiments 51-56, wherein the connector is a phenolic ring fused to the crown ether.
58. The derivatization reagent of any of embodiments 51-57, wherein the analyte binding group is an acylating group, 4-Phenyl-1,2,4-triazolin-3,5-dione (PTAD), 1,2,4-traizoline-3,5-dione (TAD), an Alkoxylamine, a hydrazide, an alcohol, or an amine.
59. The derivatization reagent of any of embodiments 51-58, wherein the acylating group is an acylating agent of Formula 2:

Formula 2 where A is the analyte and X is the connector.
60. The derivatization reagent of embodiment 59, wherein the acylating agent is an acyl chloride or acyl halide.
61. The derivatization reagent of any of embodiments 51-60, where the crown ether derivatizing agent is selected from the agents of Group I:

Group I.

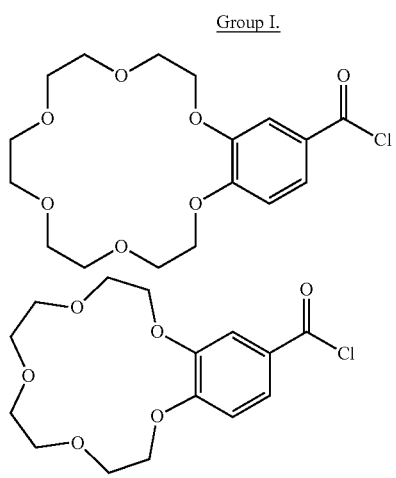

-continued

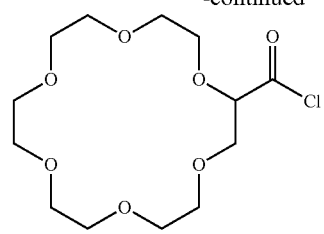

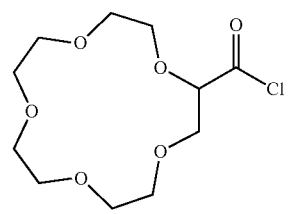

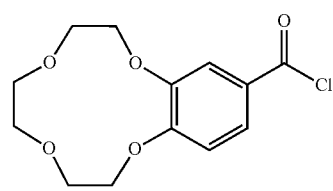

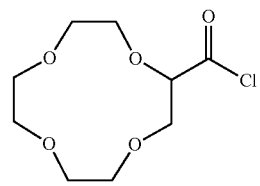

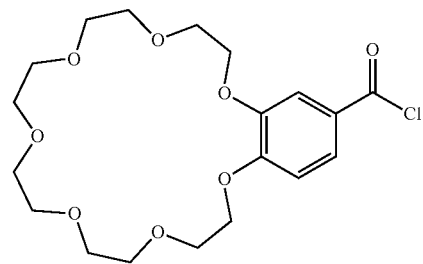

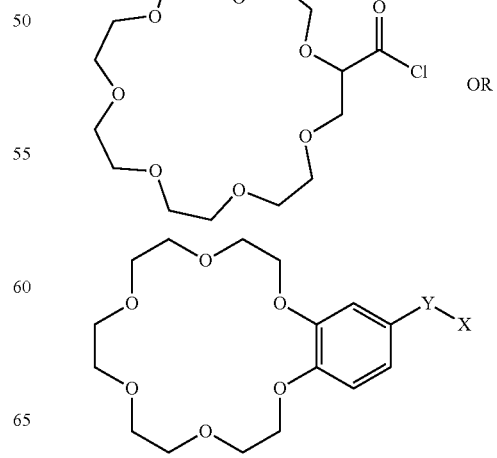

OR

49
-continued
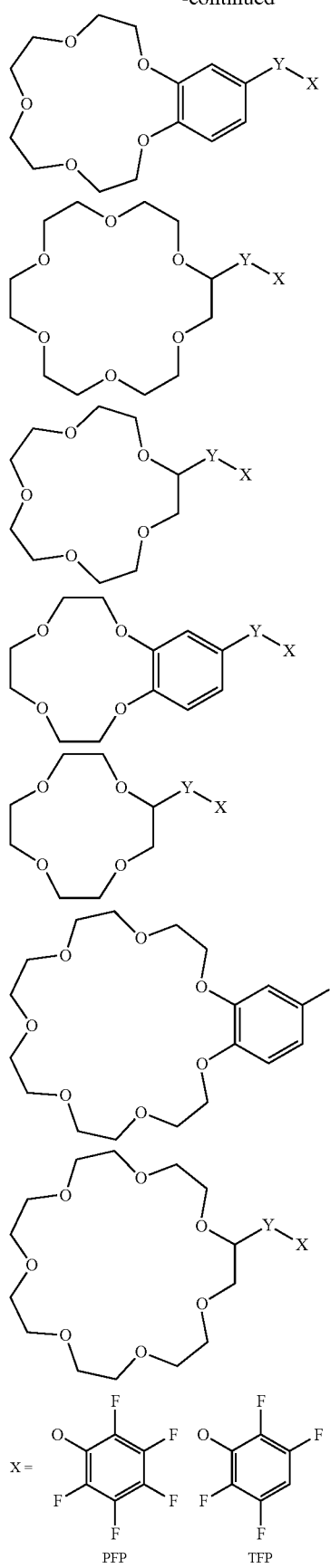
50
-continued
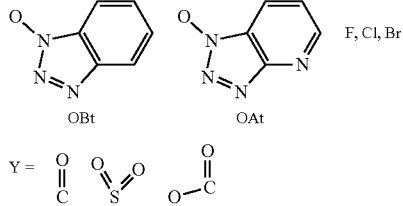
62. The derivatization reagent of any of embodiments 51-61, wherein the derivatizing agent is MB409.
63. The derivatization reagent of any of embodiments 51-61, wherein the crown ether derivatizing agent is selected from the agents of Group II:
Group II
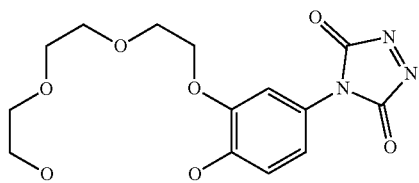
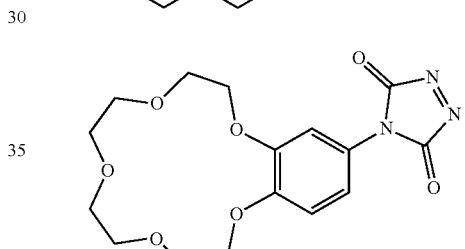
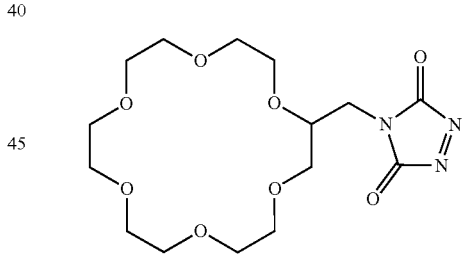
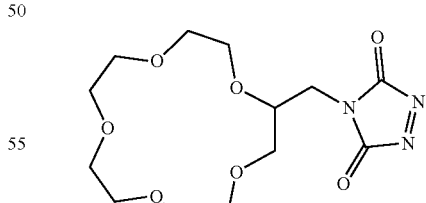
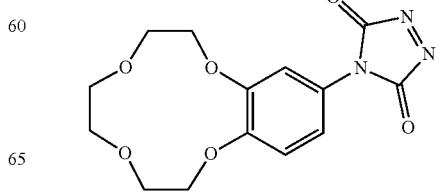

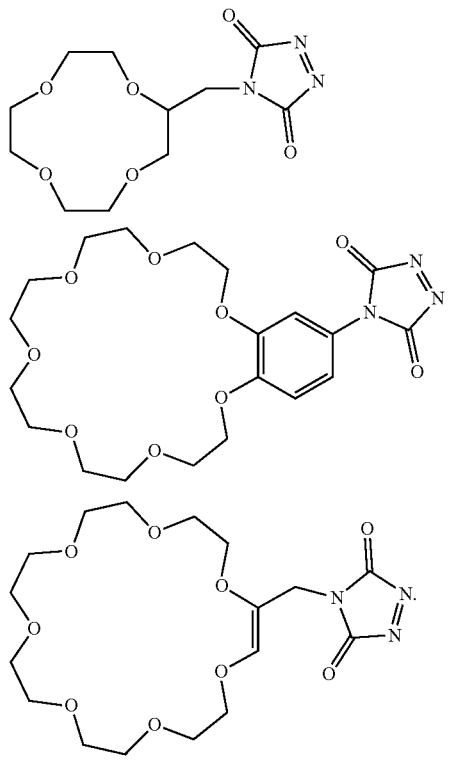
64. The derivatization reagent of any of embodiments 51-61, wherein the derivatizing agent is MB409.
65. The derivatization reagent of any of embodiments 51-60, wherein the derivatizing agent is selected from the agents of Group III:
Group III.
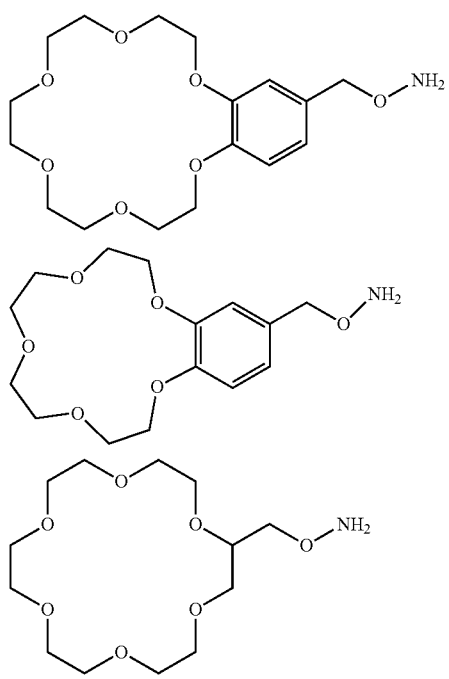
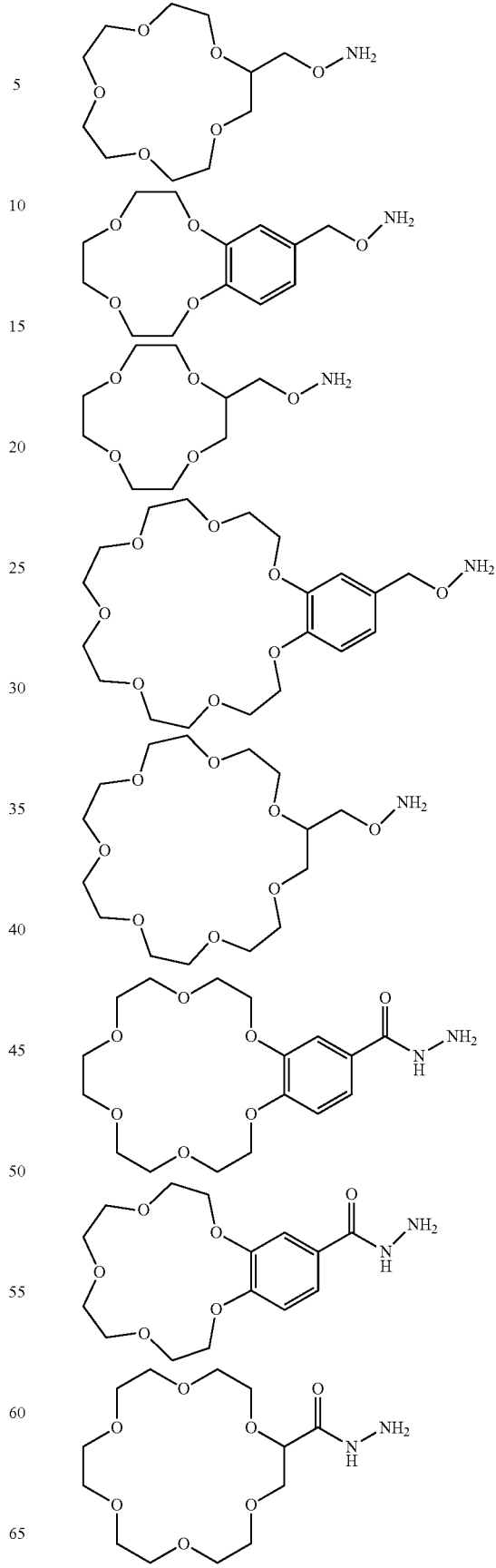

-continued
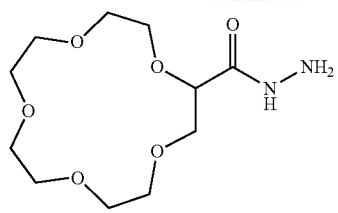
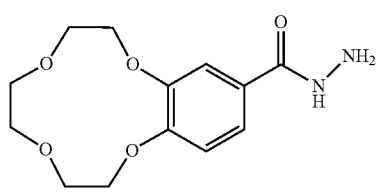
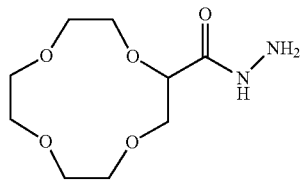
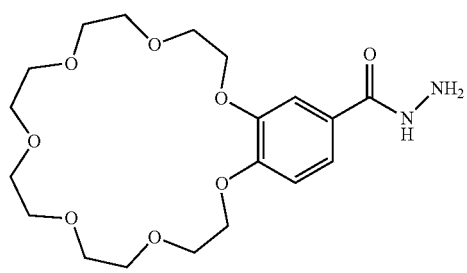
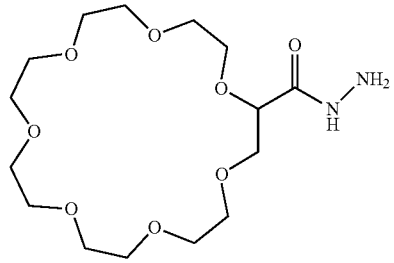
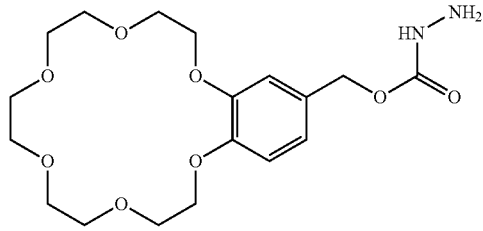
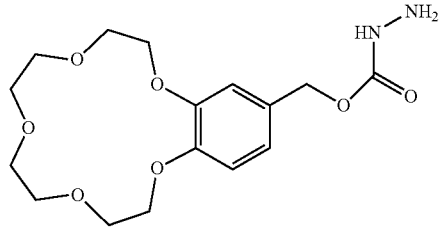
-continued
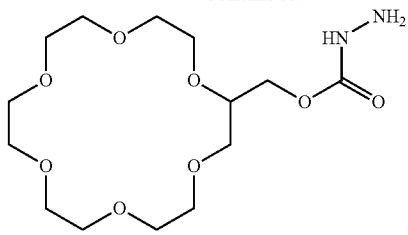
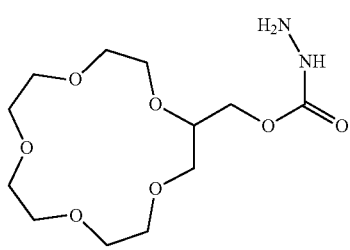
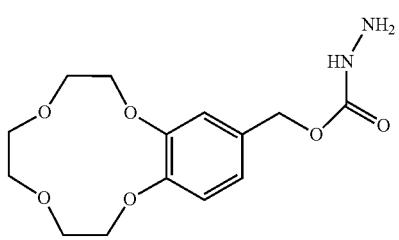
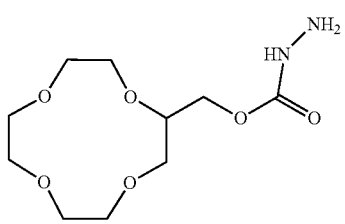
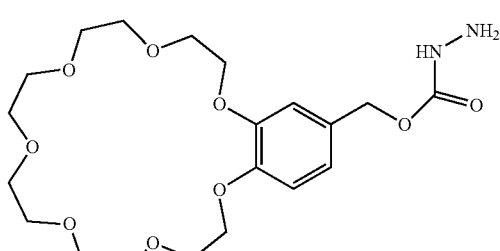
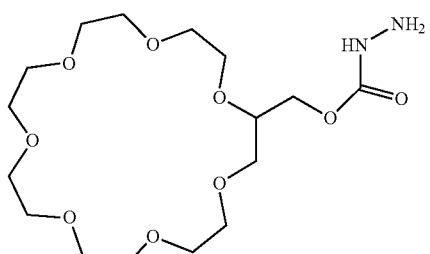
66. The derivatization reagent of embodiments 51-58, wherein the crown either derivatizing agent is selected from the agents of group IV:

55
Group IV.
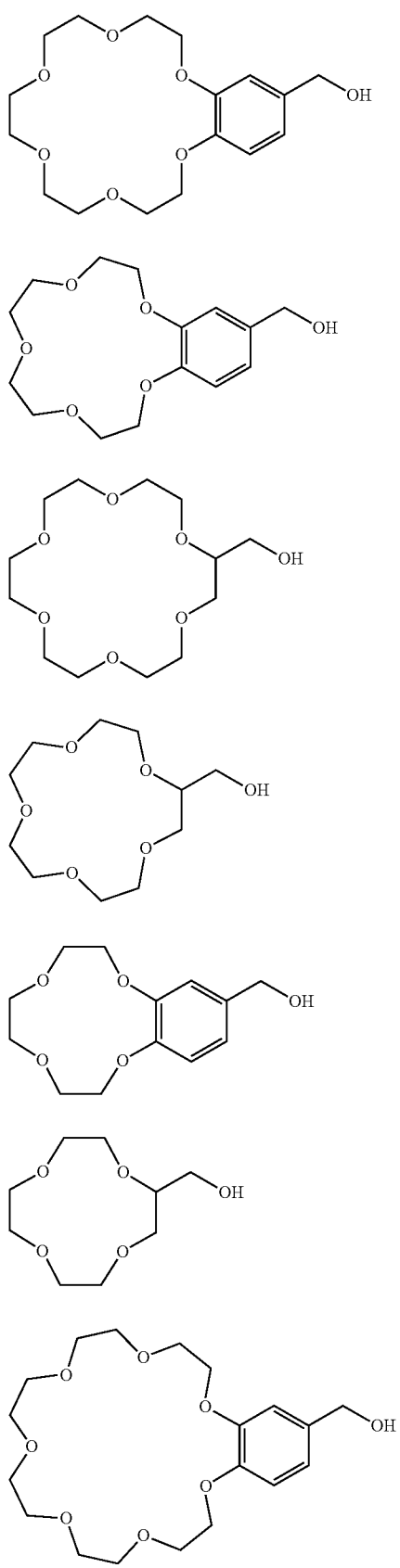
56
-continued
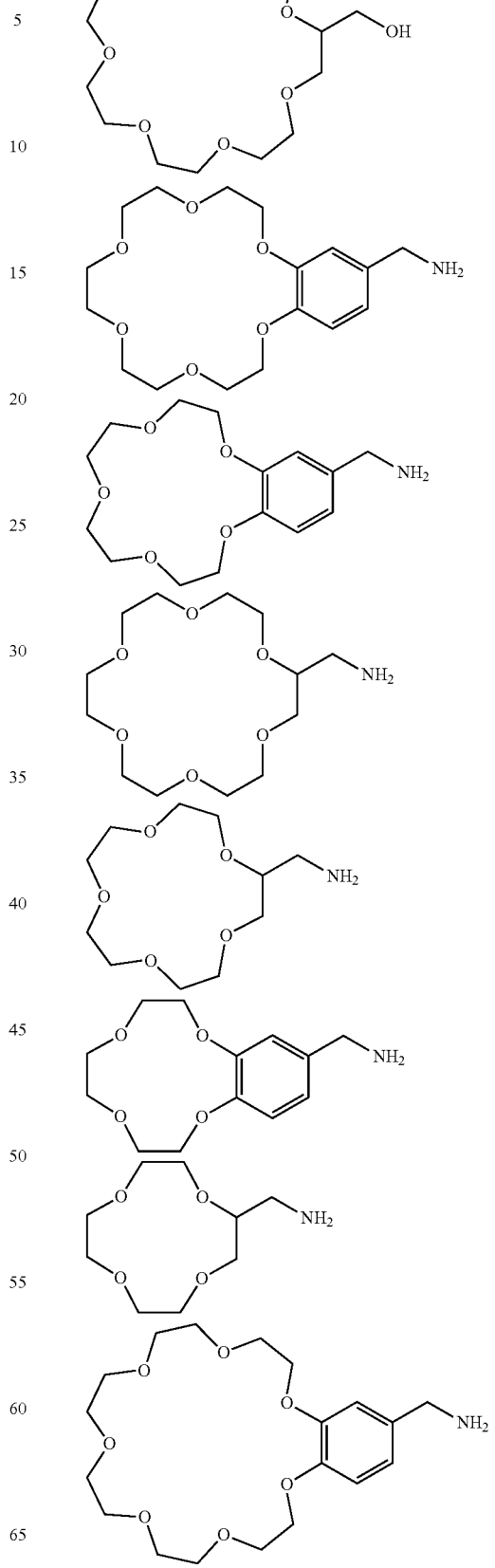

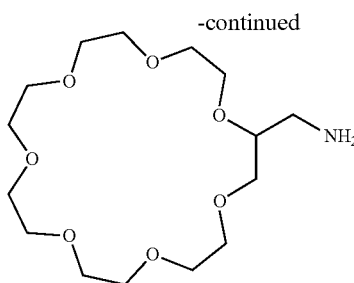

EXAMPLES

The following non-limiting examples are provided for illustrative purposes only in order to facilitate a more complete understanding of the disclosed subject matter. These examples should not be construed to limit any of the embodiments described in the present specification, including those pertaining to the methods for detecting an analyte and kits comprising the components necessary to perform the disclosed methods.

Example 1

Quantification of 1,25-dihydroxy-vitamin D in Plasma

Sample Collection

Plasma samples were obtained from human patients' blood. Samples were drawn (plasma sodium heparin & EDTA) into pre-chilled Vacutainers. Vacutainers were inverted 5× and refrigerated until centrifuged. Plasma was separated in a refrigerated centrifuge (1000×g for 10 minutes) within 30 minutes of collection and then frozen immediately at −20° C. in plastic vials.

Plasma was thawed and diluted before use in solid phase extraction.

Standards

The blanks, calibration samples, and plasma samples were spiked with internal standards (e.g., D6-1,25(OH)$_2$ vitamin D$_3$ and/or D6-1,25(OH)$_2$ vitamin D$_2$).

Standard curves were generated with plasma solutions spiked with a known amount of 1,24-dihydroxy-vitamin D. The spiking solution was serially diluted before being added to the plasma taken from the same plasma sample.

Extraction

TRACE-N® (3 cc/15 mg) columns were conditioned with 1.0 ml of methanol, followed by 1 ml deionized water.

Then 200 µL of the Sample was mixed with 1 mL of 28% iso-propyl alcohol in water. 10 µL internal standard was mixed with 1 mL of 28% iso-propyl alcohol in water. The Sample/buffer mix was loaded onto the column at a pressure of 2-3 psi. The column was washed with 1 ml of 28% iso-propyl alcohol in water at 6 psi. The column was dried under a stream of nitrogen gas for eight minutes at room temperature or heated to 45° C. for 4 min.

The sample was eluted from the column with 0.8 ml of Elution Buffer (20% ethyl acetate in hexane).

Solvent was evaporated under a stream of nitrogen gas with heating to 40° C. for 4 min. The extract was reconstituted with ethylacetate (100 µL).

The extract was derivatized as follows:

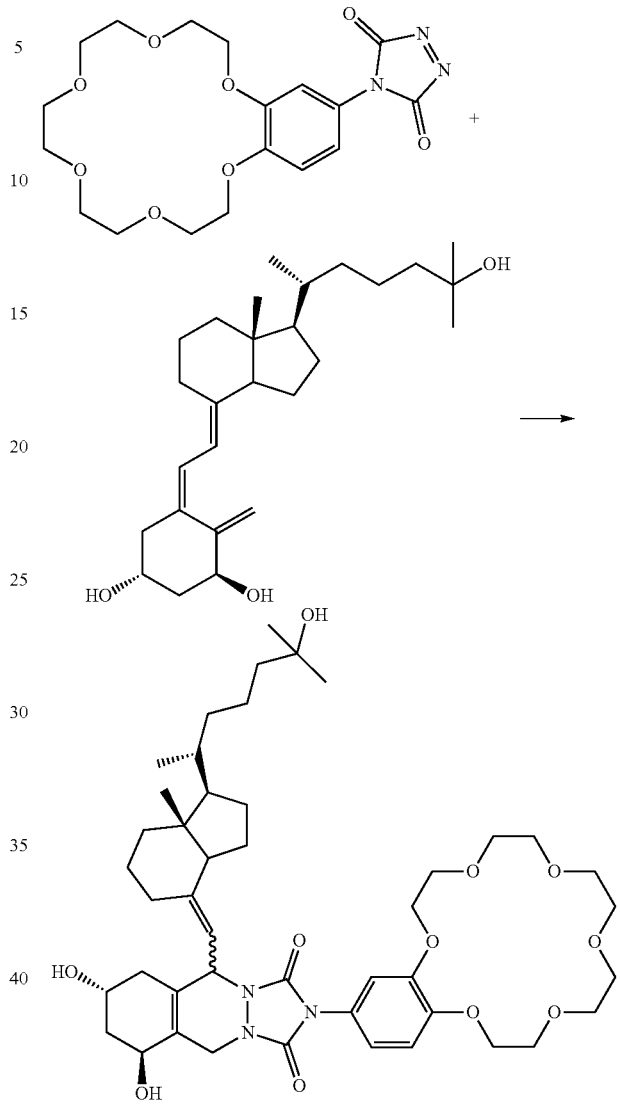

MB409 (the crown-ether derivatization agent) in ethylacetate (1 mg/mL, 5 µL) was added to the reconstituted extract and vortexed for 20 seconds. The derivatization reaction was permitted to proceed for 30 minutes at room temperature. The reaction is stopped with the addition of 20 µL methanol and vortexing for 10 seconds. The derivatized analyte was concentrated by streaming with nitrogen gas for 3 minutes. The concentrated analyte is reconstituted with 50 µL acetonitrile/NH$_4$CO$_2$H (50 mM) (at 3:1).

The reconstituted analyte was loaded onto an autosampler for LCMS analysis.

LC-MS/MS Analysis

10 µL of the solution obtained from the ammonium formate reaction was automatically injected into a TARGA® C18 3 µm particle size 50×2.1 mm analytical column. A binary HPLC gradient was applied to the analytical column to separate the crown ether derivatives of 1,25-dihydroxy vitamin D from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 600 µl/min over five minutes as follows:

| Gradient: | |
|---|---|
| Time (min) | B (%) |
| 0.01 | 50 |
| 2.00 | 50 |
| 2.05 | 98 |
| 4.00 | 98 |
| 4.50 | 50 |
| 5.00 | 50 |

MS/MS was performed using an AB Sciex 4000 QTrap for detection coupled to an Agilent 1200 binary LC pump controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with collision gas to generate ion fragments, which were passed to quadrupole 3 (Q3) for further selection. Simultaneously, the same process using isotope dilution mass spectrometry was carried out with internal standards, D6-1,25(OH)$_2$ vitamin D$_3$ and/or D6-1,25(OH)$_2$ vitamin D$_2$. The following mass transitions were used for detection and quantitation of 1,25-dihydroxy-vitamin D (and its corresponding internal standards) during validation on positive polarity from the same sample injection.

Results:

The results demonstrate an automated method for extracting 1,25-dihydroxy vitamin D. The method gives good linear response to both compounds from 5 pg mL-20 ng/mL of the standard curve, with an LOD of 10 pg/mL of plasma for 1,25-dihydroxy vitamin D by using an AB Sciex 4000 QTrap for detection coupled to an Agilent 1200 binary LC pump.

Example 2

Quantification of THC or HU210 in Oral Fluid

Sample Collection

Oral samples were taken from humans using the QUANTISAL™ (Immunalysis, California). Saliva was taken from patients using the collection device from QUANTISAL, and specimens were refrigerated and ultimately frozen. Saliva was thawed before use in the present quantification methods.

Standards

The blanks, calibration samples, and oral samples were spiked with internal standards (e.g., THC-d3).

Standard curves were generated with saliva solutions spiked with a known amount of THC or HU210 (a synthetic cannabinoid). The spiking solution was serially diluted before being added to the saliva taken from the same oral sample.

Extraction

TRACE-N® (3 cc/15 mg) columns were conditioned with 0.5 ml of methanol, followed by 0.5 ml 0.1% HCl (6M) in water.

Then 300 uL of the oral fluid in QUANTISAL™ buffer (25% v/v). 10 µL internal standard was added and 600 uL of 100 mM pH6 phosphate buffer. The Sample/buffer mix was loaded onto the column at a pressure of 2-3 psi. The column was washed with 1 mL of DI water, then 1 ml of 20% methanol in water at 2-3 psi. The column was dried under a stream of nitrogen gas for eight minutes at room temperature or heated to 45° C. for 4 min.

The sample was eluted from the column with 0.8 ml of Elution solvent (20% ethyl acetate in hexane).

Solvent was evaporated under a stream of nitrogen gas with heating to 40° C. for 8 min. The extract was reconstituted with acetonitrile (50 µL) K$_2$CO$_3$ (50 mM, 25 µL). MB388 (the crown-ether derivatization agent) in acetonitrile (10 mg/mL, 5 µL) was added to the reconstituted extract and vortexed for 20 seconds. The derivatization reaction was permitted to proceed for 30 minutes at room temperature. The reaction is stopped with the addition of 20 µL ammonium bicarbonate (300 mM).

The reconstituted analyte was loaded onto an autosampler for LCMS analysis.

LC-MS/MS Analysis

10 µL of the solution obtained from the ammonium formate reaction was automatically injected into a RAPTOR® C18 (2.7 µm particle size 50×2.1 mm analytical column. A binary HPLC gradient was applied to the analytical column to separate the crown ether derivatives of THC or HU210 from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 600 µl/min over five minutes as follows:

| Gradient: | |
|---|---|
| Time (min) | B (%) |
| 0.01 | 50 |
| 2.00 | 50 |
| 2.05 | 98 |
| 4.00 | 98 |
| 4.50 | 50 |
| 5.00 | 50 |

MS/MS was performed using an API 5000 triple quadrupole mass spectrometer controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with collision gas to generate ion fragments, which were passed to quadrupole 3 (Q3) for further selection. Simultaneously, the same process using isotope dilution mass spectrometry was carried out with internal standards, (−)-□-9-THC (D3). The following mass transitions were used for detection and quantitation of THC or HU210 (and the same internal standards) during validation on positive polarity from the same sample injection.

TABLE 3

MRM Transitions for THC

| Compound | Polarity | Precursor m/z | Product m/z |
|---|---|---|---|
| THC MB338 | Positive | 670 | 339 |
| THC MB338 | Positive | 670 | 163 |
| THC MB338 | Positive | 670 | 107 |
| THC d3 MB338 | Positive | 673 | 339 |
| THC d3 MB338 | Positive | 673 | 163 |
| THC d3 MB338 | Positive | 673 | 107 |

TABLE 3-continued

MRM Transitions for THC

| Compound | Polarity | Precursor m/z | Product m/z |
|---|---|---|---|
| HU210 MB338 | Positive | 742 | 337 |
| HU210 MB338 | Positive | 742 | 339 |
| HU210 MB338 | Positive | 742 | 163 |

Results:

Table 4 shows the results of the standard curve of THC.

TABLE 4

THC Standard Curve Data

THC Standard Curve Low

| Sample Name | Sample Type | Acquistion D | Vial Position | Analyte Peak | IS Peak Area | Analyte Conc | Area Ratio | Calculated Concentration (ng/mL) |
|---|---|---|---|---|---|---|---|---|
| 087 Low Cont | Standard | Mar. 26, 2015 8:3 | 87 | 2.32e+006 | 2.47e+006 | 100 | 9.39e−001 | 95.9 |
| 088 Low Cont | Standard | Mar. 26, 2015 8:3 | 88 | 2.62e+006 | 2.61e+006 | 100 | 1.00e+000 | 103 |
| 089 Low Cont | Standard | Mar. 26, 2015 8:4 | 89 | 2.71e+006 | 2.78e+006 | 100 | 9.74e−001 | 99.5 |
| 090 Low Cont | Standard | Mar. 26, 2015 8:4 | 90 | 2.81e+006 | 2.79e+006 | 100 | 1.01e+000 | 103 |
| 091 Low Cont | Standard | Mar. 26, 2015 8:5 | 91 | 2.93e+006 | 3.01e+006 | 100 | 9.71e−001 | 99.1 |
| 032 Low Cont | Unknown | Mar. 26, 2015 3:1 | 32 | 2.44e+006 | 3.15e+006 | N/A | 7.73e−001 | 79 |
| 033 Low Cont | Unknown | Mar. 26, 2015 3:1 | 33 | 2.54e+006 | 3.17e+006 | N/A | 8.03e−001 | 82 |
| 034 Low Cont | Unknown | Mar. 26, 2015 3:2 | 34 | 2.19e+006 | 2.72e+006 | N/A | 8.02e−001 | 81.9 |
| 035 Low Cont | Unknown | Mar. 26, 2015 3:2 | 35 | 2.04e+006 | 2.48e+006 | N/A | 8.23e−001 | 84 |
| 036 Low Cont | Unknown | Mar. 26, 2015 3:3 | 36 | 2.74e+006 | 3.33e+006 | N/A | 8.22e−001 | 83.9 |
| | | | | | | | Average % Recovery | 82.16 |

THC Standard Curve High

| Sample Name | Sample Type | Acquistion D | Vial Position | Analyte Peak | IS Peak Area | Analyte Conc | Area Ratio | Calculated Concentration (ng/mL) |
|---|---|---|---|---|---|---|---|---|
| 092 High Con | Standard | Mar. 26, 2015 8:5 | 92 | 1.94e+007 | 2.84+006 | 100 | 6.81e+000 | 104 |
| 093 High Con | Standard | Mar. 26, 2015 9:0 | 93 | 2.21e+007 | 3.37+006 | 100 | 6.57e+000 | 99.9 |
| 094 High Con | Standard | Mar. 26, 2015 9:1 | 94 | 2.00e+007 | 3.19+006 | 100 | 6.29e+000 | 95.7 |
| 095 High Con | Standard | Mar. 26, 2015 9:1 | 95 | 2.09e+007 | 3.14+006 | 100 | 6.66e+000 | 101 |
| 096 High Con | Standard | Mar. 26, 2015 9:2 | 96 | 1.91e+007 | 2.93+006 | 100 | 6.64e+000 | 99.5 |
| 045 High Con | Unknown | Mar. 26, 2015 4:2 | 45 | 1.63e+007 | 2.81+006 | N/A | 5.81e+000 | 88.3 |
| 046 High Con | Unknown | Mar. 26, 2015 4:3 | 46 | 1.48e+007 | 2.43+006 | N/A | 6.11e+000 | 92.9 |
| 047 High Con | Unknown | Mar. 26, 2015 4:3 | 47 | 1.59e+007 | 2.55+006 | N/A | 6.25e+000 | 95 |
| 048 High Con | Unknown | Mar. 26, 2015 4:4 | 48 | 1.68e+007 | 2.80+006 | N/A | 6.00e+000 | 91.2 |
| | | | | | | | Average % Recovery | 91.85 |

Table 5 shows the standard curve data for H210.

TABLE 5

H210 Data

HU210 Curve Low

| Sample Name | Sample Type | Acquistion D | Vial Position | Analyte Peak | IS Peak Area | Analyte Conc | Area Ratio | Calculated Concentration (ng/mL) |
|---|---|---|---|---|---|---|---|---|
| 087 Low Cont | Standard | Mar. 26, 2016 8:3 | 87 | 7.73e+006 | 2.47e+006 | 100 | 3.12e−001 | 103 |
| 088 Low Cont | Standard | Mar. 26, 2016 8:3 | 88 | 8.37e+006 | 2.81e+006 | 100 | 3.21e−001 | 105 |
| 089 Low Cont | Standard | Mar. 26, 2016 8:4 | 89 | 8.51e+006 | 2.78e+006 | 100 | 3.06e−001 | 101 |
| 090 Low Cont | Standard | Mar. 26, 2016 8:4 | 90 | 8.29e+006 | 2.79e+006 | 100 | 2.97e−001 | 97.6 |
| 091 Low Cont | Standard | Mar. 26, 2016 8:5 | 91 | 8.62e+006 | 3.01e+006 | 100 | 2.86e−001 | 93.8 |
| 032 Low Cont | Unknown | Mar. 26, 2016 3:1 | 32 | 8.53e+006 | 3.15e+006 | N/A | 2.70e−001 | 88.8 |
| 033 Low Cont | Unknown | Mar. 26, 2016 3:1 | 33 | 7.91e+006 | 3.17e+006 | N/A | 2.50e−001 | 82 |
| 034 Low Cont | Unknown | Mar. 26, 2016 3:2 | 34 | 6.57e+006 | 2.72e+006 | N/A | 2.41e−001 | 79.1 |
| 035 Low Cont | Unknown | Mar. 26, 2016 3:2 | 35 | 5.78e+006 | 2.48e+006 | N/A | 2.33e−001 | 76.5 |
| 036 Low Cont | Unknown | Mar. 26, 2016 3:3 | 36 | 7.16e+006 | 3.33e+006 | N/A | 2.15e−001 | 70.6 |
| | | | | | | | Average % Recovery | 79.4 |

Hu210 Curve High

| Sample Name | Sample Type | Acquistion D | Vial Position | Analyte Peak | IS Peak Area | Analyte Conc | Area Ratio | Calculated Concentration (ng/mL) |
|---|---|---|---|---|---|---|---|---|
| 092 High Con | Standard | Mar. 26, 2015 8:5 | 92 | 6.08e+006 | 2.84e+006 | 100 | 2.14e+000 | 103 |
| 093 High Con | Standard | Mar. 26, 2015 9:0 | 93 | 8.89e+006 | 3.37e+006 | 100 | 2.04e+000 | 98 |
| 094 High Con | Standard | Mar. 26, 2015 9:1 | 94 | 6.37e+006 | 3.19e+006 | 100 | 2.00e+000 | 96.9 |
| 095 High Con | Standard | Mar. 26, 2015 9:1 | 95 | 6.43e+006 | 3.14e+006 | 100 | 2.05e+000 | 98.2 |

TABLE 5-continued

H210 Data

| | | | | | | | | |
|---|---|---|---|---|---|---|---|---|
| 096 High Con | Standard | Mar. 26, 2015 9:2 | 96 | 6.43e+006 | 2.93e+006 | 100 | 2.20e+000 | 105 |
| 045 High Con | Unknown | Mar. 26, 2015 4:2 | 45 | 5.63e+006 | 2.81e+006 | N/A | 2.01e+000 | 96.3 |
| 046 High Con | Unknown | Mar. 26, 2015 4:3 | 46 | 5.05e+006 | 2.43e+006 | N/A | 2.08e+000 | 99.7 |
| 047 High Con | Unknown | Mar. 26, 2015 4:3 | 47 | 4.61e+006 | 2.55e+006 | N/A | 1.81e+000 | 86.8 |
| 048 High Con | Unknown | Mar. 26, 2015 4:4 | 48 | 5.11e+006 | 2.80e+006 | N/A | 1.82e+000 | 87.4 |
| | | | | | | Average % Recovery | | 92.55 |

Figure 2A:
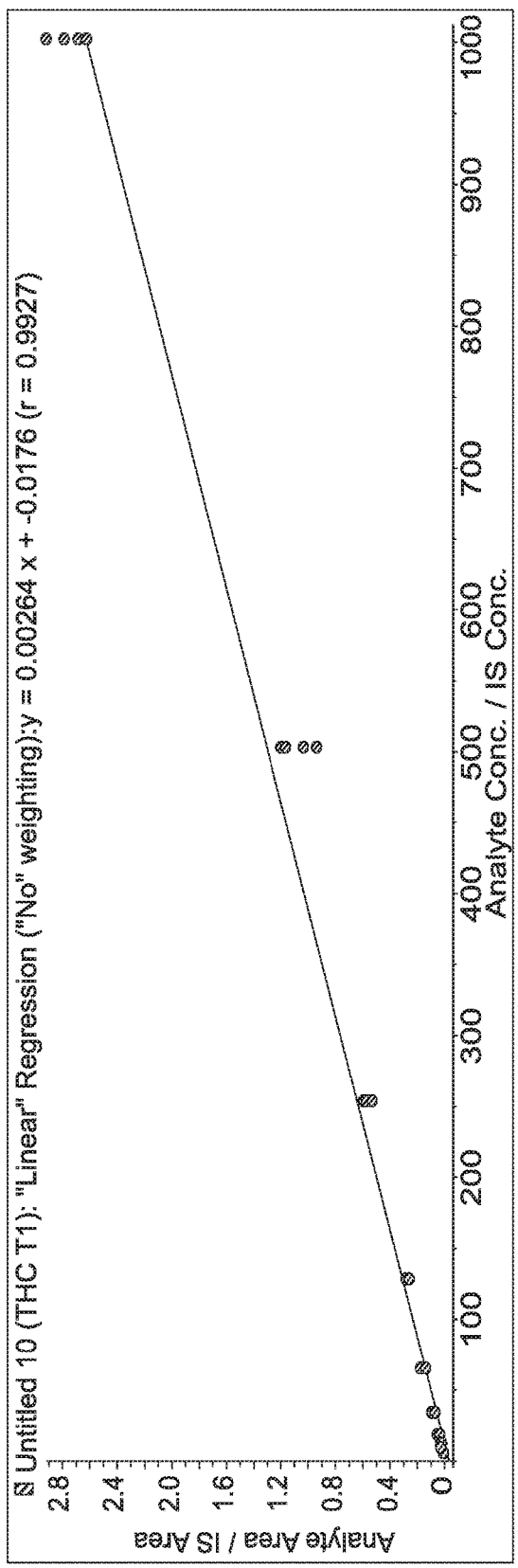
FIGS. 2A and B demonstrate the linear regression of THC and HU210 spiked samples tested according to the present methods.
Figure 2B:
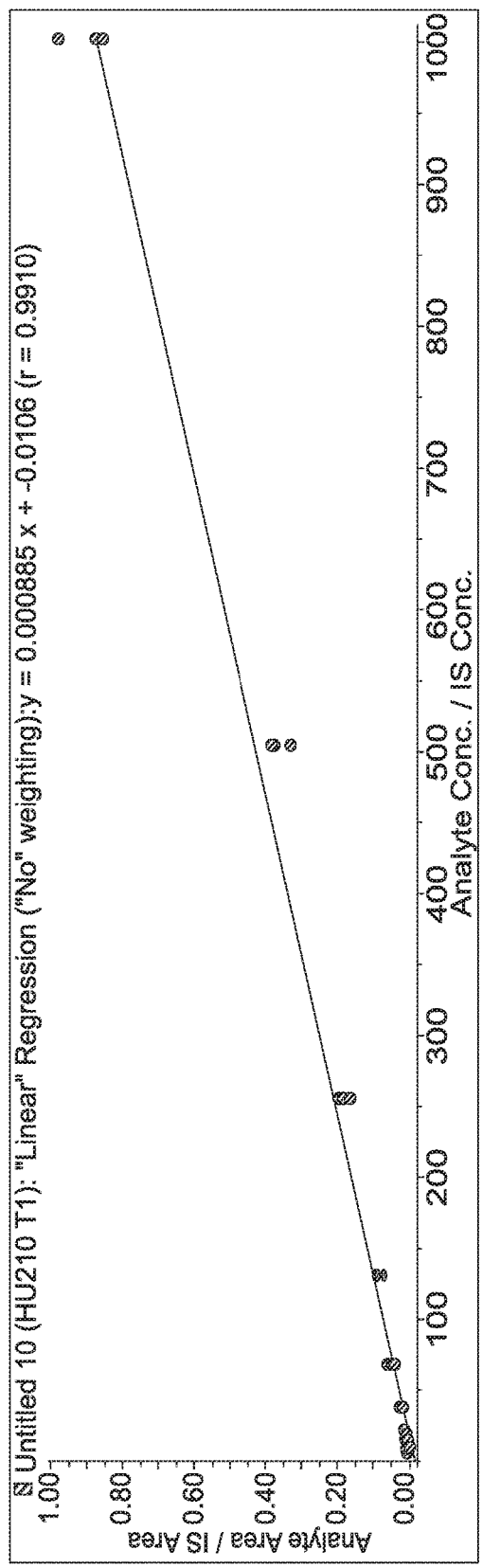

Tables 4 and 5 show the data representing the percent recovery of THC or HU210 from a plasma sample spiked with 250 fg/mL-2 ng/mL THC or HU210. LLOD: 200 fg on column, LLOQ: 400 fg on column. The assay LLOD was 20 pg/mL and LLOQ was 40 pg/mL, with extraction of 75 uL of saliva. Recovery of the analyte was 80-92%. FIGS. 2A and 2B show the linear regression for THC and HU210.

The results describe an automated method for extracting THC and HU210 from oral fluid. The method gives good linear response to both compounds from 250 fg mL-2 ng/mL of the standard curve, with an LOD of 1 pg/mL of oral fluid for both THC and HU210 by using an AB Sciex 5000 for detection coupled to a pair of Shimadzu 20AD LC pumps.

Example 3

Quantification of Estradiol/Estriol/Estrone/17I-Estradiol-2,3,4-$^{13}C_3$ in Plasma Sample Collection Plasma samples were obtained from human patients' blood. Samples were drawn (plasma sodium heparin & EDTA) into pre-chilled Vacutainers. Vacutainers were inverted 5× and refrigerated until centrifuged. Plasma was separated in a refrigerated centrifuge (1000×g for 10 minutes) within 30 minutes of collection and then frozen immediately at −20° C. in plastic vials.

Plasma was thawed and diluted before use in solid phase extraction.

Standards

The blanks, calibration samples, and plasma samples were spiked with internal standards (e.g., 17β-estradiol-2,3,4-$^{13}C_3$).

Standard curves were generated with plasma solutions spiked with a known amount of estradiol or estrone. The spiking solution was serially diluted before being added to the plasma taken from the same plasma sample.

Extraction

MAESTRO® A(1 cc/15 mg) columns were conditioned with 1.0 mL of methanol, followed by 0.5 mL deionized water.

Then 100 µL of the Sample was mixed with 0.5 mL of water. Another 0.5 mL of water was added. The Sample/buffer mix was loaded onto the column at a pressure of 2-3 psi. The column was washed with 1 ml of 20% iso-propyl alcohol in water at 6 psi. The column was dried under a stream of nitrogen gas for 10 minutes at room temperature or heated to 45° C. for 5 min.

The sample was eluted from the column with 0.7 ml of Elution solvent (80:20 hexane:ethyl acetate).

Solvent was evaporated under a stream of nitrogen gas with heating to 40° C. for 4 min. The extract was reconstituted with acetonitrile (50 µL) K$_2$CO$_3$ (50 mM, 25 µL).

The extract was derivatized as follows:

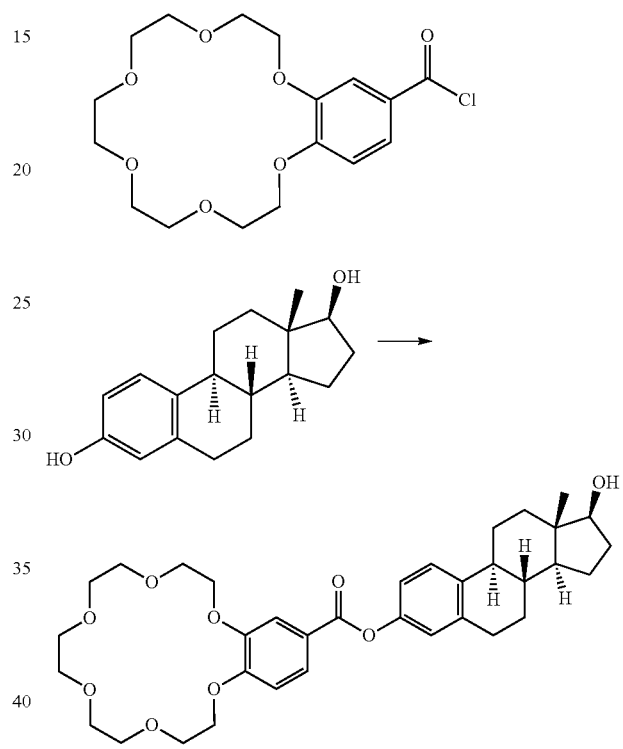

MB388 (the crown-ether derivatization agent) in acetonitrile (10 mg/mL, 5 µL) was added to the reconstituted extract and vortexed for 20 seconds. The derivatization reaction was permitted to proceed for 30 minutes at room temperature. The reaction is stopped with the addition of 20 µL ammonium bicarbonate (300 mM).

The reconstituted analyte was loaded onto an autosampler for LCMS analysis.

LC-MS/MS Analysis

10 µL of the solution obtained from the ammonium formate reaction was automatically injected into a Targa® C18 (3 µm particle size 50×2.1 mm analytical column. A binary HPLC gradient was applied to the analytical column to separate the crown ether derivatives of Estradiol or Estrone from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 600 µl/min over five minutes as follows:

Gradient:

| Time (min) | B (%) |
| --- | --- |
| 0.01 | 50 |
| 3.00 | 100 |
| 4.00 | 100 |
| 4.5 | 50 |
| 5 | 50 |

MS/MS was performed using an API 4000 QTRAP triple quadrupole mass spectrometer coupled to an Agilent 1200 binary HPLC pump, controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with collision gas to generate ion fragments, which were passed to quadrupole 3 (Q3) for further selection. Simultaneously, the same process using isotope dilution mass spectrometry was carried out with internal standards.

The following mass transitions were used for detection and quantitation of Estradiol or Estrone (and their corresponding internal standards) during validation on positive polarity from the same sample injection.

TABLE 6

Mass Transitions

| Compound | Polarity | Precursor m/z | Product m/z |
| --- | --- | --- | --- |
| Estrone MB338 | Positive | 626.46 | 338.8 |
| Estrone MB338 | Positive | 626.46 | 163 |
| Estradiol MB338 | Positive | 628.56 | 339.1 |
| Estradiol MB338 | Positive | 628.56 | 162.9 |
| Estriol MB338 | Positive | 644.28 | 339 |
| Estriol MB338 | Positive | 644.28 | 162.8 |
| 17ß-Estradiol-2,3,4-13C3 MB338 | Positive | 631.399 | 339 |
| 17ß-Estradiol-2,3,4-13C3 MB338 | Positive | 631.399 | 163 |
| 17ß-Estradiol-2,3,4-13C3 MB338 | Positive | 631.399 | 107 |

TABLE 7

Estrone and Estradiol Mass and Dwell Time

| Compound | Parent Mass (m/z) | Fragment (m/z) | Dwell Time (ms) | DP | EP | CP | CXP |
| --- | --- | --- | --- | --- | --- | --- | --- |
| Estrone MB338 1 | 626.46 | 338.8 | 100 | 86 | 10 | 33 | 8 |
| Estrone MB338 2 | 626.46 | 163 | 100 | 86 | 10 | 59 | 12 |
| Estradiol MB338 1 | 628.56 | 339.1 | 100 | 86 | 10 | 33 | 10 |
| Estradiol MB338 2 | 628.56 | 162.9 | 100 | 86 | 10 | 59 | 12 |
| 17ß-Estradiol-2,3,4-13C3 MB338 1 | 631.399 | 339 | 100 | 96 | 10 | 33 | 8 |
| 17ß-Estradiol-2,3,4-13C3 MB338 1 | 631.399 | 163 | 100 | 96 | 10 | 63 | 26 |

TABLE 8

Recovery Data

| Sample | Analyte | Analyte Peak Area (counts) | % Recovery |
| --- | --- | --- | --- |
| Std Curve 200 pg/mL | Estrone 626.46 > 338.8 | 32000 | 201 |
| Std Curve 200 pg/mL | Estradiol 628.56 > 339.1 | 30900 | 184 |
| Patient Sample 1 | Estrone 626.46 > 338.8 | 7510 | 48.1 |
| Patient Sample 1 | Estradiol 628.56 > 339.1 | 2560 | 20.6 |
| Patient Sample 4 | Estrone 626.46 > 338.8 | 18100 | 112 |
| Patient Sample 4 | Estradiol 628.56 > 339.1 | 20100 | 154 |
| Patient Sample 6 | Estrone 626.46 > 338.8 | 702 | 6.63 |
| Patient Sample 6 | Estradiol 628.56 > 339.1 | 1610 | 15.2 |

Figure 3A:
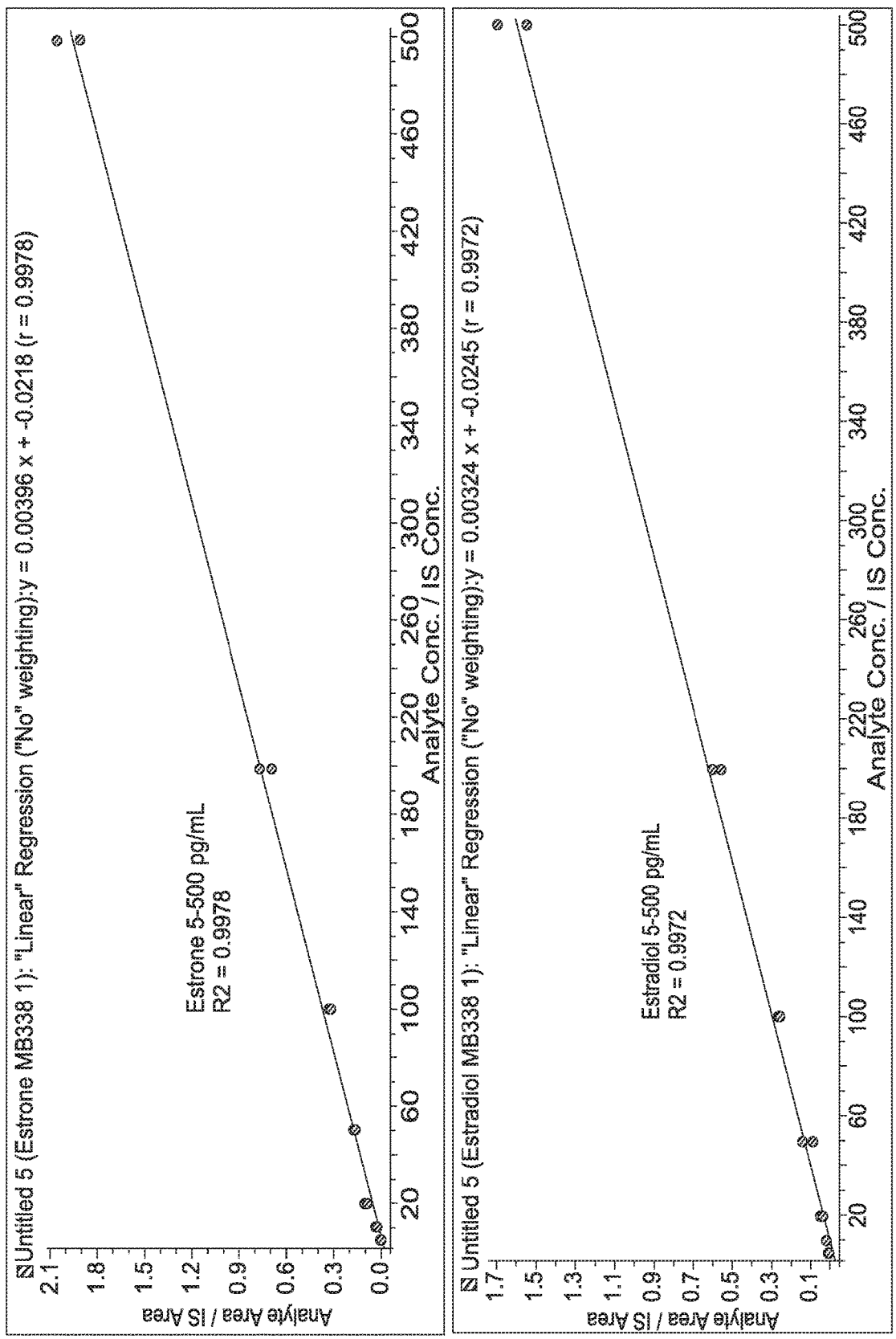
FIGS. 3A and B demonstrate the linear regression of estrone and estradiol samples tested according to the present methods, and their chromatograms.
Figure 3B:
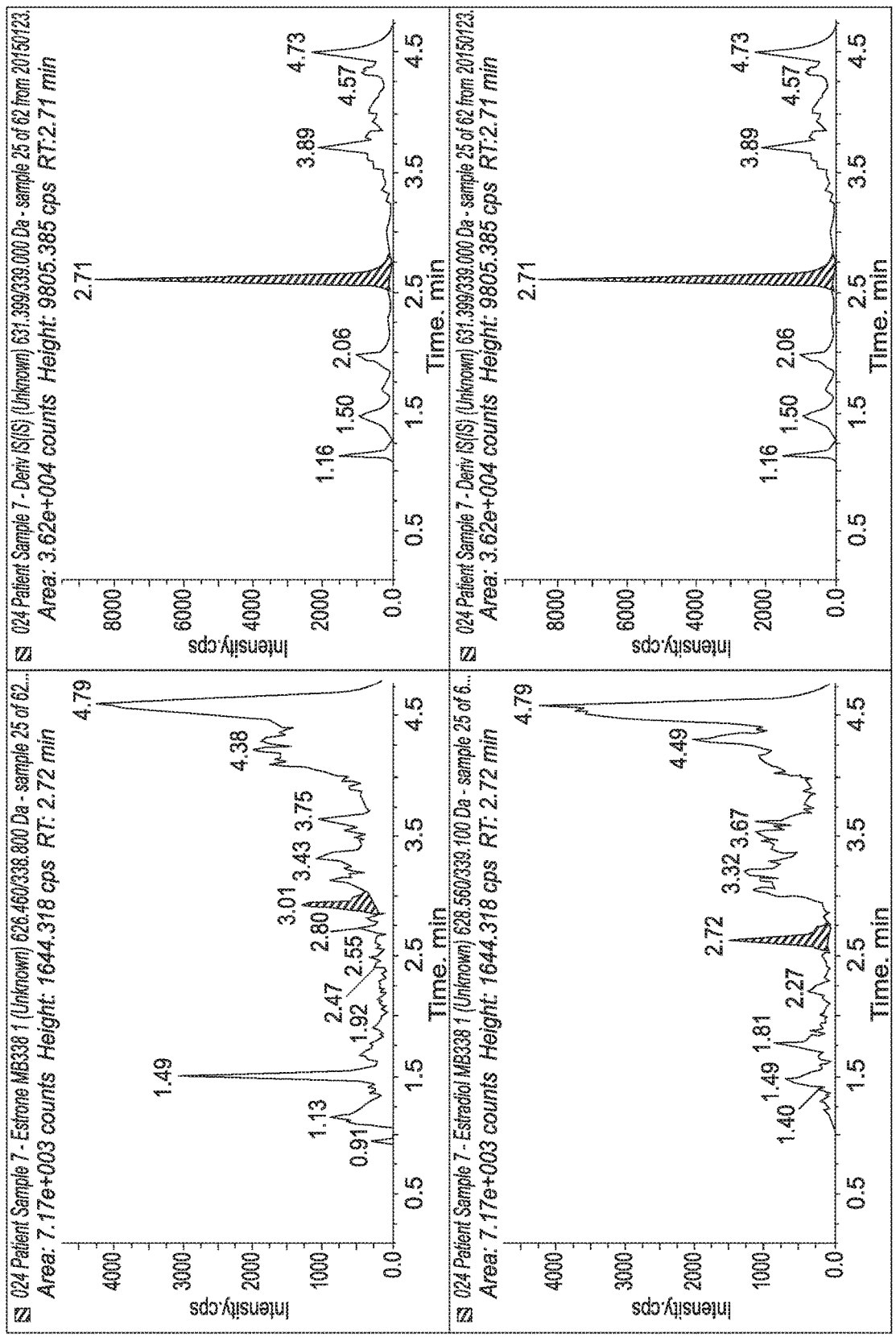

The method is an automated method for extracting Estrone (E1) and 17β-estradiol (E2) from 100 uL plasma. The method gives good linear response to both compounds from 5-500 pg/mL, with an LOD of 5 pg/mL for Estradiol and 10 ng for Estrone using an AB Sciex Qtrap 4000 for detection coupled to an Agilent 1200 HPLC (see FIGS. 3A and 3B).

Figure 4A:
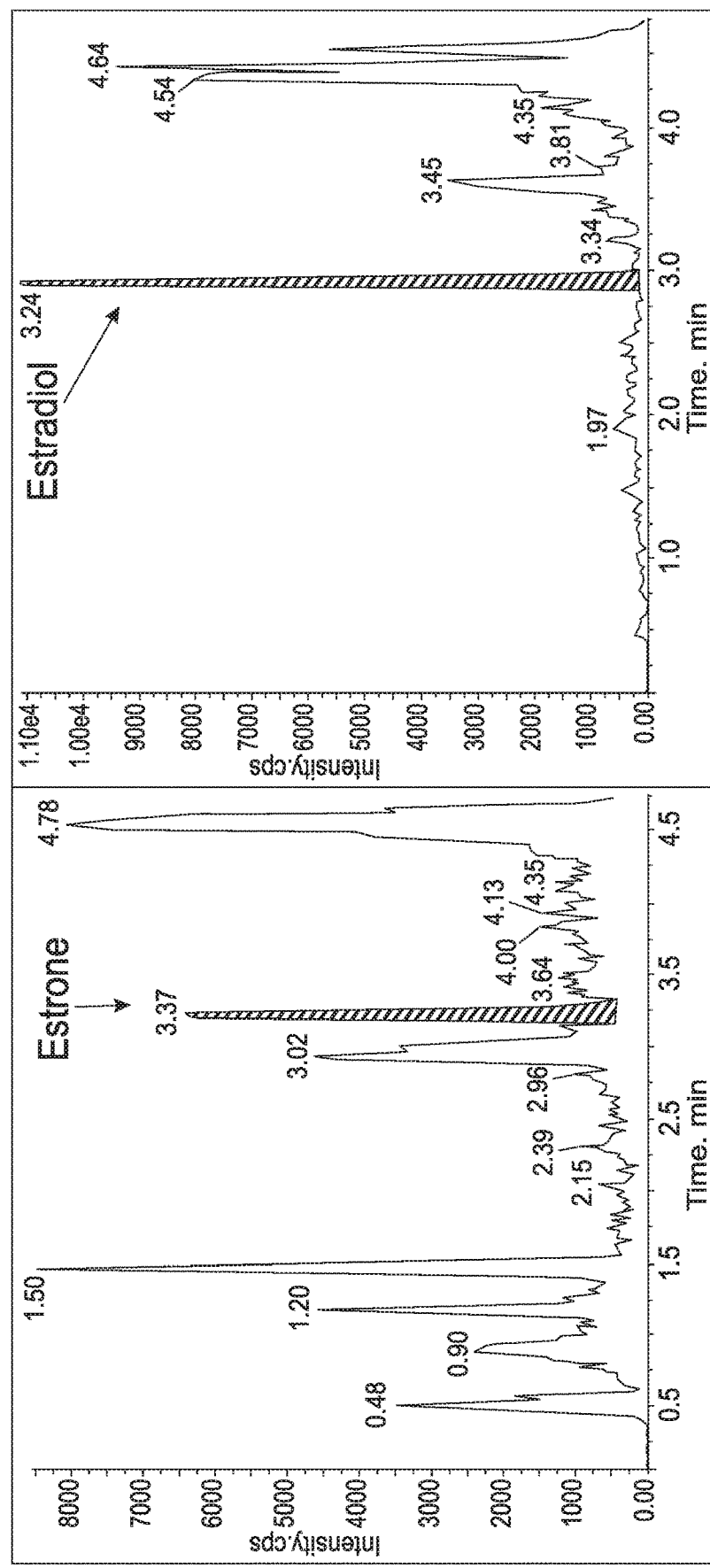
FIGS. 4A and B demonstrate chromatograms of estrone and estradiol samples tested according to the present methods, and the amounts of estradiol/estrone in samples taken from 10 individuals.

Further tests have demonstrated detection of estrone and estradiol in the pictogram range with a LOQ of 10 pg/mL for both compounds. Absolute recovery for Estrone and Estradiol were >90% (see FIG. 4A for additional chromatograms).

To test for variability ten replicate samples were spiked to a concentration of 100 pg/mL.

Subsequent extraction and analysis showed a 7.6% and 8.6% CSV for estrone and estradiol (data not shown).

Figure 4B:
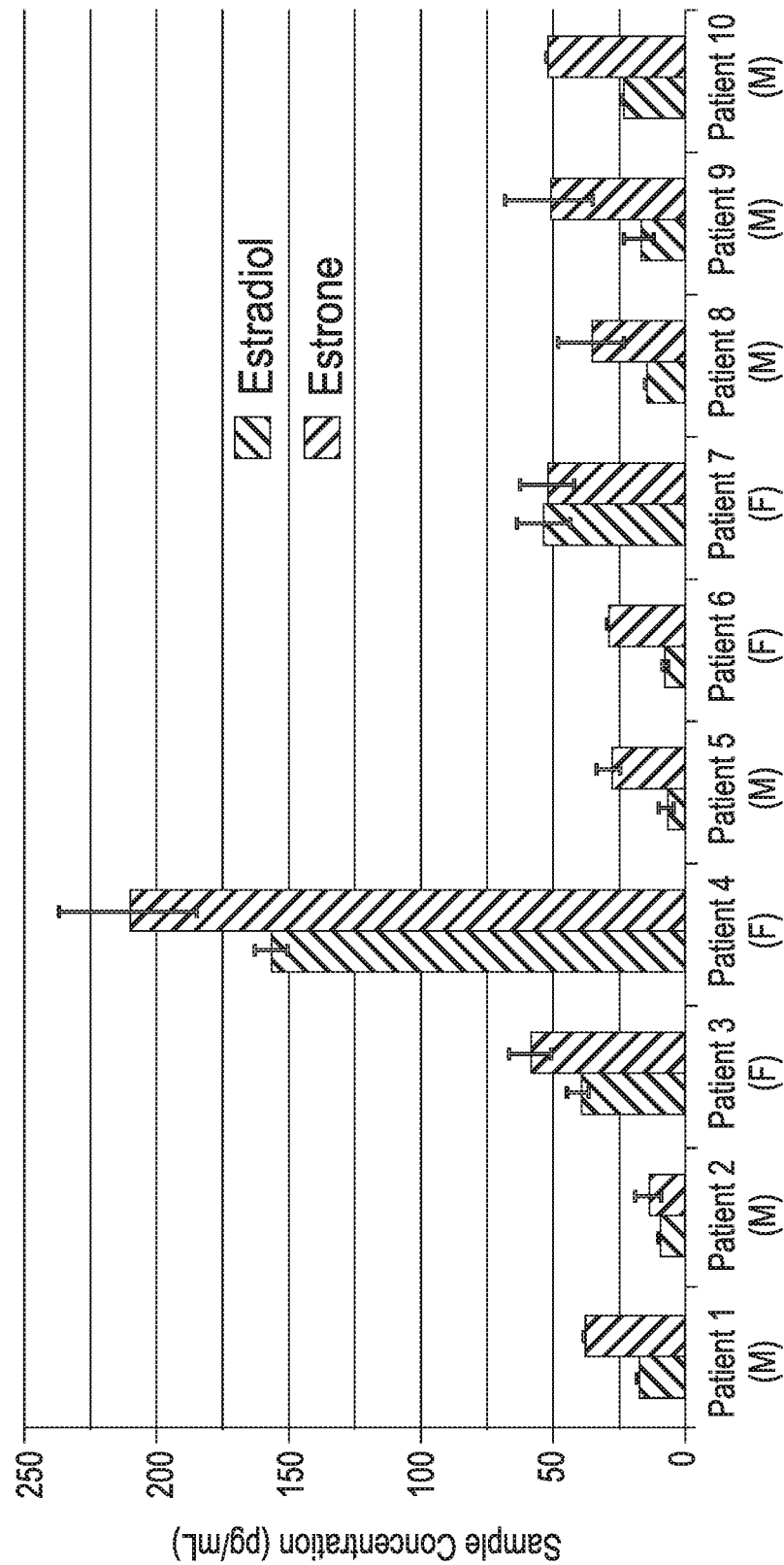

Finally, plasma from ten volunteers was measured in duplicate and analyzed for estradiol and estrone. The level of estrone and estradiol in all samples corresponded to physiological levels found in healthy adults (See FIG. 4B). Females (such as patient 4) have a wide range of estrogen levels depending on fertility and health factors, and the assay is able to measure the full extent of these values.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising"

are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method for determining the presence of one or more analytes in a test sample, the method comprising:
   a) extraction and purification of the one or more analytes from the test sample with one or more of solid phase extraction, supported liquid extraction (SLP), and liquid liquid extraction (LLP);
   b) derivatization of the one or more analytes with a crown-ether derivatizing agent; and
   c) detection of the one or more derivatized analytes using LC-MS/MS.

2. The method of claim 1, wherein the one or more analytes is a drug, a hormone, a signaling agent, an amino acid, or a pesticide.

3. The method of claim 1, wherein the one or more analytes is a monoamine neurotransmitter including vitamin D or one of its derivatives or metabolites, a sex hormone or one of its derivatives or metabolites, a cannabinoid or one of its derivatives or metabolites, an opiate, opioid or one of its derivatives or metabolites or an arylcyclohexylamine or one of its derivatives or metabolites, or an Amphetamine or one of its derivatives or metabolites.

4. The method of claim 3, wherein:
   the monoamine neurotransmitter is Histamine, Tryptamine, Serotonin, or Agmatine;
   the sex hormone or one of its derivatives or metabolites is an estrogen;
   the derivative of vitamin D is D is 25-OH $D_3$, 25-OH $D_2$, 24,25-$(OH)_2D_3$, 1,25-$(OH)_2D_3$, and 1,25-$(OH)_2D_2$, Cholecalciferol, 25-Hydroxycholecalciferol, 1α,25-Dihydroxycholecalciferol, Ergocalciferol, 1α,25-Dihydroxyergocalciferol, 22,23-Dihydroergocalciferol, 1α,24R,25-Trihydroxycholecalciferol, (6Z)-tacalciol, Tachysterol$_3$, Isovitamin $D_3$, or Dihydrotachysterol$_3$;
   the cannabinoid or one of its derivatives or metabolites is a Cannabigerol-type (CBG) cannabinoid, a Cannabichromene-type (CBC) cannabinoid, a Cannabidiol-type (CBD) cannabinoid, a Cannabinodiol-type (CBND) cannabinoid, a Tetrahydrocannabinol-type (THC) cannabinoid, a Cannabinol-type (CBN) cannabinoid, a Cannabitriol-type (CBT) cannabinoid, a Cannabielsoin-type (CBE) cannabinoid, an Isocannabinoid, a Cannabicyclol-type (CBL) cannabinoid, a Cannabicitran-type (CBT) cannabinoid, or a Cannabichromanone-type (CBCN) cannabinoid;
   the opiate, the opioid or the derivative or metabolite of the opiate or opioid, is morphine, oripavine, morphinone, hydromorphone, oxymorphone, a benzylisoquinoline alkaloid, a semi-synthetic or a benzylisoquinoline alkaloid derivative;
   the arylcyclohexylamine or one of its derivatives or metabolites is Tiletamine, 3-Methoxetamine (MXE), Methoxyketamine, N-Ethylnorletamine (Ethketamine), Amphetamine, Ephedrine, or Methamphetamine; or
   the Amphetamine or one of its derivatives or metabolites is Amphetamine, methamphetamine, ephedrine, cathinone, 3,4-methylenedioxy-N-met hylamphetamine (MDMA), or 25-Dimethoxy-4-methylamphetamine (DOM).

5. The method of claim 1, wherein the solid phase extraction is performed with an ion exchange column or cartridge, wherein the ion exchange column is a cation exchange column, a weak cation exchange column or an anion exchange column.

6. The method of claim 1, wherein the solid phase extraction is performed with a reverse phase silica column or cartridge.

7. The method of claim 6, wherein the reverse phase silica is an alkyl bounded (C4, C8, C12, or C18) silica, a cyano bounded silica, a phenyl bounded silica, or a biphenyl bounded silica.

8. The method of claim 1, wherein the sample is a biological sample, a soil sample, or a sample of food stuff.

9. The method of claim 8, wherein the biological sample is a blood sample, a saliva sample, a lachrymal sample, a urine sample, or a tissue sample.

10. The method of claim 9, wherein the blood sample is a full blood sample, a plasma sample, or a serum sample.

11. The method of claim 1, wherein the crown-ether derivatizing agent comprises: a crown-ether, a connector, and an analyte-binding functional group.

12. The method of claim 11, wherein the crown-ether comprises a ring, and the ring is a 12-30 membered ring.

13. The method of claim 12, wherein the ring has 12-30 member atoms of which 8-20 atoms are carbon and wherein the non-carbon member atoms are selected from oxygen, nitrogen, and sulfur.

14. The method of claim 11, wherein the crown ether is selected from 12 Crown 4, 15 Crown 5, 16 crown 4, 18 Crown 6, 21 Crown 7, or 24 Crown 8, optionally having one or more heteroatoms replacing oxygen.

15. The method of claim 11, wherein the connector is a $C_1$-$C_{12}$ linear, branched, and/or cyclic alkyl group or a phenolic ring fused to the crown ether.

16. The method of claim 11, wherein the analyte binding group is an acylating group, 4-Phenyl-1,2,4-triazolin-3,5-dione (PTAD), 1,2,4-traizoline-3,5-dione (TAD), an Alkoxylamine, a hydrazide, an alcohol, or an amine.

17. The method of claim 16, wherein the acylating group is an acylating agent of Formula 2:

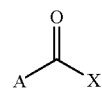

Formula 2 where A is the analyte and X is the connector.

18. The method of claim 17, wherein the acylating agent that is an acyl chloride or acyl halide.
19. The method of claim 1, where the crown ether derivatizing agent is selected from the agents of Group I, II, III, or IV:
Group 1
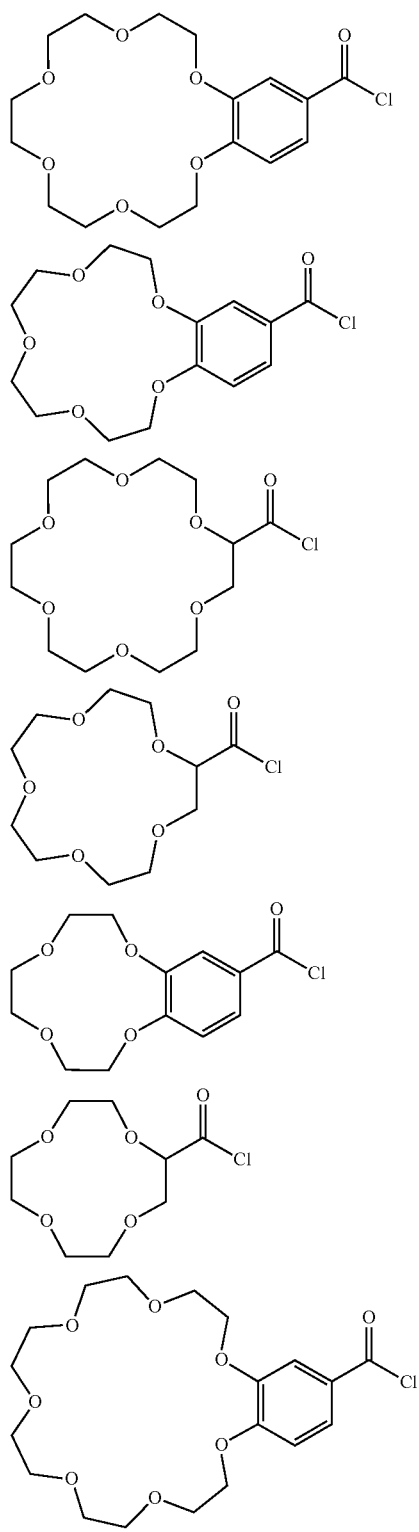
-continued
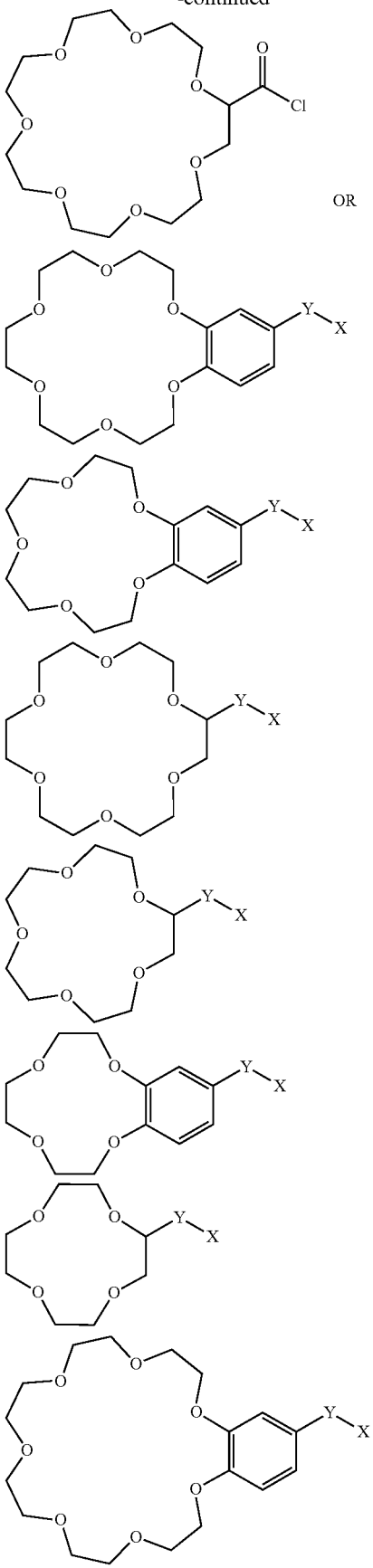
OR 73
-continued
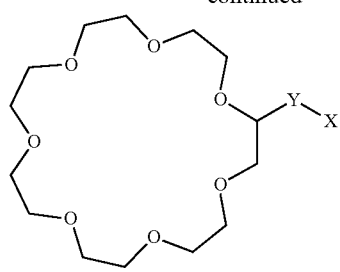
X =
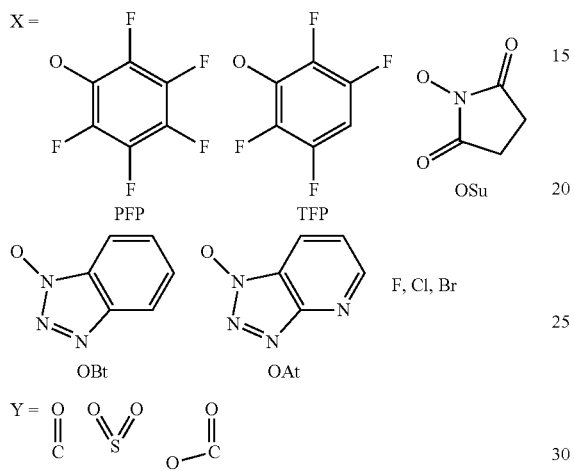
74
-continued
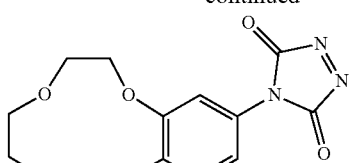
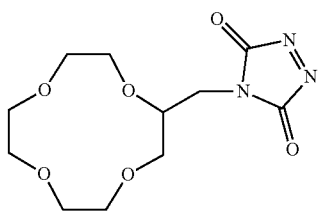
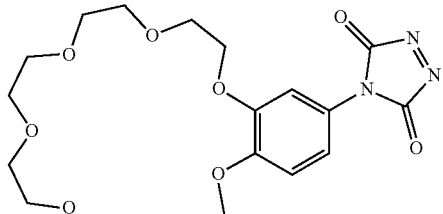
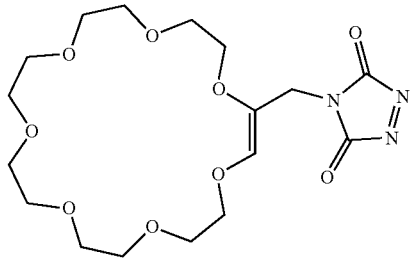 [SMILES: O=C1N=NC(=O)N1C/C1=C/OCCOCCOCCOCCOCCOCCO1]
Group II
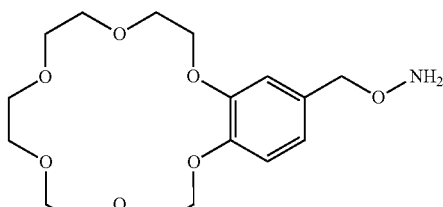
Group III
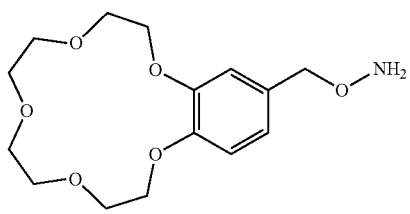
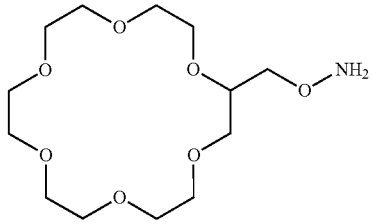

75
-continued
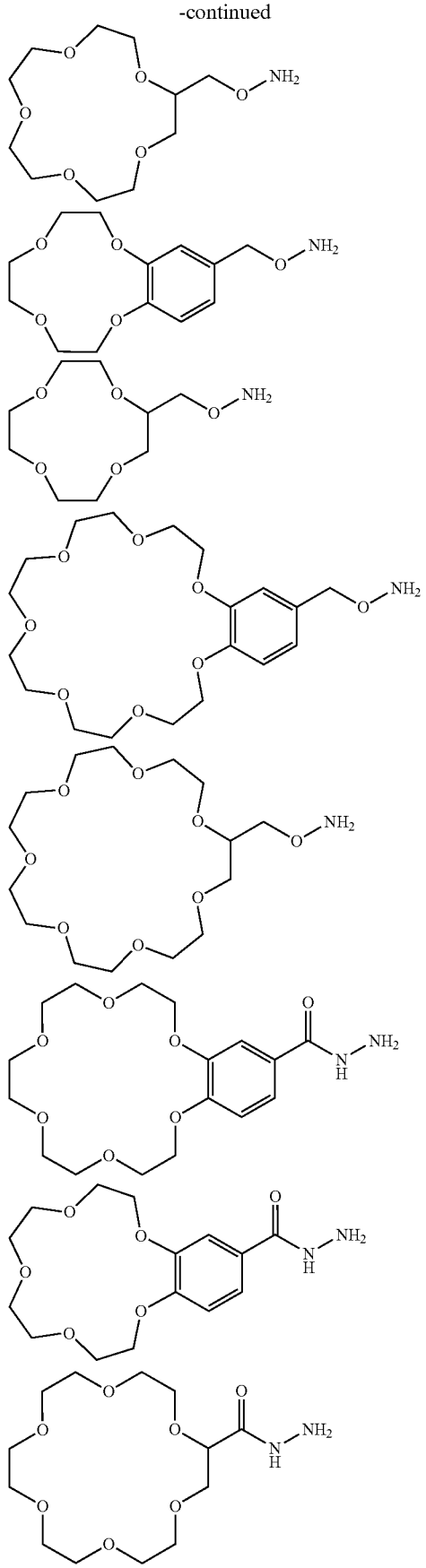
76
-continued
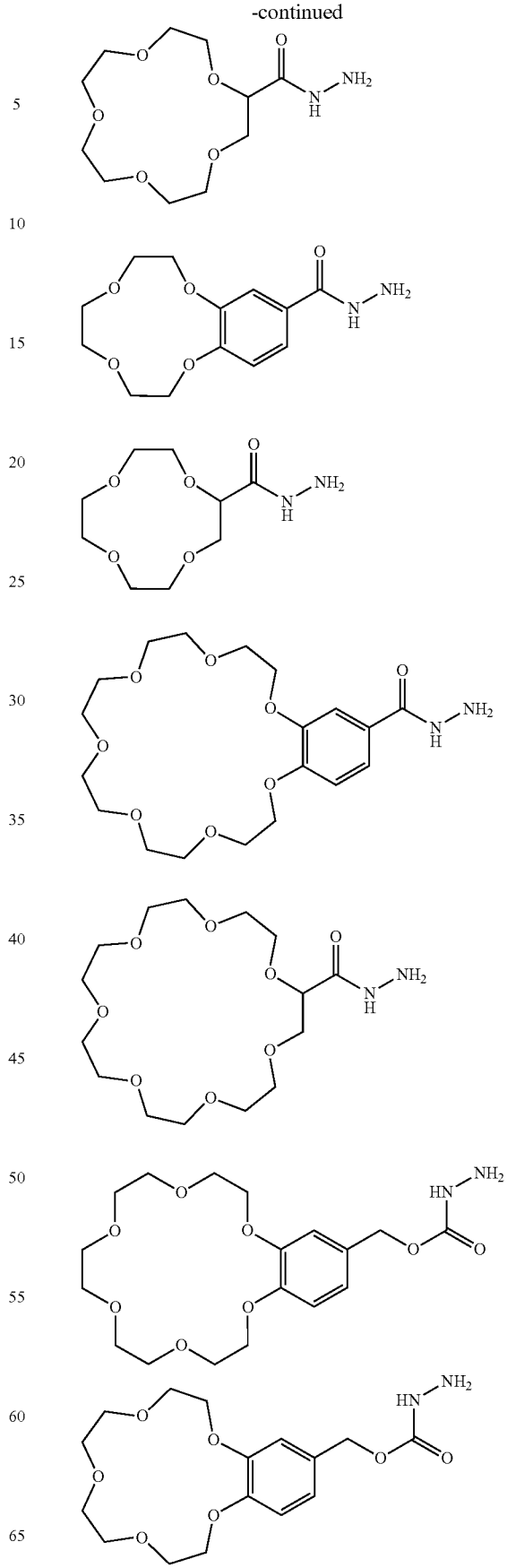

77
-continued
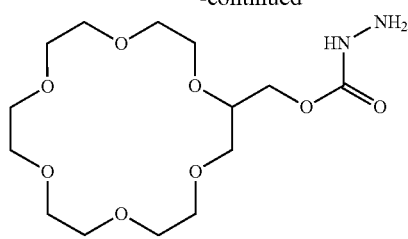
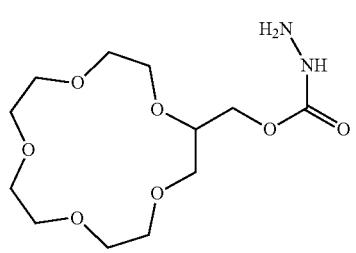
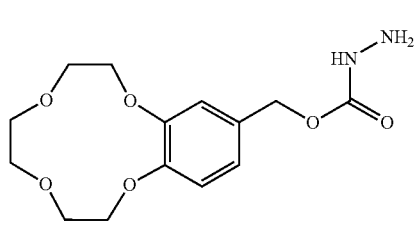
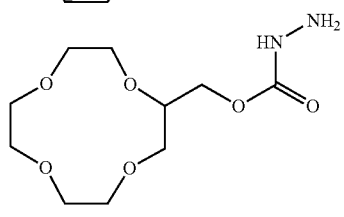
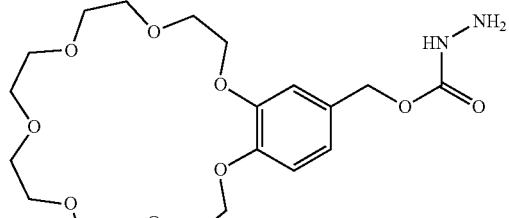
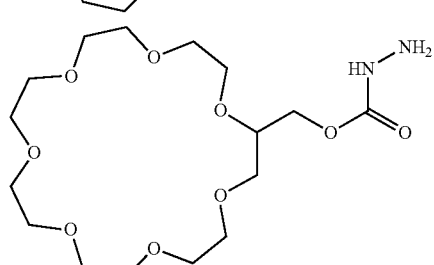
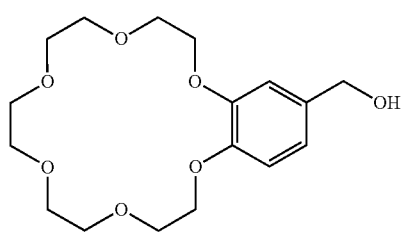
78
-continued
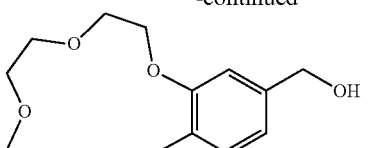
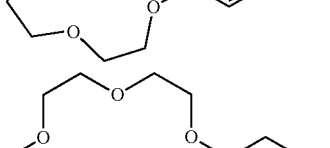
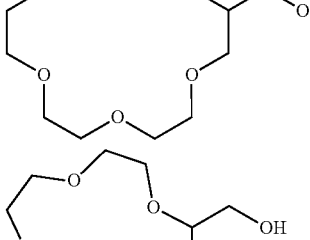
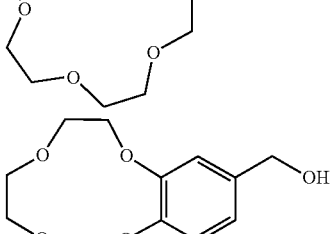
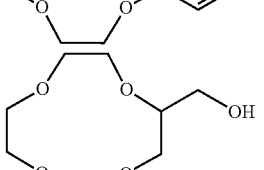
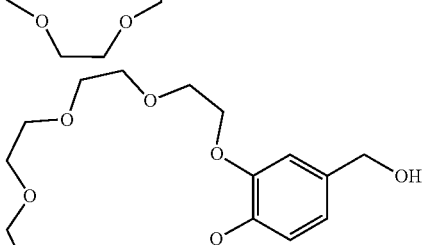
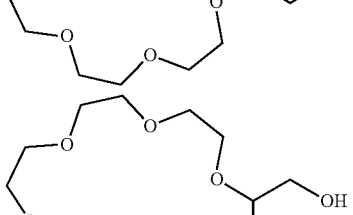
Group IV
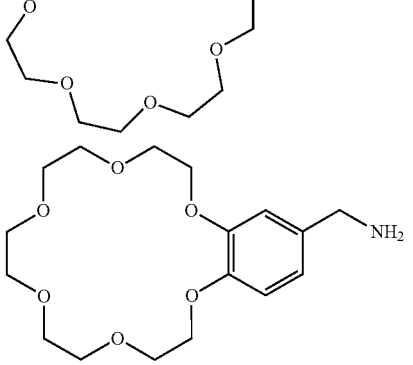

-continued

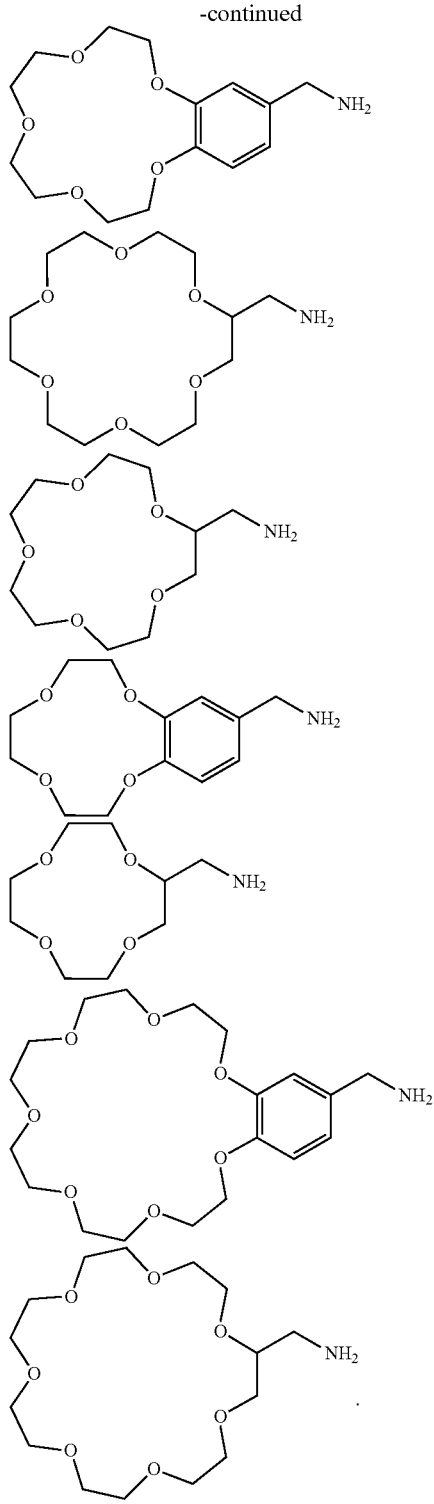

20. The method of claim 19, wherein the derivatizing agent is MB338 or MB409.

21. The method of claim 1, wherein the detection of the one or more derivatized analytes using LCMS/MS comprises the detection of the one or more derivatized analytes as an ammonium adduct.

22. The method of claim 1, wherein ammonium adducts of the derivatized one or more analytes are identified as multiple reaction monitoring transitions.

23. The method of claim 1, wherein the analyte-binding functional group is selected from the group comprising:

an acylating group, an acyl halide, an acyl chloride, a 4-Phenyl-1,2,4-triazolin-3,5-dione (PTAD), and a 1,2,4-triazoline-3,5-dione (TAD); and wherein the one or more analytes is selected from the group comprising primary amines, secondary amines, monoamines, amino acids, aliphatic hydroxides, phenolic hydroxides, estrogen hormones, THC, THC metabolites, THC analogs, cis-diene containing molecules, vitamin D, vitamin D derivatives and vitamin D metabolites.

24. The method of claim 1, wherein the derivatizing agent is selected from Group I and wherein the one or more analytes is selected from the group comprising primary amines, secondary amines, monoamines, amino acids, aliphatic hydroxides, phenolic hydroxides, estrogen hormones, THC, THC metabolites and THC analogs, or wherein the derivatizing agent is selected from Group II and wherein the one or more analytes is selected from the group comprising cis-diene containing molecules, vitamin D and vitamin D derivatives, Group I comprising

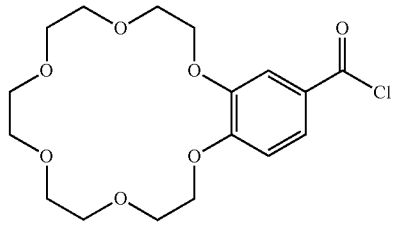

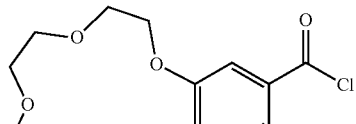

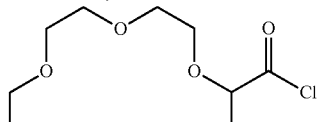

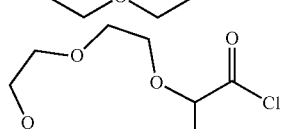

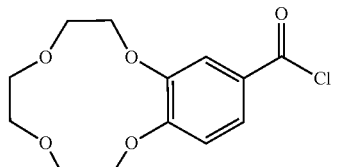

81
-continued
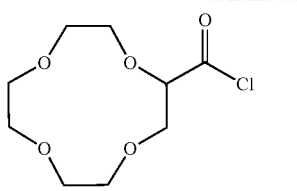
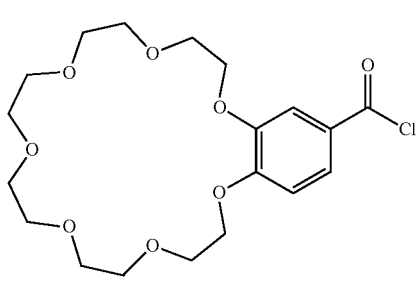
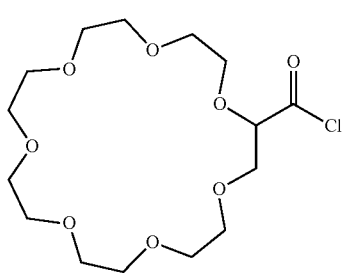
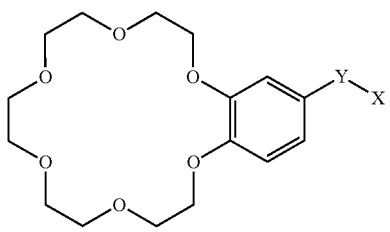
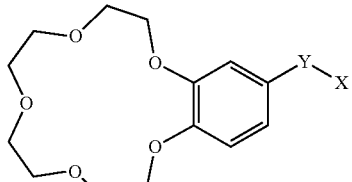
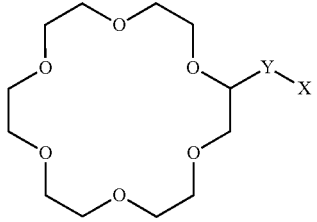
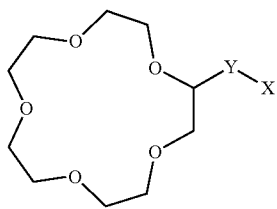
82
-continued
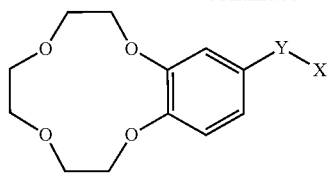
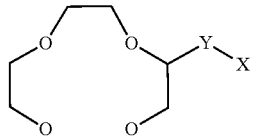
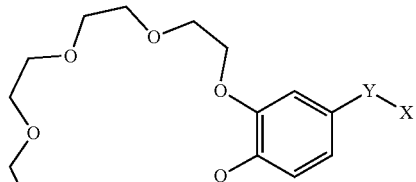
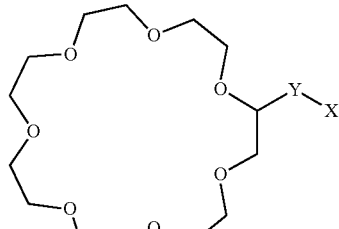
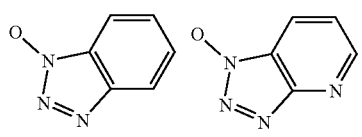 F, Cl, Br
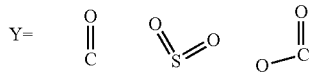
and Group II comprising
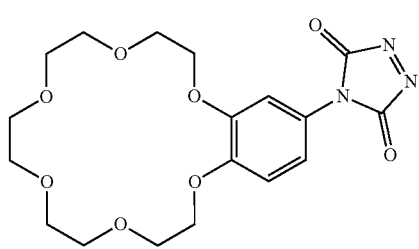

-continued

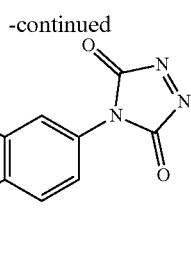

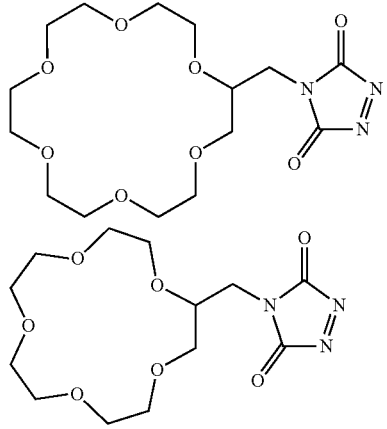

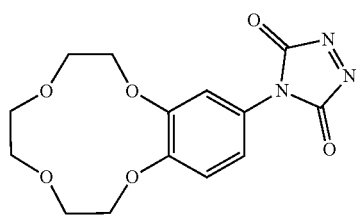

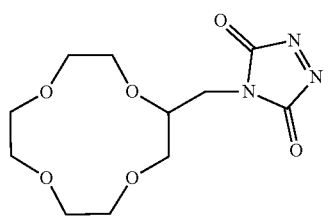

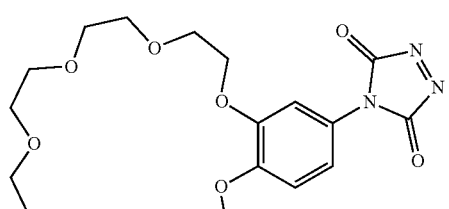

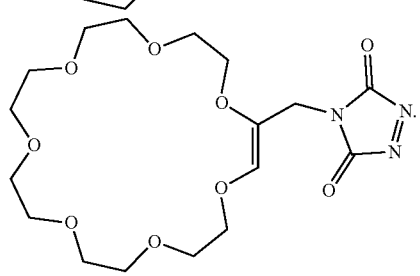

25. The method of claim 1, wherein the one or more analytes is selected from the group comprising:
   a molecule with a primary amino functional group;
   a molecule with a secondary amino functional group;
   a monoamine neurotransmitter; and
   an arylcyclohexylamine or one of its derivatives or metabolites,
   wherein the derivatizing agent is selected from Group I.

26. The method of claim 25, wherein
   the monoamine neurotransmitter is Histamine, Tryptamine, Serotonin, or Agmatine;
   the arylcyclohexylamine or one of its derivatives or metabolites is Tiletamine, 3-Methoxetamine (MXE), Methoxyketamine, N-Ethylnorletamine (Ethketamine), Ephedrine, Methamphetamine, Amphetamine or one of its derivatives or metabolites, Amphetamine (itself), methamphetamine, ephedrine, cathinone, 3,4-Methylenedioxy-N-methylamphetamine (MDMA, "Ecstasy"), or 2.5-Dimethoxy-4-methylamphetarnine (DOM, or "STP").

27. The method of claim 1, wherein the one or more analytes is selected from the group comprising:
   a molecule with a primary amino functional group;
   a molecule with a secondary amino functional group;
   a monoamine neurotransmitter; and
   an arylcyclohexylamine or one of its derivatives or metabolites,
   wherein the derivatizing agent is MB338
   MB338 being

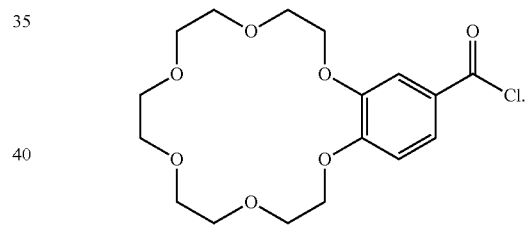

28. The method of claim 1, wherein the one or more analytes is a phenolic molecule,
   wherein the derivatizing agent is selected from Group I.

29. The method of claim 28, wherein the phenolic molecule is an estrogen hormone or one of its derivatives or metabolites, or a cannabinoid or one of its derivatives or metabolites.

30. The method of claim 29, wherein the estrogen hormone or one of its derivatives or metabolites is an estrone, an estradiol, or an estriol;
   the cannabinoid or one of its derivatives or metabolites is a Cannabigerol-type (CBG) cannabinoid, a Cannabichromene-type (CBC) cannabinoid, a Cannabidiol-type (CBD) cannabinoid, a Cannabinodiol-type (CBND) cannabinoid, a Tetrahydrocannabinol-type (THC) cannabinoid, a Cannabinol-type (CBN) cannabinoid, a Cannabitrioltype (CBT) cannabinoid, a Cannabielsointype (CBE) cannabinoid, an Isocannabinoid, a Cannabicyclol-type (CBL) cannabinoid, a Cannabicitran-type (CBT) cannabinoid, a Cannabichromanone-type (CBCN) cannabinoid, or a synthetic cannabinoid such as HU-210.

31. The method of claim 1, wherein the one or more analytes is a phenolic molecule,
wherein the derivatizing agent is MB338 MB338 being

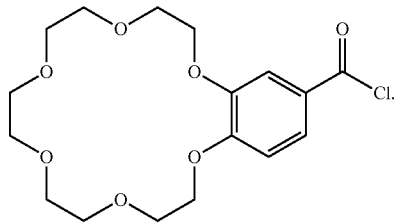 [SMILES: O=C(Cl)c1ccc2c(c1)OCCOCCOCCOCCOCCO2]

32. The method of claim 1, wherein the one or more analytes is a cis-diene containing molecule,
wherein the derivatizing agent is selected from Group II.

33. The method of claim 32, wherein the cis-diene containing molecule is a derivative of vitamin D.

34. The method of claim 33, wherein the derivative of vitamin D is 25-OH $D_3$, 25-OH $D_2$, 24,25-$(OH)_2D_3$, 1,25-$(OH)_2D_3$, and 1,25-$(OH)_2 D_2$, Cholecalciferol, 25-Hydroxycholecalciferol, 1α,25-Dihydroxycholecalciferol, Ergocalciferol, 1α,25-Dihydroxyergocalciferol, 22,23-Dihydroergocalciferol, 1α,24R,25-Trihydroxycholecalciferol, (6Z)-tacalciol, Tachysterol$_3$, Isovitamin $D_3$, or Dihydrotachysterol$_3$.

35. The method of claim 1, wherein the one or more analytes is a cis-diene containing molecule,
wherein the derivatizing agent is MB409, MB409 being

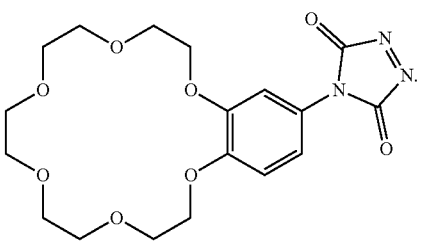 [SMILES: O=C1N=NC(=O)N1c1ccc2c(c1)OCCOCCOCCOCCOCCO2]

* * * * *